(12) United States Patent
Cohen et al.

(10) Patent No.: US 6,232,456 B1
(45) Date of Patent: *May 15, 2001

(54) SERINE PROTEASE REAGENTS AND METHODS USEFUL FOR DETECTING AND TREATING DISEASES OF THE PROSTATE

(75) Inventors: Maurice Cohen, Highland Park; Tracey L. Colpitts, Round Lake; Paula N. Friedman, Deerfield; Edward Granados, Vernon Hills; Michael R. Klass, Libertyville, all of IL (US); John C. Russell, Pleasant Prairie, WI (US); Kent D. Stewart, Gurnee; Stephen D. Stroupe, Libertyville, both of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/944,483

(22) Filed: Oct. 6, 1997

(51) Int. Cl.[7] ............................. C12N 15/57; C12N 9/64
(52) U.S. Cl. ........................................ 536/23.2; 435/226
(58) Field of Search ......................... 536/23.2; 435/226, 435/226.6

(56) References Cited

U.S. PATENT DOCUMENTS 5,840,871 * 11/1998 Hillman et al. ...................... 536/23.5
6,075,136 * 6/2000 Tang et al. ........................... 536/23.1

OTHER PUBLICATIONS

Benson et al, *Nuc. Acids Research* 25:1–6 (1997).
Birktoff et al., "Structure of Crystalline a–Chymotrypsin," *J. Mol. Biol.* 68:187–240 (1972).
Hanks et al., "Cancer of the Prostate," *Cancer Principles & Practice of Oncology* 1:4th Edition, 1073–1113 (1993).
Hansson et al., Annotation for "Stratum Corneum Chymotryptic Enzyme Precursor (SCCE)," Accession No. P49862, 1996.
Iverson et al., "Structure of HBP, a Multifuntional Protein with a Serine Proteinase Fold," *Nature Structural Biology* 4(4):265–268, 1997.
Jacobs et al., "Clinical Use of Tumor Markers in Oncology," *Curr. Prob. Cancer* 299–350 (1991).
Pantel et al., "Methods for Detection of Micrometastatic Carcinoma Cells in Bone Marrow, Blood and Lymph Nodes," *Onkologie* 18:394–401 (1995).
Suzuki et al., "Involvement of Cytoplasmic Serine Proteinase and CPP32 Subfamily in the Molecular Machinery of Caspase 3 Activation during Fas–Mediated Apoptosis," *Experimental Cell Research* 233:48–55 (1997).

(List continued on next page.)

*Primary Examiner*—Ponnathapu Achutamurthy
*Assistant Examiner*—William W. Moore
(74) *Attorney, Agent, or Firm*—Cheryl L. Becker; Mimi C. Goller

(57) ABSTRACT

A set of contiguous and partially overlapping RNA sequences and polypeptides encoded thereby, designated as PS133 and transcribed from prostate tissue is described. One polypeptide of the present invention is a member of the human serine protease family. These sequences are useful for the detecting, diagnosing, staging, monitoring, prognosticating, preventing or treating, or determining the predisposition of an individual to diseases and conditions of the prostate, such as prostate cancer. Also provided are antibodies which specifically bind to PS133-encoded polypeptide or protein, and agonists or inhibitors which prevent action of the tissue-specific PS133 polypeptide, which molecules are useful for the therapeutic treatment of prostate diseases, tumors or metastases.

9 Claims, 14 Drawing Sheets

OTHER PUBLICATIONS

Schwartz, "Cancer Markers," *Principles & Practice of Onocolgy* 1 4th Edition, 531–542 (1993).

Annotation for zd29b01.s1 Soares fetal heart NbHH19W Homo sapiens cDNA clone, accession No. W60282, 1996.

Giacobino et al., "Cloning of the TMPRSS2 Gene, Which Encodes a Novel Serine Protease with Transmembrane, LDLRA, and SRCR Domains and Maps to 21q22.3," *Genomic* 44:309–320 (1997).

Yoshida et al., "cDNA Cloning and Expression of a Novel Serine Protease, TLSP," *Biochimica et Biophysica Act* 1399:225–228 (1998).

Marra et al., GenBank–EST Accession No. AA062006, "Mus musculus cDNA clone 482709", 1996.*

Marra et al., GenBank–EST Accession No. AA073833, "Mus musculus cDNA clone 484289", 1996.*

Hillier et al., GenBank–EST Accession No. AA412318, "Homo sapiens cDNA clone 730282", 1997.*

U.S. National Cancer Institute—Cancer Genome Anatomy Project, GenBank–EST Accession No. AA532717, "Homo sapiens cDNA clone IMAGE:996784", 1997.*

Marra et al., GenBank–EST Accession No. W13212, "Mus musculus cDNA clone 317268", 1997.*

Hillier et al., GenBank–EST Accession No. W60374, "Homo sapiens cDNA clone 342025", 1997.*

* cited by examiner

```
>8288846       CTGCTGTAGC                TGCCGCCACT  GCCGTNTCCG  NCGNCANTGG  GNCCCCAGAG
>23463388                  GC            TGCCGCCACT  GCCGTCTCCG  CCGCCACTGG  GCCCCCNGAG
Consensus      CTGCTGTAGC                TGCCGCCACT  GCCGTCTCCG  CCGCCACTGG  GCCCCAGAG >8288846       CCCCAGCCCC    AGAGCCTAGG  AACCTGGGGC  C
>23463388      CCCCAGCNCC    AGAGCCTAGG  AACCTGGGGC  CCGCTCCTCC  CCCCTCCAGG
Consensus      CCCCAGCCCC    AGAGCCTAGG  AACCTGGGGC  CCGCTCCTCC  CCCCTCCAGG >23463388      CCATGAGGAT    TCTGCAGTTA  ATCCTGCTTG  CTCTGGCAAC  AGGGCTTGTA
Consensus      CCATGAGGAT    TCTGCAGTTA  ATCCTGCTTG  CTCTGGCAAC  AGGGCTTGTA >23463388      GGGGGAGAGA    CCAGGATCAT  CAAGGGGTTC  GAGTGCNAGC  CTCACTCCCA
>2531505       GGGGGAGAGA    CCAGGATCAT  CAAGGGGTTC  GAGTGCNAGC  CTCACTCCCA
Consensus      GGGGGAGAGA    CCAGGATCAT  CAAGGGGTTC  GAGTGCNAGC  CTCACTCCCA >23463388      GCCCTGGCAG    GCAGCCCTGT  TCGAGAAAAC  GCGGCTACTC  TGTGGGGCGA
>2531505       GCCCTGGCAG    GCAGCCCTGT  TCAAGAAGAC  GCGGCTACTC  TGTGGGGCGA
Consensus      GCCCTGGCAG    GCAGCCCCGT  TCRAGAAARAC GCGGCTACTC  TGTGGGGCGA >2531505       CGCTCATCGC    CCCCAGATGG  CTCCTGACAG  CAGCCCACTG  CCTCAAGCCC
Consensus      CGCTCATCGC    CCCCAGATGG  CTCCTGACAG  CAGCCCACTG  CCTCAAGCCC
```

FIG. 1A-1

```
>2531505     CGCTACATAG TTCACCTGGG GCAGCACAAC CTCCAGAAGG AGGAGGCTG
Consensus    CGCTACATAG TTCACCTGGG GCAGCACAAC CTCCAGAAGG AGGAGGCTG >2531505     TGAGCAGACC CGGACAGCCA CTGAGTCCTT CCCCCACCCC GGCTTCAACA
Consensus    TGAGCAGACC CGGACAGCCA CTGAGTCCTT CCCCCACCCC GGCTTCAACA >2531505     ACAGCCTCCC CAACAAAGAC CACCGCAATG ACATC
>1725220                      GAC CACCGCAATG ACATCATGCT GGTGAAGATG
Consensus    ACAGCCTCCC CAACAAAGAC CACCGCAATG ACATCATGCT GGTGAAGATG >1725220     GCATCGCCAG TCTCCATCAC CTGGGCTGTG CGACCCCTCA CCCTCTCCTC
Consensus    GCATCGCCAG TCTCCATCAC CTGGGCTGTG CGACCCCTCA CCCTCTCCTC >1725220     ACGCTGTGTC ACTGCTGGCA CCAGCTGCCT CATTTCCGGC TGGGGCAGCA
Consensus    ACGCTGTGTC ACTGCTGGCA CCAGCTGCCT CATTTCCGGC TGGGGCAGCA >1725220     CGTCCAGCCC CCAGTTACGC CTGCCTCACA CCTTGCGATG CGCCAACATC
Consensus    CGTCCAGCCC CCAGTTACGC CTGCCTCACA CCTTGCGATG CGCCAACATC
```

FIG. 1A-2

```
>1725220    ACCATCATTG AGCACCAGAA GTGTGAGAAC GCCTACCCCG GCAACATCAC
>1856238                AGCACCAGAA            AAC GCCTACCCCG GCAACATCAC
Consensus   ACCATCATTG AGCACCAGAA GTGTGAGAAC GCCTACCCCG GCAACATCAC >1725220    AGACACCATG GTGTGTG
>1856238    AGACACCATG GTGTGTGCCA GCGTGCAGGA AGGGGGCAAG GACTCCTGCC
Consensus   AGACACCATG GTGTGTGCCA GCGTGCAGGA AGGGGGCAAG GACTCCTGCC >1856238    AGGGTGACTC CGGGGGCCCT CTGGTCTGTA ACCAGTCTCT TCAAGGCATT
Consensus   AGGGTGACTC CGGGGGCCCT CTGGTCTGTA ACCAGTCTCT TCAAGGCATT >1856238    ATCTCCTGGG GCCAGGATCC GTGTGCGATC ACCCGAAAGC CTGGTGTCTA
<g1367041              GCCAGGATCC GTGTGCGATC ACCCGAAAGC CTGGTGTCTA
Consensus   ATCTCCTGGG GCCAGGATCC GTGTGCGATC ACCCGAAAGC CTGGTGTCTA
```

FIG. 1A-3

```
>1856238      CACGAAAGTC  TGCAAATATG  TGGACTGGAT  CCAGGAGACG  ATGAAGAACA
<g1367041     CACGAAAGTC  TGCAAATATG  TGGACTGGAT  CCAGGAGACG  ATGAAGAACA
Consensus     CACGAAAGTC  TGCAAATATG  TGGACTGGAT  CCAGGAGACG  ATGAAGAACA >1856238      ATTAGACTGG  ACCCACCCAC  CACAGCCCAT  CACCCTCCA
<g1367041     ATTAGACTGG  ACCCACCCAC  CACAGCCCAT  CACCCTCCAT  TTCCACTTGG
Consensus     ATTAGACTGG  ACCCACCCAC  CACAGCCCAT  CACCCTCCAT  TTCCACTTGG <g1367041     TGTTTGGTTC  CTGTTCACTC  TGTTAATAAG  AAACCCTAAG  CCAAGACCCT
Consensus     TGTTTGGTTC  CTGTTCACTC  TGTTAATAAG  AAACCCTAAG  CCAAGACCCT <g1367041     CTGCGAACAT  TCTTTGGGCC  TCCTGGACTA  CAGGAGATGC  TGTCACTTAA
Consensus     CTGCGAACAT  TCTTTGGGCC  TCCTGGACTA  CAGGAGATGC  TGTCACTTAA
```

FIG. 1B-1

```
<g1367041      TAATCGAACC  TGGGGTTCGA  AATCNAGTGA  GACCTGGATT  CAAATTCTGC
Consensus      TAATCGAACC  TGGGGTTCGA  AATCNAGTGA  GACCTGGATT  CAAATTCTGC <g1367041      CTTGAAATAT  TGTGACTCTG  GGAATGACAA  CACCTGGTTT  GTTCTCTGTT
Consensus      CTTGAAATAT  TGTGACTCTG  GGAATGACAA  CACCTGGTTT  GTTCTCTGTT <g1367041      GTATCCCCAG  CCCCGAAAGA  CAGCTCCTGG  CCATATATCA  AGGTTTCAAT
Consensus      GTATCCCCAG  CCCCGAAAGA  CAGCTCCTGG  CCATATATCA  AGGTTTCAAT <g1367041      AAATATTTGC  TAAATG
Consensus      AAATATTTGC  TAAATG
```

FIG. 1B-2

|  | Abbreviation | Full Name and GenBank Entry | | Protein Sequence |
|---|---|---|---|---|
| SEQ ID NO 24 | PS133 | | M14058 | IIKGFEC XPHSQPWQAA |
| SEQ ID NO 28 | C1s | Complement Componant C1s | M18767 | IIGGSDA DIKNFPWQVF |
| SEQ ID NO 29 | C1r | Complement Componant C1r | M75154 | IIGGQKA KMGNFPWQVF |
| SEQ ID NO 30 | Myeloblastin | Myeloblastin | M34379 | IVGGHEA QPHSRPYMAS |
| SEQ ID NO 31 | Medullasin | Medullasin | M96326 | IVGGRRA RPHAWFPMVS |
| SEQ ID NO 32 | Azurocidin | Azurocidin | L33404 | IVGGRKA RPRQFPFLAS |
| SEQ ID NO 33 | Stratum | Stratum Corneum Chymotrypsin | M27602 | IIDGAPC ARGSHPWQVA |
| SEQ ID NO 34 | Trypsin2 | Pancreatic Tryspin 2 | D45417 | IVGGYIC EENSVPYQVS |
| SEQ ID NO 35 | Trypsin3 | Mesotrypsinogen | M22612 | IVGGYTC EENSLPYQVS |
| SEQ ID NO 36 | Trypsin1 | Pacreatic Tryspin 1 | M18157 | IVGGYNC EENSVPYQVS |
| SEQ ID NO 37 | Kallikrein3 | glandular kallikrein type 2 | M26663 | IVGGWEC EKHSQPWQVA |
| SEQ ID NO 38 | PSA | Prostate specific antigen | M25629 | IVGGWEC EKHSQPWQVL |
| SEQ ID NO 39 | Kallikrein4 | pancreatic kallikrein | M28879 | IVGGWEC EQHSQPWQAA |
| SEQ ID NO 40 | GranzymeB | Granzyme B | P20718 | IIGGHEA KPHSRPYMAY |
| SEQ ID NO 41 | GranzymeH | Granzyme H | M16117 | IIGGHEA KPHSRPYMAF |
| SEQ ID NO 42 | CathepsinG | Cathepsin G | M64269 | IIGGRES RPHSRPYMAY |
| SEQ ID NO 43 | Chymase | Chymase | M84526 | IIGGTEC KPHSRPYMAY |
| SEQ ID NO 44 | FactorD | coagulation factor D | L23134 | MLGGREA EAHARPYMAS |
| SEQ ID NO 45 | Metase | Metase | M18737 | IIGGREV IPHSRPYMAS |
| SEQ ID NO 46 | Hanuka | coagulation Hanuka factor | D17525 | IIGGNEV TPHSRPYMVL |
| SEQ ID NO 47 | Rafactor | RA-reactive factor | M11309 | IFNGRPA QKGTTPWIAM |
| SEQ ID NO 48 | FactorIX | coagulation factor IX | M22613 | VVGGEDA KPGQFPWQVV |
| SEQ ID NO 49 | FactorX | coagulation factor X | J02933 | IVGGQEC KDGECPWQAL |
| SEQ ID NO 50 | FactorVII | coagulation factor VII | M11228 | IVGGKVC PKGECPWQVL |
| SEQ ID NO 51 | ProteinC | coagulation factor C | | LIDGKMT RRGDSPWQVV |

FIG. 3A-1

| | Abbreviation | Full Name and GenBank Entry | | Protein Sequence |
|---|---|---|---|---|
| SEQ ID NO 52 | Thrombin | Thrombin | M17262 | IVEGSDA EIGMSPWQVM |
| SEQ ID NO 53 | Plasmin | Plasmin | K02922 | VVGGCVA HPHSWPWQVS |
| SEQ ID NO 54 | apolip | apolipoprotein | P08519 | IVGGCVA HPHSWPWQVS |
| SEQ ID NO 55 | MSP | Macrophage stimulating protein | L11924 | VVGGHP. .GNS.PWTVS |
| SEQ ID NO 56 | HGF | Hepatocyte growth factor | M73239 | VVNGIPT RTNI.GWMVS |
| SEQ ID NO 57 | Elastase3 | pacreatic elastase type 3B | M18692 | VVNGEDA VPYSWPWQVS |
| SEQ ID NO 58 | ProteaseE | Protease E | D00306 | VVHGEDA VPYSWPWQVS |
| SEQ ID NO 59 | Elastase | Elastase | M16631 | VVGGEEA RPNSWPWQVS |
| SEQ ID NO 60 | Elastase2B | Pancreatic elastase type 2B | M16653 | MLGGEEA RPNSWPWQVS |
| SEQ ID NO 61 | Caldecrin | Caldecrin patent application WO9600287 | | VVGGEDA RPHSWPWQIS |
| SEQ ID NO 62 | Chymotrypsin | Chymotrypsin | M24400 | IVNGEDA VPGSWPWQVS |
| SEQ ID NO 63 | Kallikrein2 | human kallikrein | M13143 | IVGGTNS SWGEWPWQVS |
| SEQ ID NO 64 | FactorXI | blood coagulation factor XI | M13142 | IVGGTAS VRGEWPWQVT |
| SEQ ID NO 65 | Enteropep | Enteropeptidase | P98073 | IVGGSNA KEGAWPWVVG |
| SEQ ID NO 66 | Prostasin | Prostasin | U33446 | ITGGSSA VAGQWPWQVS |
| SEQ ID NO 67 | Hepsin | Hepsin | M18390 | IVGGRDT SLGRWPWQVS |
| SEQ ID NO 68 | Acrosin | Acrosin | M77379 | IVGGKAA QHGAWPWMVS |
| SEQ ID NO 69 | Tryptase | Tryptase | M30038 | IVGGQEA PRSKWPWQVS |
| SEQ ID NO 70 | FactorXII | blood coagulation factor XII | M11723 | VVGGLVA LRGAHPYLAA |
| SEQ ID NO 71 | Hepatocyteact | HGF activator | D14012 | IIGGSSS LPGSHPWLAA |
| SEQ ID NO 72 | t-PA | tissue plasminogen activator | D01096 | IKGGLFA DIASHPWQAA |
| SEQ ID NO 73 | UK | urokinase | D11143 | IIGGEFT TIENQPWFAA |
| SEQ ID NO 74 | FactorI | complement factor I | J02770 | IVGGKRA QLGDLPWQVA |

FIG. 3A-2

```
            51                          *****************                                                                          ***** 150
PS133       L....FXKT.     RLLCGATLI APRWLLTAAH C....LKPR. .YIVHLGQHN LQKE.EGCEQ TRTATESFPH PG...FNNSL PNKDH..... ..RNDIMLVK
C1s         FD.NPWA...     .....GGALI NEYWVLTPAH VVEGNREPTM YV........ ..GSTSVQTS RL.AKSKMLT PEHVFIHPGW KLLEVPEGRT NFDNDIALVR
C1r         TNIHGRG...     .....GGALL GDRWILTAAH TLYPKEHEAQ SN........ ..ASLDVFLG HTNVEELMKL GNHPIRRVSV HPDYRQDESY NFEGDIALLE
Myeloblastin LQMRGNP.GS    .HFCGGTLI HPSFVLTAPH CLRDIPQRL. .VNVVLGAHN VRTQE.PTQQ HFSVAQVF.. ......... .LNNYDAE NKLNDILLIQ
Medullasin  LQLR....GG     .HFCGATLI APNFVMSAAH CVANVNVRA. .VRVVLGAHN LSRRE.PTRQ VFAVQRIF.. ......... ...ENGYDPV NLLNDIVILQ
Azurocidin  IQ...NQ.GR     .HFCGGALI HARFVMTAAS CFQSQNPGV. .STVVLGAYD LRRREROSRQ TFSISSMS.. ......... ...ENGYDPQ QNLNDLMLLQ
Stratum     L....LSGNQ     .LHCGGVLV NERWVLTAAH C....KMNE. .YTVHLGSDT L...GDRRAQ RIKASKSFRH PG...YSTQT HV........ ....NDLMLVK
Trypsin2    L....NS.GY     .HFCGGSLI SEQWVVSAGH C......... C....YKSR. .IQVRLGEHN IEVL.EGNEQ FINAAKIIRH PK...YNSRT LD........ .......NDILLIK
Trypsin3    L....NS.GS     .HFCGGSLI SEQWVSAAH C......... C....YKTR. .IQVRLGEHN IKVL.EGNEQ FINAAKIIRH PK...YNRDT LD........ .......NDIMLIK
Trypsin1    L....NS.GY     .HFCGGSLI NEQWVVSAGH C....YKSR. .IQVRLGEHN IEVL.EGNEQ FINAAKIIRH PQ...YDRKT LN........ .......NDIMLIK
Kallikrein3 V....YSHGW     .AHCGGVLV HPQWVLTAAH C....LKKN. .SQWMLGRHN LFEP.EDTGQ RVPVSHSFPH PL...YNMSL LKHQSLRPDE DSSHDLMLLR
PSA         V....ASRGR     .AVCGGVLV HPQWVLTAAH C....IRNK. .SVILLGRHS LFHP.EDTGQ VFQVSHSHSFPH PL...YDMSL LKNRFLRPGD DSSHDLMLLR
Kallikrein4 L....YHFST     .FQCGGILV HRQWVLTAAH C....ISDN. .YQLWLGRHN LFDD.ENTAQ FVHVSESFPH PG...FNMSL LENHTRQADE DYSHDLMLLR
GranzymeB   LMIWDQKSLK     .R.CGGFLI QDDFVLTAAH CWGSSIN... ..VTLGAHN IKE.QEPTQQ FIPVKRAIPH PA...YN... ........ P.K NFSNDIMLLQ
GranzymeH   VQFLQEKSRK     .R.CGGILV RKDFVLTAAH CQGSSIN... ..VTLGAHN IKE.QERTQQ FIPVKRPIPH PA...YN... ........ P.K NFSNDIMLLQ
Cathepsing  LQIQSPAGQS     .R.CGGFLV REDFVLTAAH CWGSNIN... ..VTLGAHN IQR.RENTQQ HITARRAIRH PQ...YN... ........ .Q.R TIQNDIMLLQ
Chymase     LEIVTSNGPS     .KFCGGFLI RRNFVLTAAH CAGRSIT... ..VTLGAHN ITE.EEDTWQ KLEVIKQFRH PK...YN... ........ ..T.S TLHHDIMLLK
FactorD     VQL....NGA     .HLCAGVLV AERWLSAAH CLEDAADGK. .VQVLLGAHS LSQ.PEPSKR LYDVLRAVPH PD...SQ... ........ ..P.D TIDHDLLLLQ
Metase      LQR....NGS     .HLCGGVLV HPKWVLTAAH CLAQRM.AQ. .LRLVLGLHT LDS.PGLT.. .FHIKAAIQH PR...YK... ........ ...PVP ALENDLALLQ
Hanuka      LSL....DRK     .TICAGALI AKDWVLTAAH C...NLNKR. .SQVILGAHS ITR.EEPTKQ IMLVKKEFPY PC...YD... ........ ....PA. TREGDLKLLQ
Rafactor    LSHLNG.QP.     ..FCGGSLL GSSWIVTAAH CLHQSLDPKD PTLRDSDLLS PSDFKIILGK HWRLRSDEN. EQHLGVKHTT LHPKYD..PN TFENDVALVE
FactorIX    L..NGKVDA.     .FCGGSIV NEKWIVTAAH C........ ......VET GVKITVVAGE HNIEETEHT. EQKRNVIRII PHHNYNAAIN KYNHDIALLE
FactorX     LI.NEENEG.     .FCGGTIL SEFYILTAAH C........ ......LYQ AKRF...EGD RNTEQEEGG. EAVHEVEVVI KHNRFTK..E TYDFDIAVLR
FactorVII   LL.VNGAQ..     .LCGGTLI NTIWVSAAH CF.....DK. ......IKN WRNLIAVLGE HDLSEHDGD. EQSRRVAQVI IPSTY..VPG TTNHDIALLR
ProteinC    LL.DSKKKL.     .ACGAVLI HPSWVLTAAH CM.......D ..........E SKKLLVRLGE YDLRRWEKW. ELDLDIKEVF VHPNYSK..S TTDNDIALLH
```

FIG. 3B-1

```
Thrombin      LFRKSPQEL....LCGASLI SDRWVLTAAH CLLYPPWDK..........NFT ENDLLVRIGK HSRTRYERNI EKISMLEKIY IHPRYN.WRE NLDRDIALMK
Plasmin       LRTR.FG.....MHFCGGTLI SPEWVLTAAH CLEKSPRP.S SYKVILGAH..Q................... EVNLEPH VQEIEVSRLF LEP..........TRKDIALLK
apolip        LRTR.FG.....KHFCGGTLI SPEWVLTAAH CLKKSSRP.S SYKVILGAH..Q................... EVNLESH VQEIEVSRLF LEP..........TQADIALLK
MSP           LRNR.QG.....QHFCGGSLV KEQWILTARQ CFSSCHMPLT GYEWLGTLF QN................... PQHGEPS LQRVPVAKMV CGP..........SGSQLVLLK
HGF           LRYR..N.....KHICGGSLI KESWILTARQ CFPS..RDLK DYEAWLGIHD VH................... GRGDEKC KQVLNVSQLV YGP..........EGSDLVLMK
Elastase3     LQYE.KSGS.FYHTCGGSLI APDWVTAGH CISSS.....R TYQVVLGEYD RA...................VKEGPEQ VIPINSGDLF VHPLWNRSCV ACGNDIALIK
ProteaseE     LQYE.KSGS.FYHTCGGSLI APDWVTAGH CISRD.....L TYQVVLGEYN LA...................VKEGPEQ VIPINSEELF VHPLWNRSCV ACGNDIALIK
Elastase      LQYS.SNGK.WYHTCGGSLI ANSWVLTAAH CISSS.....R TYRVGLGRHN LY...................V.A.ESG SLAVSVSKIV VHKDWNSNQI SKGNDIALLK
Elastase2B    LQYS.SNGQ.WYHTCGGSLI ANSWVLTAAH CISSS.....R IYRMLGQHN LY...................V.A.ESG SLAVSVSKIV VHKDWNSNQV SKGNDIALLK
Caldecrin     LQYL.KNDT.WRHTCGGTLI ASNFVLTAAH CISNT.....R TYRVAVGKNN LE...................V.EDEEG SLFVGVDTIH VHKRWNA..L LLRNDIALIK
Chymotrypsin  LQ.....DKT.GFHFCGGSLI SEDWVTAAH CGVRT...:.S DV.VVAGEFD Q................... GSDEEN IQVLKIAKVF KNPKF..SIL TVNNDITLLK
Kallikrein2   LQV...KLTA QRHLCGGSLI GHQWVLTAAH CFDGLPL.QD VWRIYSGILN LS.................. DITK.DT PFSQI....KE IIIHQNYKYS EGNHDIALIK
FactorXI      LHT...TSPT QRHLCGGSII GNQWILTAAH CFYGVES.PK ILRVYSGILN QS.................. EIKE.DT SFFGV....QE IIIHDQYKMA ESGYDIALLK
Enteropep     LYY......G GRLLCGASLV SSDMLVSAAH CVYGRNLEPS KWTAILGLHM KS.................. NLTSPQT VPRLI....DE IVINPHYNRR RKDNDIAMMH
Prostasin     ITY.....EGV...HVCGGSLV SEQWLSAAH CFPS.EHHKE AYEVKLGAHQ LD.................. SYSE.DA KVSTL....KD IIPHPSYLQE GSQGDIALLQ
Hepsin        LRY.....DGA....HLCGGSLL SGDWVLTAAH CFPERNRVLS RWRVFAGAVA QA.................. SPHGLQL GVQAVVYHGG YLPFRDPNSE ENSNDIALVH
Acrosin       LQIF.RYNSH RYHTCGGSLL NSRWVLTAAH CFVGKNNVHD WRLVFGAKEI TY.................. GNNKPVK APLQERYVEK IIIHEKYNSA TEGNDIALVE
Tryptase      LRVR.DR..Y WMHFCGGSLI HPQWVLTAAH CLGPDVKDLA TLRVQLREQH LY.................. YQD.....QLLPVSR IIVHPQFYII QTGADIALLE
FactorXII     LYWGHS......FCAGSLI APCWVLTAAH CLQDRP.APE DLTVLGQER RN.................. HSCEP CQTLAVRSYR LHEAFSP.VS .YQHDLALLR
Hepatocyteact IYIGDS......FCAGSLV HTCWVSAAH CFSHSP.PRD SVSVVLGQHF FN.................. RTTDV TQTFGIEKYI PYTLYSV.FN PSDHDLVLIR
t-PA          IFAKHRRSPG ERFLCGGILI SSCWILSAAH CFQERF.PPH HLTVILGRTY RV.................. VPGEE EQKFEVEKYI VHKEFDDDT..YDNDIALLQ
UK            IYRRH.RGGS VTYVCGGSLI SPCWISATH SPCWVISATH CFIDYP.KKE DYTVYLGRSR LN.................. SNTQG EMKFEVENLI LHKDYSADTL AHHNDIALLK
FactorI       I.......KDA SGITCGGIYI GGCWILTAAH CLRASK.THR YQIWTTVDW IH.................. PDLKR IVIEYVDRII FHENYNAGT..YQNDIALIE
```

FIG. 3B-2

```
             151                                                                                                    250
PS133        MASPV.....  SITWAVRPLT  LSSRCV....  ..........  TAGTSCLI    SGWGSTSSPQ  LR.LPHTLRC  ANITIIEHQK  CEN...AYP   GN.....ITD  TMVCASVQEG
C1s          LKDP.....V  KMGPTVSPIC  LPGTSSDYNL  M..DGDLGLI  SGWGRTEKRD  R...AVRLKA  ARLPVAPLRK  CKEVKVEKPT  ADAEAYVFTP  NMICAGGEK.
C1r          LENS.....V  TLGPNLLPIC  LPDNDTFYDL  ..........  .GLMGIV     SGFGVMEEK.  I...AHDLRF  VRLPVANPQA  CENMLRGKNR  MD....VFSQ  NMFCAGHPSL
Myeloblastin LSSPAN....  .LSASVTSVQ  LPQQDQP...  ..........  .VPHGTCQLA  MGWGRVGA.H  DP.PAQVLQE  LNVTVV.TFF  CR........  ......P     HNICTFVPRR
Medullasin   LNGSAT....  .INANVQVAQ  LPAQGRR...  ..........  .LGNGVQCLA  MGWGLLGR.N  RG.IASVLQE  LNVTVV.TSL  CR........  ......R     SNVCTLVRGR
Azurocidin   LDREAN....  .LTSSVTILP  LPLQNAT...  ..........  .VEAGTRCQV  AGWGSQRS.G  GR.LSRFPRF  VNVTVTPEDQ  CR........  ......P     NNVCTGVLTR
Stratum      LNSQAR....  .LSSMVKKVR  LPSRCE....  ..........  .PPGTTYCTV  SGWGTTTSPD  VT.FPSDLMC  VDVKLISPQD  CTK....VYK  DL.....LEN  SMLCAGIPDS
Trypsin2     LSSPA.V...  .INSRVSAIS  LPTAPP....  ..........  .AAGTESLI   SGWGNTLSSG  AD.YPDELQC  LDAPVLSQAE  CEA....SYP  GK.....ITN  NMFCVGFLEG
Trypsin3     LSSPA.V...  .INARVSTIS  LPTAPP....  ..........  .AAGTECLI   SGWGNTLSFG  AD.YPDELKC  LDAPVLTQAE  CKA....SYP  GK.....ITN  SMFCVGFLEG
Trypsin1     LSSRA.V...  .INARVSTIS  LPTAPP....  ..........  .ATGTKCLI   SGWGNTASSG  AD.YPDELQC  LDAPVLSQAK  CEA....SYP  GK.....ITS  NMFCVGFLEG
Kallikrein3  LSEPAK....  .ITDVVKVLG  LPTQEP....  ..........  .ALGTTCYA   SGWGSIEPEE  FL.RPRSLQC  VSLHLLSNDM  CAR....AYS  EK.....VTE  FMLCAGLWTG
PSA          LSEPAE....  .LTDAVKVMD  LPTQEP....  ..........  .ALGTTCYA   SGWGSIEPEE  FL.TPKKLQC  VDLHVISNDV  CAQ....VHP  QK.....VTK  FMLCAGRWTG
Kallikrein4  LTEPADT...  .ITDAVKVVE  LPTQEP....  ..........  .EVGSTCLA   SGWGSIEPEN  FS.FPDDLQC  VDLKILPNDE  CEK....AHV  QK.....VTD  FMLCVGHLEG
GranzymeB    LERKAKR...  .TRAVQPLR   LPSNKAQ...  ..........  .VKPGQTCSV  AGMGQTAPLG  .K.HSHTLQE  VKMTVQEDRK  CESDLRHYYD  ST......IE  ..LCVGDPEI
GranzymeH    LERKAKW...  .TTAVRPLR   LPSSKAQ...  ..........  .VKPGQLCSV  AGMGYVS.MS  .T.LATTLQE  VLLTVQKDCQ  CERLFHGNYS  RA......TE  ..ICVGDPKK
CathepsinG   LSRRVRR...  .NRNVNPVA   LPRAQEG...  ..........  .LRPGTLCTV  AGMGRVS.MR  .R.GTDTLRE  VQLRVQRDRQ  CLRIF.GSYD  PR......RQ  ..ICVGDRRE
Chymase      LKEKASL...  .TLAVGTLP   FPSQFNF...  ..........  .VPPGRMCRV  AGWGRTGVLK  .P.GSDTLQE  VKLRLMDPQA  CSHF..RDFD  HN......LQ  ..LCVGNPRK
FactorD      LSEKATL...  .GPAVRPLP   WQRVDRD...  ..........  .VAPGTLCDV  AGMGIVNHAG  .R.RPDSLQH  VLLPVLDRAT  CNRRTHH..D  GA......ITE  RLMCAESNRR
Metase       LDGKVKP...  .SRTIRPLA   LPSKRQV...  ..........  .VAAGTRCSM  AGMGLTHQGG  .R.LSRVLRE  LDLQVLDTRM  CNNSRFW..N  GS......LSP  SMVCLAADSK
Hanuka       LTEKAKI...  .NKYVTILH   LPKKGDD...  ..........  .VKPGTMCQV  AGMGRTHNSA  .S.WSDTLRE  VNITIIDRKV  CNDRNHYNFN  PV......IGM  NMVCAGSLRG
Rafactor     LLES.....P  VLNAFVMPIC  LPEGPQQEGA  MV......IV  SGWGKQFLQR  FPET...LME  IEIPIVDHST  C..QKAYAPL  KKKVTRDMIC  AG...EK.EG
FactorIX     LDEP.....L  VLNSYVTPIC  IADKEYT.NI  FLKFG.SGYV  SGWGRVFHKG  RSAL..VLQY  LRVPLVDRAT  CLRSTKFT..  .IYNNMFC    AGF...H.EG
FactorX      LKTP.....I  TFRMNVAPAC  LPERDWAEST  LMTQK.TGIV  SGFGRTHEKG  RQST..RLKM  LEVPYVDRNS  CKLSSSFI..  .ITQNMFC    AGY...D.TK
FactorVII    LHQP.....V  VLTDHVVPLC  LPERTFSERT  LAFVR.FSLV  SGWGQLLDRG  ATAL..ELMV  LNVPRIMTQD  CLQQSRKVGD  SPNITEYMFC  AGY...S.DG
ProteinC     LAQP.....A  TLSQTIVPIC  LPDSGLAERE  LNQAGQETLV  TGWGYHSSRE  KEAK..RNRT  FVLNFIKIPV  VPHNECSEVM  SNMVSENMLC  AGI...L.GD
```

FIG. 3C-1

```
Thrombin     LKKP.....V AFSDYIHPVC LPDRETAAS. LLQAGYKGRV TGWGNLKETW TANV.GKGQP SVLQVVNLPI VERPVCKDST RIRITDNMFC AGYKPDE.GK
Plasmin      LSSP.....A VITDKVIPAC LPS...PNYV VADRT.ECFI TGWGETQGTF GAGL...LKE AQLPVIENKV CN......R YEFLNGRVQS TELCAGHLAG
apolip       LSRP.....A VITDKVMPAC LPS...PDYM VTART.ECYI TGWGETQGTF GTGL...LKE AQLLVIENEV CN........H YKY...... ..ICAEHLAR
MSP          LERS.....V TLNQRVALIC LPP...EWYV VPPGT.KCEI AGWGETKGTG NDTV...LNV AFLNVISNQE CN........I KHRGRV..RE SEMCTEGLLA
HGF          LARP.....A VLDDFVSTID LPN...YGCT IPEKT.SCSV YGWGYTGLIN YDGL...LRV AHLYIMGNEK CS........Q HHRGKVTLNE SEICAGAEKI
Elastase3    LSRS.....A QLGDAVQLAS LPP...AGDI LPNETP.CYI TGWGRL.YTN .GPLPDKLQE ALLPVVDYEH CSRWNWWGSS .........VKK TMVCAG.GD.
ProteaseE    LSRS.....A QLGDAVQLAS LPP...AGDI LPNKTP.CYI TGWGRL.YTN .GPLPDKLQQ ARLPVVDYKH CSRWNWWGST .........VKK TMVCAG.GY.
Elastase     LANP.....V SLTDKIQLAC LPP...AGTI LPNNYP.CYV TGWGRL.QTN .GAVPDVLQQ GRLLVVDYAT CSSSAWWGSS .........VKT SMICAG.GDG
Elastase2B   LANP.....V SLTDKIQLAC LPP...AGTI LPNNYP.CYV TGWGRL.QTN .GAVPDVLQQ GRLLVVDYAT CSSSGWWGST .........VKT NMICAG.GDG
Caldecrin    LAEH.....V ELSDTIQVAC LPE...KDSL LPKDYP.CYV TGWGRL.WTN .GALPDDLKQ GLQPVVDHAT CSRIDWWGFR .........VKK TMVCAG.GDG
Chymotrypsin LATP.....A RFSQTVSAVC LPS...ADDD FPAGTL.CAT TGWGKT.KYN ANKTPDKLQQ AALPLLSNAE CKKS..WGRR .........ITD VMICAG.ASG
Kallikrein2  LQAP.....L NYTEFQKPIC LPS...KGDT STIYT.NCWV TGWGFSKEKG E..IQNILQK VNIPLVTNEE CQ........K RYQDYK.ITQ RMVCAGYKEG
FactorXI     LETT.....V NYTDSQRPIC LPS...KGDR NVIYT.DCWV TGWGYRKLRD K..IQNTLQK AKIPLVTNEE CQ........K RYRGHK.ITH KMICAGYREG
Enteropep    LEFK.....V NYTDYIQPIC LPE...ENQV FPPGR.NCSI AGWGTVVYQG T..TANILQE ADVPLLSNER CQ........Q QMPEYN.ITE NMICAGYEEG
Prostasin    LSRP.....I TFSRYIRPIC LPA...ANAS FPNGL.HCTV TGWGHVAPSV SLLTPKPLQQ LEVPLISRET CNCLYNIDAK PEEPHF.VQE DMVCAGYVEG
Hepsin       LSSP.....L PLTEYIQPVC LPA...AGQA LVDGK.ICTV TGWGNTQYYG QQ..AGVLQE ARVPIISNDV CNGADFYGNQ .........IKP KMFCAGYPEG
Acrosin      ITPP.....I SCGRFIGPGC LPH...FKAG LPRGSQSCWV AGWGYIEEKP RP..SSIIME ARVDLIDLDL CNSTQWYNGR .........VQP TNVCAGYPVG
Tryptase     LEEP.....V NISSRVHTVM LPP...ASET FPPGMP.CWV TGWGDVDNDE PLPPPFPLKQ VKVPIMENHI CDAKYHLGAY TGDDVRIIRD DMLCAGNSQ.
FactorXII    LQEDADGSCA LLSPYVQPVC LPS...GAAR PSETT.LCQV AGWGH.LCQV CSAPDVHGSS ILPGMLCAGF LE.GGT.... ..........
Hepatocyteact LKKKGD.RCA TRSQFVQPIC LPE...PGST FPAGH.KCQI AGWGH.LDEN VSGYSSSLRE ALVPLVADHK CSSPEVYGAD ISPNMLCAGY FD.CKS....
t-PA         LKSD.SSRCA QESSVVRTVC LPP...ADLQ LPDWT.ECEL SGYGK.HEAL SPFYSERLKE AHVRLYPSSR CTSQHLLNRT VTDNMLCAGD TR.SGGPQAN
UK           IRSK.EGRCA QPSRTIQTIC LPS...MYND PQFGT.SCEI TGFGK.ENST DYLYPEQLKM TVVKLISHRE CQQPHYYGSE VTTKMLCAAD ......PQWK
FactorI      MKKDGNKKDC ELPRSI.PAC VFW...SPYL FQPND.TCIV SGWGR.EKDN ERVFS..LQW GEVKLISN.. .CSKFYGNRF YEKEMECAGT YD.GS.....
```

FIG. 3C-2

```
         251       *******                                                          330
PS133      GKDSCQGDSG GPLVCN..QS.. .....LQGI ISWG.QDPCA ITRKPGVYTK V.CKYVDWIQ ETMKNN----- -----------
C1s        GMDSCKGDSG GAFAVQDPN. DKTKFYAAGL VSWGPQCGT. Y.....GLYTR V.KNYVDWIM KIMQENSTPR ED---------
C1r        KQDACQGDSG GVFAVRDPN. .TDRWVATGI VSWGIGCSRG Y.....GFYTK V.LNYVDWIK KEMEEED--- -----------
Myeloblastin KAGICFGDSG GPLICD..GI .......IQGI DSFVI.WGCA TRLFPDFFTR VAL.YVDWIR STLRRVEAKG RP---------
Medullasin QAGVCFGDSG SPLVCN..GL .......IHGI ASFVR.GGCA SGLYPDAFAP VAQ.FVNWID SIIQRSEDNP CPHPRDPDPA
Azurocidin RGGICNGDGG TPLVCE..GL .......AHGV ASFSL.GPCG RG..PDFFTR VAL.FRDWID GVLNNPGPGP A----------
Stratum    KKNACNGDSG GPLVCR..GT .......LQGL VSWG.TFPCG QPNDPGVYTQ V.CKFTKWIN DIMKKHR--- -----------
Trypsin2   GKDSCQGDSG GPVVSN..GE .......LQGI VSWG.Y.GCA QKNRPGVYTK V.YNYVDWIK DTIAANS--- -----------
Trypsin3   GKDSCQRDSG GPVVCN..GQ .......LQGV VSWG.H.GCA WKNRPGVYTK V.YNYVDWIK DTIAANS--- -----------
Trypsin1   GKDSCQGDSG GPVVCN..GQ .......LQGV VSWG.D.GCA QKNKPGVYTK V.YNYVKWIK NTIAANS--- -----------
Kallikrein3 GKDTCGGDSG GPLVCN..GV .......LQGI TSWG.PEPCA LPEKPAVYTK V.VHYRKWIK DTIAANP--- -----------
PSA        GKSTCSGDSG GPLVCN..GV .......LQGI TSWG.SEPCA LPERPSLYTK V.VHYRKWIK DTIVANP--- -----------
Kallikrein4 GKDTCVGDSG GPLMCD..GV .......LQGV TSWG.YVPCG TPNKPSVAVR V.LSYVKWIE DTIAENS--- -----------
GranzymeB  KKTSFKGDSG GPLVCNK..V .......AQGI VSYGRN.... NGMPPRACTK VS.SFVHWIK KIMKRY---- -----------
GranzymeH  TQTGFKGDSG GPLVCKD..V .......AQGI LSYGNK.... KGTPPGVYIK VS.HFLPWIK RTMKRL---- -----------
Cathepsing RKAAFKGDSG GPLLCNN..V .......AHGI VSYGKS.... SGVPPEVFTR VS.SFLPWIR TTMRSFKLLD QMETPL-----
Chymase    TKSAFKGDSG GPLLCAG..V .......AQGI VSYGRS.... DAKPPAVFTR IS.HYRPWIN QILQAN---- -----------
FactorD    DS..CKGDSG GPLVC..GGV .......LEGV VTSG.SRVCG NRKKPGIYTR VA.SYAAWID SVLA------ -----------
Metase     DQAPCKGDSG GPLVCGKGRV ......LAGV LSFS.SRVCT DIFKPPVATA VA.PYVSWIR KVTGRSA--- -----------
Hanuka     GRDSCNGDSG GPLLCE..GV ......FRGV TSFGLENKCG DPRGPGVYIL LSKKHLNWII MTIKGAV--- -----------
Rafactor   GKDACSGDSG GPMVTLNRE. .RGQWYLVGT VSWGD..DCG KKDRYGVYSY IH.HNKDWIQ RVTGVRN--- -----------
FactorIX   GRDSCQGDSG GPHV..TEV. .EGTSFLTGI ISWGE..ECA MKGKYGIYTK VS.RYVNWIK EKTKLT---- -----------
FactorX    QEDACQGDSG GPHV..TRF. .KDTYFVTGI VSWGE..GCA RKGKYGIYTK VT.AFLKWID RSMKTRGLPK AKSHAPEVIT
FactorVII  SKDSCKGDSG GPHA..THY. .RGTWYLTGI VSWGQ..GCA TVGHFGVYTR VS.QYIEWLQ KLMRSEPRPG VLLRAPFP---
ProteinC   RQDACEGDSG GPMV..ASF. .HGTWFLVGL VSWGE..GCG LLHNYGVYTK VS.RYLDWIH GHIRDKEAPQ KSWAP------
```

FIG. 3D-1

```
Thrombin      RGDACEGDSG GPFVMKSPF.  .NNRWYQMGI VSWGE..GCD RDGKYGFYTH VF.RLKKWIQ KVIDQFGE--  ----------
Plasmin       GTDSCQGDSG GPLVC....F  EKDKYILQGV TSMG..LGCA RPNKPGVYVR VS.RFVTWIE GVMRNN----  ----------
apolip        GTDSCQGDSG GPLVC....F  EKDKYILQGV TSMG..LGCA RPNKPGVYAR VS.RFVTWIE GMMRNN----  ----------
MSP           PVGACEGDYG GPLAC....F  THNCWVLEGI IIPN..RVCA RSRWPAVFTR VS.VFVDWIH KVMRLG----  ----------
HGF           GSGPCEGDYG GPLVC....E  QHKMRMVLGV IVPG..RGCA IPNRPGIFVR VA.YYAKWIH KIILTYKVPQ  S---------
Elastase3     IRSGCNGDSG GPLNCP...T  EDGGWQVHGV TSFVSAFGCN TRRKPTVFTR VS.AFIDWIE ETIASH----  ----------
ProteaseE     IRSGCNGDSG GPLNCP...T  EDGGWQVHGV TSFVSGFGCN FIWKPTVFTR VS.AFIDWIE ETIASH----  ----------
Elastase      VISSCNGDSG GPLNCQ...A  SDGRWQVHGI VSFGSRLGCN YYHKPSVFTR VS.NYIDWIN SVIANN----  ----------
Elastase2B    VICTCNGDSG GPLNCQ...A  SDGRWEVHGI GSLTSVLGCN YYYKPSIFTR VS.NYNDWIN SVIANN----  ----------
Caldecrin     VISACNGDSG GPLNCQ...L  ENGSWEVFGI VSFGSRRGCN TRKKPVVYTR VS.AYIDWIN EKMQL-----  ----------
Chymotrypsin  V.SSCMGDSG GPLVCQ....  KDGAWTLVGI VSWGDT.CS  T.SSPGVYAR VT.KLIPWVQ KILAAN----  ----------
Kallikrein2   GKDACKGDSG GPLVCKHN..  .GMWRLVGI  TSWGE..GCA RREQPGVYTK VA.EYMDWIL EKTQSSDGKA  QMQSPA----
FactorXI      GKDACKGDSG GPLSCKHN..  .EVWHLVGI  TSWGE..GCA QRERPGVYTN VV.EYVDWIL EKTQAV----  ----------
Enteropep     GIDSCQGDSG GPLMCQEN..  .NRWFLAGV  TSFGY..KCA LPNRPGVYAR VS.RFTEWIQ SFLH------  ----------
Prostasin     GKDACQGDSG GPLSCPVE..  .GLWYLTGI  VSWGD..ACG ARNRPGVYTL AS.SYASWIQ SKVTELQPRV  VPQTQESQPD
Hepsin        GIDACQGDSG GPFVCEDSIS  RTPRWRLCGI VSWGT..GCA LAQKPGVYTK VS.DFREWIF QAIKTHSEAS  GMVTQL----
Acrosin       KIDTCQGDSG GPLMCKDS..  KESAYVVVGI TSWGV..GCA LAKRPGIYTA TW.PYLNWIA SKIGSNA---  ----------
Tryptase      .RDSCKGDSG GPLVCKVN..  .GTWLQAGV  VSWDE..GCA QPNRPGIYTR VT.YYLDWIH HYVPKKP---  ----------
FactorXII     ..DACQGDSG GPLVCEDQAA  ERRLT.LQGI ISWGS..GCG RLHKPGVYTR VA.YYLAWIR EHTVS-----  ----------
Hepatocyteact ..DACQGDSG GPLACEKNGV  ...AY.LYGI ISWGD..GCG RLHKPGVYTR VA.NYVDWIN DRIRPPRRLV  APS-------
t-PA          LHDACQGDSG GPLVCLNDG.  .RMT.LVGI  ISWGL..GCG QKDVPGVYTK VT.NYLDWIR DNMRP-----  ----------
UK            T.DSCQGDSG GPLVCSLQG.  .RMT.LTGI  VSWGR..GCA LKDKPGVYTK VS.HFLPWIR SHTKEENGLA  L---------
FactorI       .IDACKGDSG GPLVCMD..A  NNVTY.VWGV VSWGE..NCG KPEFPGFYTK VA.NYFDWIS YHVGRPFISQ  YNV-------
```

FIG. 3D-2

SERINE PROTEASE REAGENTS AND METHODS USEFUL FOR DETECTING AND TREATING DISEASES OF THE PROSTATE

BACKGROUND OF THE INVENTION

The invention relates generally to detecting diseases of the prostate, and more particularly, relates to reagents such as polynucleotide sequences and the polypeptide sequences encoded thereby, as well as methods which utilize these sequences, which are useful for detecting, diagnosing, staging, monitoring, prognosticating, preventing or treating, or determining predisposition to diseases or conditions of the prostate such as prostate cancer. One polypeptide of the present invention is a serine protease.

Prostate cancer is the most common form of cancer occurring in males in the United States, with projections of 334,500 new cases diagnosed and 41,800 related deaths predicted to occur during 1997 (American Cancer Society). Prostate cancer also has shown the largest increase in incidence as compared to other types of cancer, increasing 142% from 1992 to 1996.

Procedures used for detecting, diagnosing, staging, monitoring, prognosticating, preventing or treating, or determining predisposition to diseases or conditions of the prostate such as prostate cancer are of critical importance to the outcome of the patient. For example, patients diagnosed with localized prostate cancer have greater than a 90% five-year survival rate compared to a rate of 25 to 31% for patients diagnosed with distant metastasis. (American Cancer Society statistics). A diagnostic procedure for early detection of prostate cancer should, therefore, specifically detect this disease and be capable of detecting the presence of prostate cancer before symptoms appear.

Such procedures could include assays based upon the appearance of various disease markers in test samples such as blood, plasma, serum, or urine obtained by minimally invasive procedures which are detectable by immunological methods. These procedures would provide information to aid the physician in managing the patient with disease of the prostate and at low cost to the patient. Markers such as the prostate specific antigen (PSA) exist and are used clinically for screening patients for prostate cancer. Elevated levels of PSA protein in serum can be used as a marker in the early detection of prostate cancer in asymptomatic men. G. E. Hanks, et al., In: *Cancer: Principles and Practice of Oncology*, Vol. 1, Fourth Edition, pp. 1073–1113, Philadelphia, Pa. J.B. Lippincott Co. (1993.). PSA normally is secreted by the prostate at high levels into the seminal fluid, but is present in very low levels in the blood of men with normal prostates. However, in patients with diseases of the prostate including benign prostatic hyperplasia (BPH) and adenocarcinoma of the prostate, the level of PSA can be markedly elevated in the blood and thus be useful as an indicator of prostate disease. PSA, however, cannot differentiate between BPH and prostate cancer, which reduces its specificity as a marker for prostate cancer. M. K. Schwartz, et al., In: *Cancer: Principles and Practice of Oncology*, Vol. 1, Fourth Edition, pp. 531–542, Philadelphia, Pa. J.B. Lippincott Co. 1993. New markers which are more specific for prostate cancer thus would be beneficial in the initial detection of this disease.

A critical step in managing patients with prostate cancer is the presurgical staging of the cancer to provide prognostic value and criteria for designing optimal therapy. Improved procedures for accurately staging prostate cancer prior to surgery are needed. One study demonstrated that current methods of staging prostate cancer prior to surgery were incorrect approximately fifty percent (50%) of the time. F. Labrie, et al., *Urology* 44 (Symposium Issue): 29–37 (1994). Prostate cancer management also could be improved by utilizing new markers found in an inappropriate body compartment. Such markers could be MRNA or protein markers expressed by cells originating from the primary prostate tumor but residing in blood, bone marrow or lymph nodes and could be sensitive indicators for metastasis to these distal organs. For example, in patients with metastatic prostate cancer, PSA protein has been detected by immunohistochemical techniques in bone marrow, and PSA mRNA has been detected by RT-PCR in cells of blood, lymph nodes and bone marrow. K. Pantel, et al., *Onkologie* 18: 394–401 (1995).

New markers which could predict the biologic behavior of early prostate cancers would also be of significant value. Early prostate cancers that threaten or will threaten the life of the patient are more clinically important than those that do not or will not be a threat. G. E. Hanks, supra. A need therefore exists for new markers which can differentiate between the clinically important and unimportant prostate cancers. Such markers would allow the clinician to accurately identify and effectively treat early cancers localized to the prostate which could otherwise metastasize and kill the patient. Further, if one could show that such a marker characteristic of aggressive cancer was absent, the patient could be spared expensive and non-beneficial treatment.

It also would be beneficial to find a prostate associated marker which is more sensitive in detecting recurrence of prostate cancer than PSA and which is not affected by androgens. To date, PSA has proven to be the most sensitive marker for detecting recurrent disease. However, in some cases tumor progression occurs without PSA elevation due to hormonal therapy utilized for treating the cancer. Although the decrease in androgen results in a concomitant decrease in PSA, it does not necessarily reflect a decrease in tumor metastasis. This complication is the result of androgen-stimulated PSA expression. Part of the decline in PSA observed after androgen ablation is due not to tumor cell death but to diminished PSA expression. G. E. Hanks, supra.

PSA is a member of the human kallikrein gene family which is a family of serine proteases. A serine protease is a class of protein whose function is to accelerate proteolysis of a substrate protein. Proteolytic processes are thought to be the critical point in tumor invasion and metastasis, and are performed mainly by matrix metalloproteinases (MMPs) and serine proteases or proteinases. In some cases, apoptosis, or programmed cell death, may be prevented by serine protease inhibitors. Suzuki et al., *Exp. Cell Res.* 233 (1):48–55 (1997).

It therefore would be advantageous to provide specific methods and reagents for detecting, diagnosing, staging, monitoring, prognosticating, preventing or treating, or determining predisposition to diseases and conditions of the prostate, or to indicate possible predisposition to these conditions. Such methods would include assaying a test sample for products of a gene which are overexpressed in prostate diseases and conditions such as cancer. Such methods may also include assaying a test sample for products of a gene alteration associated with prostate disease or condition. Such methods may further include assaying a test sample for products of a gene whose distribution among the various tissues and compartments of the body have been altered by a prostate-associated disease or condition such as cancer. Useful reagents include polynucleotides, or fragments thereof, which may be used in diagnostic methods such as reverse transcriptase-polymerase chain reaction (RT-PCR), PCR, or hybridization assays of mRNA extracted from biopsied tissue, blood or other test samples. Other useful reagents include polypeptides or proteins which are the translation products of such mRNAs, and antibodies directed against these polypeptides or proteins. Drug treatment or gene therapy for diseases or conditions of the prostate can then be based on these identified gene sequences or their expressed proteins and efficacy of any particular therapy can be monitored. Furthermore, it would be advantageous to have available alternative, non-surgical diagnostic methods capable of detecting early stage prostate disease such as cancer.

SUMMARY OF THE INVENTION

The present invention provides a method of detecting a target PS133 polynucleotide in a test sample which comprises contacting the test sample with at least one PS133-specific polynucleotide and detecting the presence of the target PS133 polynucleotide in the test sample. The PS133-specific polynucleotide has at least 50% identity with a polynucleotide selected from the group consisting of SEQUENCE ID NOS 1–8, and fragments or complements thereof. Also, the PS133-specific polynucleotide may be attached to a solid phase prior to performing the method.

The present invention also provides a method for detecting PS133 mRNA in a test sample, which comprises performing reverse transcription (RT) with at least one primer in order to produce cDNA, amplifying the cDNA so obtained using PS133 oligonucleotides as sense and anti-sense primers to obtain PS133 amplicon, and detecting the presence of the PS133 amplicon as an indication of the presence of PS133 MRNA in the test sample, wherein the PS133 oligonucleotides have at least 50% identity to a sequence selected from the group consisting of SEQUENCE ID NOS 1–8, and fragments or complements thereof. Amplification can be performed by the polymerase chain reaction. Also, the test sample can be reacted with a solid phase prior to performing the method, prior to amplification or prior to detection. This reaction can be a direct or an indirect reaction. Further, the detection step can comprise utilizing a detectable label capable of generating a measurable signal. The detectable label can be attached to a solid phase.

The present invention further provides a method of detecting a target PS133 polynucleotide in a test sample suspected of containing target PS133 polynucleotides, which comprises (a) contacting the test sample with at least one PS133 oligonucleotide as a sense primer and at least one PS133 oligonucleotide as an anti-sense primer, and amplifying same to obtain a first stage reaction product; (b) contacting the first stage reaction product with at least one other PS133 oligonucleotide to obtain a second stage reaction product, with the proviso that the other PS133 oligonucleotide is located 3' to the PS133 oligonucleotides utilized in step (a) and is complementary to the first stage reaction product; and (c) detecting the second stage reaction product as an indication of the presence of a target PS133 polynucleotide in the test sample. The PS133 oligonucleotides selected as reagents in the method have at least 50% identity to a sequence selected from the group consisting of SEQUENCE ID NOS 1–8, and fragments or complements thereof. Amplification may be performed by the polymerase chain reaction. The test sample can be reacted either directly or indirectly with a solid phase prior to performing the method, or prior to amplification, or prior to detection. The detection step also comprises utilizing a detectable label capable of generating a measurable signal; further, the detectable label can be attached to a solid phase. Test kits useful for detecting target PS133 polynucleotides in a test sample are also provided which comprise a container containing at least one PS133-specific polynucleotide selected from the group consisting of SEQUENCE ID NOS 1–8, and fragments or complements thereof. These test kits further comprise containers with tools useful for collecting test samples (such as, for example, blood, urine, saliva and stool). Such tools include lancets and absorbent paper or cloth for collecting and stabilizing blood; swabs for collecting and stabilizing saliva; and cups for collecting and stabilizing urine or stool samples. Collection materials, such as papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens.

The present invention provides a purified polynucleotide or fragment thereof derived from a PS133 gene. The purified polynucleotide is capable of selectively hybridizing to the nucleic acid of the PS133 gene, or a complement thereof. The polynucleotide has at least 50% identity to a polynucleotide selected from the group consisting of SEQUENCE ID NOS 1–5, SEQUENCE ID NO 8, and fragments or complements thereof, or at least 50% identity with SEQUENCE ID NO 7. Further, the purified polynucleotide can be produced by recombinant and/or synthetic techniques. The purified recombinant polynucleotide can be contained within a recombinant vector. The invention further comprises a host cell transfected with said vector.

The present invention further provides a recombinant expression system comprising a nucleic acid sequence that includes an open reading frame derived from PS133. The nucleic acid sequence has at least 50% identity with a sequence selected from the group consisting of SEQUENCE ID NOS 1–8, and fragments or complements thereof. The nucleic acid sequence is operably linked to a control sequence compatible with a desired host. Also provided is a cell transfected with this recombinant expression system.

The present invention also provides a polypeptide encoded by PS133. The polypeptide can be produced by recombinant technology, provided in purified form, or produced by synthetic techniques. The polypeptide comprises an amino acid sequence which has at least 50% identity with an amino acid sequence selected from the group consisting of SEQUENCE ID NO 24, SEQUENCE ID NO 25, SEQUENCE ID NO 26, and SEQUENCE ID NO 27, or at least 80% identity with a fragment of SEQUENCE ID NO 24 comprising at least 17 amino acid residues. The polypeptide shares significant homology with catalytically functional sites of members of the human serine protease family of molecules and is thus considered herein to be a serine protease.

Also provided is an antibody which specifically binds to at least one PS133 epitope. The antibody can be a polyclonal or monoclonal antibody. The epitope is derived from an amino acid sequence selected from the group consisting of SEQUENCE ID NO 24, SEQUENCE ID NO 25, SEQUENCE ID NO 26, SEQUENCE ID NO 27, and fragments thereof. Assay kits for determining the presence of PS133 antigen or anti-PS133 antibody in a test sample are also included. In one embodiment, the assay kits comprise a container containing at least one PS133 polypeptide having at least 50% identity to an amino acid sequence selected from the group consisting of SEQUENCE ID NO 24, SEQUENCE ID NO 25, SEQUENCE ID NO 26, SEQUENCE ID NO 27, and fragments thereof. Further, the test kit can comprise a container with tools useful for collecting test samples (such as blood, urine, saliva and stool). Such tools include lancets and absorbent paper or cloth for collecting and stabilizing blood; swabs for collecting and stabilizing saliva; and cups for collecting and stabilizing urine or stool samples. Collection materials such as, papers, cloths, swabs, cups and the like, may optionally be treated to avoid denaturation or irreversible adsorption of the sample. These collection materials also may be treated with or contain preservatives, stabilizers or antimicrobial agents to help maintain the integrity of the specimens. Also, the polypeptide can be attached to a solid phase.

Another assay kit for determining the presence of PS133 antigen or anti-PS133 antibody in a test sample comprises a container containing an antibody which specifically binds to a PS133 antigen, wherein the PS133 antigen comprises at least one PS133-encoded epitope. The PS133 antigen has at least about 60% sequence similarity to a sequence of a PS133-encoded antigen selected from the group consisting of SEQUENCE ID NO 24, SEQUENCE ID NO 25, SEQUENCE ID NO 26, SEQUENCE ID NO 27, and fragments thereof. These test kits can further comprise containers with tools useful for collecting test samples (such as blood, urine, saliva and stool). Such tools include lancets and absorbent paper or cloth for collecting and stabilizing blood; swabs for collecting and stabilizing saliva; cups for collecting urine or stool samples. Collection materials, papers, cloths, swabs, cups and the like, may optionally be treated to avoid denaturation or irreversible adsorption of the sample. These collection materials also may be treated with, or contain, preservatives, stabilizers or antimicrobial agents to help maintain the integrity of the specimens. The antibody can be attached to a solid phase.

A method for producing a polypeptide which contains at least one epitope of PS133 is provided, which method comprises incubating host cells transfected with an expression vector. This vector comprises a polynucleotide sequence encoding a polypeptide, wherein the polypeptide comprises an amino acid sequence having at least 50% identity to a PS133 amino acid sequence selected from the group consisting of SEQUENCE ID NO 24, SEQUENCE ID NO 25, SEQUENCE ID NO 26, SEQUENCE ID NO 27, and fragments thereof.

A method for detecting PS133 antigen in a test sample suspected of containing PS133 antigen also is provided. The method comprises contacting the test sample with an antibody or fragment thereof which specifically binds to at least one epitope of a PS133 antigen, for a time and under conditions sufficient for the formation of antibody/antigen complexes; and detecting the presence of such complexes containing the antibody as an indication of the presence of PS133 antigen in the test sample. The antibody can be attached to a solid phase and be either a monoclonal or polyclonal antibody. Furthermore, the antibody specifically binds to at least one PS133 antigen selected from the group consisting of SEQUENCE ID NO 24, SEQUENCE ID NO 25, SEQUENCE ID NO 26, SEQUENCE ID NO 27, and fragments thereof.

Another method is provided which detects antibodies which specifically bind to PS133 antigen in a test sample suspected of containing these antibodies. The method comprises contacting the test sample with a polypeptide which contains at least one PS133 epitope, wherein the PS133 epitope comprises an amino acid sequence having at least 50% identity with an amino acid sequence encoded by a PS133 polynucleotide, or a fragment thereof. Contacting is carried out for a time and under conditions sufficient to allow antigen/antibody complexes to form. The method further entails detecting complexes which contain the polypeptide. The polypeptide can be attached to a solid phase. Further, the polypeptide can be a recombinant protein or a synthetic peptide having at least 50% identity to an amino acid sequence selected from the group consisting of SEQUENCE ID NO 24, SEQUENCE ID NO 25, SEQUENCE ID NO 26, SEQUENCE ID NO 27, and fragments thereof.

The present invention provides a cell transfected with a PS133 nucleic acid sequence that encodes at least one epitope of a PS133 antigen, or fragment thereof. The nucleic acid sequence is selected from the group consisting of SEQUENCE ID NOS 1–8, and fragments or complements thereof.

A method for producing antibodies to PS133 antigen also is provided, which method comprises administering to an individual an isolated immunogenic polypeptide or fragment thereof, wherein the isolated immunogenic polypeptide comprises at least one PS133 epitope in an amount sufficient to produce an immune response. The isolated, immunogenic polypeptide comprises an amino acid sequence selected from the group consisting of SEQUENCE ID NO 24, SEQUENCE ID NO 25, SEQUENCE ID NO 26, SEQUENCE ID NO 27, and fragments thereof.

Another method for producing antibodies which specifically bind to PS133 antigen is disclosed, which method comprises administering to a mammal a plasmid comprising a nucleic acid sequence which encodes at least one PS133 epitope derived from an amino acid sequence selected from the group consisting of SEQUENCE ID NO 24, SEQUENCE ID NO 25, SEQUENCE ID NO 26, SEQUENCE ID NO 27, and fragments thereof.

Also provided is a composition of matter that comprises a PS133 polynucleotide of at least about 10–12 nucleotides having at least 50% identity to a polynucleotide selected from the group consisting of SEQUENCE ID NOS 1–5, SEQUENCE ID NO 8, and fragments or complements thereof, or at least 50% identity with SEQUENCE ID NO 7. The PS133 polynucleotide encodes an amino acid sequence having at least one PS133 epitope. Another composition of matter provided by the present invention comprises a polypeptide with at least one PS133 epitope of about 8–10 amino acids. The polypeptide comprises an amino acid sequence having at least 50% identity with an amino acid sequence selected from the group consisting of SEQUENCE ID NO 24, SEQUENCE ID NO 25, SEQUENCE ID NO 26, and SEQUENCE ID NO 27, or at least 80% identity with a fragment of SEQUENCE ID NO 24 comprising at least 17 amino acid residues. Also provided is a gene or fragment thereof coding for a PS133 polypeptide which has at least 50% identity to SEQUENCE ID NO 24, and a gene or a fragment thereof comprising DNA having at least 50% identity to SEQUENCE ID NO 7 or SEQUENCE ID NO 8.

A therapeutic compound (pharmaceutical composition) is provided which is useful for treating an individual with a disease or condition associated with PS133. The therapeutic compound may be an antagonist, an inhibitor or an agonist of the PS133 polypeptide, gene or MRNA. The compound may be a peptide, antibody or nucleic acid directed to act either synergistically or antagonistically with the PS133 polypeptide, gene or mRNA. The compound may also be mixed with a carrier or diluent to stabilize the compound or to facilitate administration of the compound to an individual with a disease or condition associated with PS133.

A method is also provided for treating an individual with a disease or condition associated with PS133. The method comprises administering a therapeutic compound to an individual by a suitable route such as orally or parenterally, e.g. rectal, transdermal, depot, subcutaneous, intravenous, intramuscular or intranasal. The route of administration is, preferably, such that the compound will be available systemically within the individual.

A method is also provided of discovering an inhibitor, antagonist, or agonist of PS133. The method comprises screening peptides, antibodies or oligonucleotides for the ability to inhibit, eliminate or enhance the proteolytic activity of PS133 polypeptide in an assay utilizing a detectably labeled proteolytic substrate.

BRIEF DESCRIPTION OF THE DRAWINGS

FIGS. 1A–1B show the nucleotide alignment of clones 828846 (SEQUENCE ID NO 1), 2346388 (SEQUENCE ID NO 2), 2531505 (SEQUENCE ID NO 3), 1725220 (SEQUENCE ID NO 4), 1856238 (SEQUENCE ID NO 5), g1367041 (SEQUENCE ID NO 6), and the consensus sequence (SEQUENCE ID NO 7) derived therefrom.

FIGS. 3A–3D show the PS133 polypeptide, SEQUENCE ID NO 24, aligned with the amino acid sequence of 47 known human serine proteases or serine protease-like proteins, SEQUENCE ID NOS 28–74. The functional motifs present in all catalytically functional proteases are marked with an "*".

DETAILED DESCRIPTION OF THE INVENTION

Figure 2:
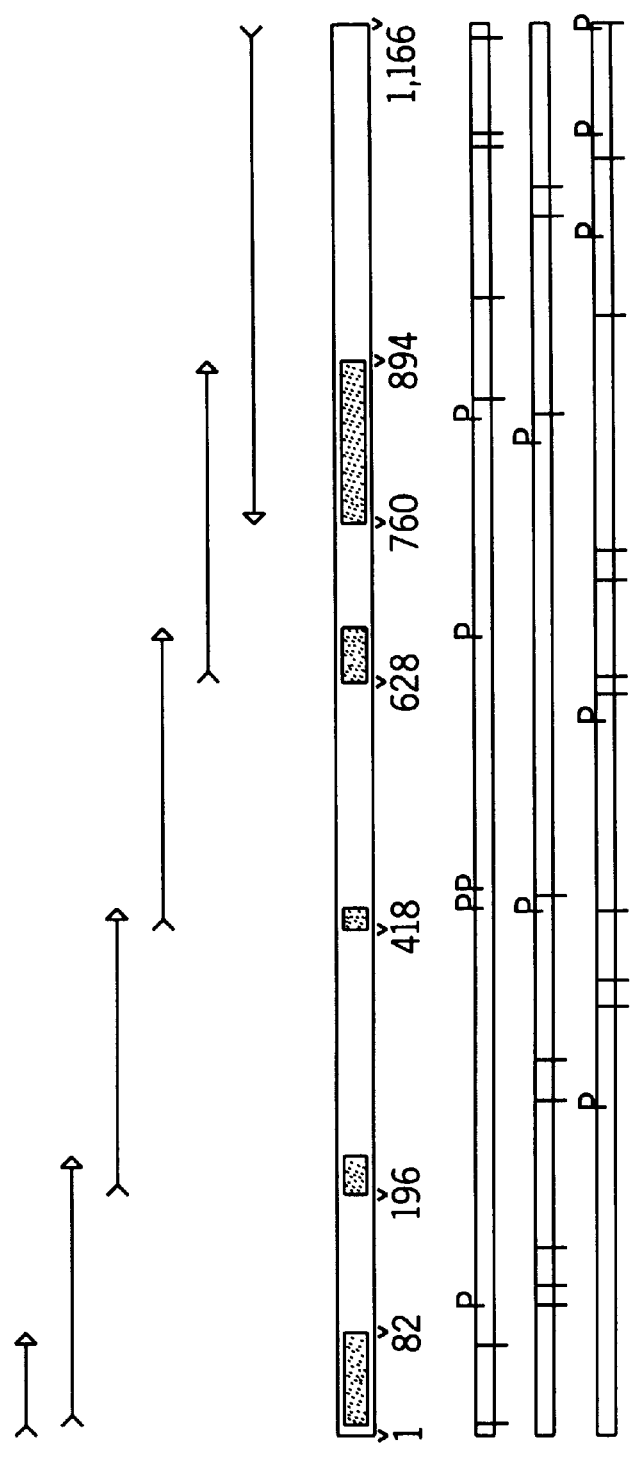
FIG. 2 shows the contig map depicting the formation of the consensus nucleotide sequence (SEQUENCE ID NO 7) from the nucleotide alignment of overlapping clones 828846 (SEQUENCE ID NO 1), 2346388 (SEQUENCE ID NO 2), 2531505 (SEQUENCE ID NO 3), 1725220 (SEQUENCE ID NO 4), 1856238 (SEQUENCE ID NO 5), and g1367041 (SEQUENCE ID NO 6).

The present invention provides a gene or a fragment thereof which codes for a PS133 polypeptide having at least about 50% identity to SEQUENCE ID NO 24. The present invention further encompasses a PS133 gene or a fragment thereof comprising DNA which has at least about 50% identity to SEQUENCE ID NO 7 or SEQUENCE ID NO 8. The present invention also provides a novel serine protease. Differentially expressed levels of serine proteases between normal and diseased prostate tissues can be used as a diagnostic and/or prognostic marker for prostate disease, especially prostate cancer. In addition, serine protease genes, mRNAs and proteins are targets for the design and use of therapeutic treatment.

The present invention provides methods for assaying a test sample for products of a prostate tissue gene designated as PS133, which comprises making cDNA from mRNA in the test sample, and detecting the cDNA as an indication of the presence of prostate tissue gene PS133. The method may include an amplification step, wherein one or more portions of the MRNA from PS133 corresponding to the gene or fragments thereof, is amplified. Methods also are provided for assaying for the translation products of PS133. Test samples which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA; or as probes to determine the presence of certain mRNA sequences in test samples. Also disclosed are nucleic acid sequences which permit the production of encoded polypeptide sequences which are useful as standards or reagents in diagnostic immunoassays, as targets for pharmaceutical screening assays and/or as components or as target sites for various therapies. Monoclonal and polyclonal antibodies directed against at least one epitope contained within these polypeptide sequences are useful as delivery agents for therapeutic agents as well as for diagnostic tests and for screening for diseases or conditions associated with PS133, especially prostate cancer. Isolation of sequences of other portions of the gene of interest can be accomplished utilizing probes or PCR primers derived from these nucleic acid sequences. This allows additional probes of the mRNA or cDNA of interest to be established, as well as corresponding encoded polypeptide sequences. These additional molecules are useful in detecting, diagnosing, staging, monitoring, prognosticating, preventing or treating, or determining the predisposition to, diseases and conditions of the prostate such as prostate cancer, characterized by PS133, as disclosed herein.

Techniques for determining amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity". Two or more amino acid sequences likewise can be compared by determining their "percent identity." The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

The compositions and methods described herein will enable the identification of certain markers as indicative of a prostate tissue disease or condition; the information obtained therefrom will aid in the detecting, diagnosing, staging, monitoring, prognosticating, preventing or treating, or determining diseases or conditions associated with PS133, especially prostate cancer. Test methods include, for example, probe assays which utilize the sequence(s) provided herein and which also may utilize nucleic acid amplification methods such as the polymerase chain reaction (PCR), the ligase chain reaction (LCR), and hybridization. In addition, the nucleotide sequences provided herein contain open reading frames from which an immunogenic epitope may be found. This epitope is believed to be unique to the disease state or condition associated with PS133. It also is thought that the polynucleotides or polypeptides and protein encoded by the PS133 gene are useful as a marker. This marker is either elevated in disease such as prostate cancer, altered in disease such as prostate cancer, or present as a normal protein but appearing in an inappropriate body compartment. The uniqueness of the epitope may be determined by (i) its immunological reactivity and specificity with antibodies directed against proteins and polypeptides encoded by the PS133 gene, and (ii) its nonreactivity with any other tissue markers. Methods for determining immunological reactivity are well-known and include but are not limited to, for example, radioimmunoassay (RIA), enzyme-linked immunosorbent assay (ELISA), hemagglutination (HA), fluorescence polarization immunoassay (FPIA), chemiluminescent immunoassay (CLIA) and others. Several examples of suitable methods are described herein.

Unless otherwise stated, the following terms shall have the following meanings:

A polynucleotide "derived from" or "specific for" a designated sequence refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the designated nucleotide sequence. The sequence may be complementary or identical to a sequence which is unique to a particular polynucleotide sequence as determined by techniques known in the art. Comparisons to sequences in databanks, for example, can be used as a method to determine the uniqueness of a designated sequence. Regions from which sequences may be derived, include but are not limited to, regions encoding specific epitopes, as well as non-translated and/or non-transcribed regions.

The derived polynucleotide will not necessarily be derived physically from the nucleotide sequence of interest under study, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide. In addition, combinations of regions corresponding to that of the designated sequence may be modified in ways known in the art to be consistent with the intended use.

A "fragment" of a specified polynucleotide refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the specified nucleotide sequence.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., PNA as defined hereinbelow) which can be used to identify a specific polynucleotide present in samples bearing the complementary sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence. Thus, a "polypeptide," "protein," or "amino acid" sequence has at least about 50% identity, preferably about 60% identity, more preferably about 75–85% identity, and most preferably about 90–95% or more identity to a PS133 amino acid sequence. Further, the PS133 "polypeptide," "protein," or "amino acid" sequence may have at least about 60% similarity, preferably at least about 75% similarity, more preferably about 85% similarity, and most preferably about 95% or more similarity to a polypeptide or amino acid sequence of PS133. This amino acid sequence can be selected from the group consisting of SEQUENCE ID NO 24, SEQUENCE ID NO 25, SEQUENCE ID NO 26, SEQUENCE ID NO 27, and fragments thereof.

A "recombinant polypeptide," "recombinant protein," or "a polypeptide produced by recombinant techniques," which terms may be used interchangeably herein, describes a polypeptide which by virtue of its origin or manipulation is not associated with all or a portion of the polypeptide with which it is associated in nature and/or is linked to a polypeptide other than that to which it is linked in nature. A recombinant or encoded polypeptide or protein is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, such as methylation or capping and unmodified forms of the polynucleotide. The terms "polynucleotide," "oligomer," "oligonucleotide," and "oligo" are used interchangeably herein.

"A sequence corresponding to a cDNA" means that the sequence contains a polynucleotide sequence that is identical or complementary to a sequence in the designated DNA. The degree (or "percent") of identity or complementarity to the cDNA will be approximately 50% or greater, preferably at least about 70% or greater, and more preferably at least about 90% or greater. The sequence that corresponds to the identified cDNA will be at least about 50 nucleotides in length, preferably at least about 60 nucleotides in length, and more preferably at least about 70 nucleotides in length. The correspondence between the gene or gene fragment of interest and the cDNA can be determined by methods known in the art and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

"Purified polypeptide" or "purified protein" means a polypeptide of interest or fragment thereof which is essentially free of, e.g., contains less than about 50%, preferably less than about 70%, and more preferably less than about 90%, cellular components with which the polypeptide of interest is naturally associated. Methods for purifying polypeptides of interest are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" and "protein" are used interchangeably herein and indicate at least one molecular chain of amino acids linked through covalent and/or non-covalent bonds. The terms do not refer to a specific length of the product. Thus peptides, oligopeptides and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

A "fragment" of a specified polypeptide refers to an amino acid sequence which comprises at least about 3–5 amino acids, more preferably at least about 8–10 amino acids, and even more preferably at least about 17–20 amino acids derived from the specified polypeptide.

"Recombinant host cells," "host cells," "cells," "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to a polynucleotide sequence which is necessary to effect the expression of a coding sequence to which it is ligated. The nature of such control sequences differs depending upon the host organism. In prokaryotes, such control sequences generally include a promoter, a ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequence.

The term "open reading frame" or "ORF" refers to a region of a polynucleotide sequence which encodes a polypeptide. This region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be determined by computer searches of known data banks, such as GenBank, for the polynucleotide sequence which encodes the epitope and by amino acid sequence comparisons with other known proteins.

As used herein, "epitope" means an antigenic determinant of a polypeptide or protein. Conceivably, an epitope can comprise three amino acids in a spatial conformation which is unique to the epitope. Generally, an epitope consists of at least five such amino acids and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of a specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly, by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The term "transfection" refers to the introduction of an exogenous polynucleotide into a prokaryotic or eucaryotic host cell, irrespective of the method used for the introduction. The term "transfection" refers to both stable and transient introduction of the polynucleotide, and encompasses direct uptake of polynucleotides, transformation, transduction, and f-mating. Once introduced into the host cell, the exogenous polynucleotide may be maintained as a non-integrated replicon, for example, a plasmid, or alternatively, may be integrated into the host genome.

"Treatment" refers to prophylaxis and/or therapy.

The term "individual" as used herein refers to vertebrates, particularly members of the mammalian species and includes, but is not limited to, domestic animals, sports animals, primates and humans; more particularly, the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as, antibodies of interest or antigens of interest). These components are well known in the art. A test sample is typically anything suspected of containing a target sequence. Test samples can be prepared using methodologies well known in the art such as by obtaining a specimen from an individual and, if necessary, disrupting any cells contained thereby to release target nucleic acids. These test samples include biological samples which can be tested by the methods of the present invention described herein and include human and animal body fluids such as whole blood, serum, plasma, cerebrospinal fluid, sputum, bronchial washing, bronchial aspirates, urine, lymph fluids and various external secretions of the respiratory, intestinal and genitourinary tracts, tears, saliva, milk, white blood cells, myelomas and the like; biological fluids such as cell culture supernatants; tissue specimens which may be fixed; and cell specimens which may be fixed.

"Purified product" refers to a preparation of the product which has been isolated from the cellular constituents with which the product is normally associated and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with ("attached to") such signal generating compounds as fluorescein, radionucleotides, chemiluminescent compounds and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a polypeptide, an amino acid, a nucleotide target and the like.

"Diseases of the prostate" or "prostate disease," or "condition of the prostate," as used herein, refer to any disease or condition of the prostate including, but not limited to, benign prostatic hyperplasia (BPH), prostatitis, prostatic intraepithelial neoplasia (PIN) and cancer. "Prostate cancer," as used herein, refers to any malignant disease of the prostate including, but not limited to, adenocarcinoma, small cell undifferentiated carcinoma and mucinous (colloid) cancer.

An "Expressed Sequence Tag" or "EST" refers to the partial sequence of a cDNA insert which has been made by reverse transcription of mRNA extracted from a tissue followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules, through chemical or physical means, specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors, and enzymes and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. In addition to being an antibody member of a specific binding pair, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme and the like. An immunoreactive specific binding member can be an antibody, an antigen, or an antibody/antigen complex that is capable of binding either to the polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazole or adamantane.

The various "signal-generating compounds" (labels) contemplated include chromagens, catalysts such as enzymes, luminescent compounds such as fluorescein and rhodarnine, chemiluminescent compounds such as dioxetanes, acridiniums, phenanthridiniums and luminol, radioactive elements and direct visual labels. Examples of enzymes include alkaline phosphatase, horseradish peroxidase, beta-galactosidase and the like. The selection of a particular label is not critical, but it must be capable of producing a signal either by itself or in conjunction with one or more additional substances.

"Solid phases" ("solid supports") are known to those in the art and include the walls of wells of a reaction tray, test tubes, polystyrene beads, magnetic or non-magnetic beads, nitrocellulose strips, membranes, microparticles such as latex particles, sheep (or other animal) red blood cells and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structures generally are preferred, but materials with a gel structure in the hydrated state may be used as well. Such useful solid supports include, but are not limited to, nitrocellulose and nylon. It is contemplated that such porous solid supports described herein preferably are in the form of sheets of thickness from about 0.01 to 0.5 mm, preferably about 0.1 mm. The pore size may vary within wide limits and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

The terms "therapeutically effective dose" and "efficacious dose" of a drug, agent, or compound, are used interchangeably herein to define an amount of a particular drug, agent or compound to be administered to a patient suffering from prostate disease, especially prostate cancer, within the context of a suitable therapeutic regimen that is sufficient to cure, partially arrest, or detectably slow the progression of the disease and its complications.

A "pharmaceutical carrier" or "pharmaceutical diluent" are pharmaceutically-acceptable, non-toxic vehicles commonly used to formulate pharmaceutical compositions for animal or human administration.

A "serine protease," as described herein, is any peptide containing three functional motifs, in the following order and spacing: a His motif (approximately 10–40 amino acid residues from the amino terminus), an Asp motif (approximately 20–75 residues further in from the His motif toward the carboxy terminus), and a Ser motif (approximately 60–140 residues further in from the Asp motif toward the carboxy terminus), each motif being named after the catalytic residue within each active site of the motif.

Reagents

The present invention provides reagents such as polynucleotide sequences derived from a prostate tissue of interest and designated as PS133, polypeptides encoded thereby and antibodies specific for these polypeptides. The present invention also provides reagents such as oligonucleotide fragments derived from the disclosed polynucleotides and nucleic acid sequences complementary to these polynucleotides. The polynucleotides, polypeptides, or antibodies of the present invention may be used to provide information leading to the detecting, diagnosing, staging, monitoring, prognosticating, preventing or treating of, or determining the predisposition to, diseases and conditions of the prostate such as cancer. The sequences disclosed herein represent unique polynucleotides which can be used in assays or for producing a specific profile of gene transcription activity. Such assays are disclosed in European Patent Number 0373203B1 and International Publication No. WO 95/11995, which are hereby incorporated by reference.

Selected PS133-derived polynucleotides can be used in the methods described herein for the detection of normal or altered gene expression. Such methods may employ PS133 polynucleotides or oligonucleotides, fragments or derivatives thereof, or nucleic acid sequences complementary thereto.

The polynucleotides disclosed herein, their complementary sequences, or fragments of either, can be used in assays to detect, amplify or quantify genes, nucleic acids, cDNAs or mRNAs relating to prostate tissue disease and conditions associated therewith. They also can be used to identify an entire or partial coding region of a PS133 polypeptide. They further can be provided in individual containers in the form of a kit for assays, or provided as individual compositions. If provided in a kit for assays, other suitable reagents such as buffers, conjugates and the like may be included.

The polynucleotide may be in the form of RNA or DNA. Polynucleotides in the form of DNA, cDNA, genomic DNA, nucleic acid analogs and synthetic DNA are within the scope of the present invention. The DNA may be double-stranded or single-stranded, and if single stranded, may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and an additional coding sequence such as a leader or secretory sequence or a proprotein sequence, or the coding sequence for the polypeptide (and optionally an additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the polypeptide. The polynucleotides may also encode for a proprotein which is the protein plus additional 5' amino acid residues. A protein having a prosequence is a proprotein and may, in some cases, be an inactive form of the protein. Once the prosequence is cleaved, an active protein remains. Thus, the polynucleotide of the present invention may encode for a protein, or for a protein having a prosequence, or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the polypeptide fused to the marker in the case of a bacterial host, or, for example, the marker sequence may be a hemagglutinin (HA) tag when a mammalian host, e.g. a COS-7 cell line, is used. The HA tag corresponds to an epitope derived from the influenza hemagglutinin protein. See, for example, I. Wilson, et al., Cell 37:767 (1984).

It is contemplated that polynucleotides will be considered to hybridize to the sequences provided herein if there is at least 50%, preferably at least 70%, and more preferably at least 90% identity between the polynucleotide and the sequence.

The present invention also provides an antibody produced by using a purified PS133 polypeptide of which at least a portion of the polypeptide is encoded by a PS133 polynucleotide selected from the polynucleotides provided herein. These antibodies may be used in the methods provided herein for the detection of PS133 antigen in test samples. The presence of PS133 antigen in the test samples is indicative of the presence of a prostate disease or condition. The antibody also may be used for therapeutic purposes, for example, in neutralizing the activity of PS133 polypeptide in conditions associated with altered or abnormal expression.

The present invention further relates to a PS133 polypeptide which has the deduced amino acid sequence as provided herein, as well as fragments, analogs and derivatives of such polypeptide. The polypeptide of the present invention may be a recombinant polypeptide, a natural purified polypeptide or a synthetic polypeptide. The fragment, derivative or analog of the PS133 polypeptide may be one in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are provided preferably in an isolated form and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, e.g., replacement of leucine with isoleucine or threonine with serine. In contrast, variations may include nonconservative changes, e.g., replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison Wis.).

Probes constructed according to the polynucleotide sequences of the present invention can be used in various assay methods to provide various types of analysis. For example, such probes can be used in fluorescent in situ hybridization (FISH) technology to perform chromosomal analysis, and used to identify cancer-specific structural alterations in the chromosomes, such as deletions or translocations that are visible from chromosome spreads or detectable using PCR-generated and/or allele specific oligonucleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in tissue specimens or cells.

This invention also provides teachings as to the production of the polynucleotides and polypeptides provided herein.

Probe Assays

The sequences provided herein may be used to produce probes which can be used in assays for the detection of nucleic acids in test samples. The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multi-gene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al., published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall et al., PCR Methods and Applications 4: 80–84 (1994), which also is incorporated herein by reference.

Other known amplification methods which can be utilized herein include but are not limited to the so-called "NASBA" or "3SR" technique described by J. C. Guatelli et al., PNAS USA 87:1874–1878 (1990) and also described by J. Compton, Nature 350 (No. 6313):91–92 (1991); Q-beta amplification as described in published European Patent Application (EPA) No. 4544610; strand displacement amplification (as described in G. T. Walker et al., Clin. Chem. 42:9–13 [1996]) and European Patent Application No. 684315; and target mediated amplification, as described in International Publication No. WO 93/22461.

Detection of PS133 may be accomplished using any suitable detection method, including those detection methods which are currently well known in the art, as well as detection strategies which may evolve later. Examples of the foregoing presently known detection methods are hereby incorporated herein by reference. See, for example, Caskey et al., U.S. Pat. No. 5,582,989, Gelfand et al., U.S. Pat. No. 5,210,015. Examples of such detection methods include target amplification methods as well as signal amplification technologies. An example of presently known detection methods would include the nucleic acid amplification technologies referred to as PCR, LCR, NASBA, SDA, RCR and TMA. See, for example, Caskey et al., U.S. Pat. No. 5,582,989, Gelfand et al., U.S. Pat. No. 5,210,015. All of the foregoing are hereby incorporated by reference. Detection may also be accomplished using signal amplification such as that disclosed in Snitman et al., U.S. Pat. No. 5,273,882. While the amplification of target or signal is preferred at present, it is contemplated and within the scope of the present invention that ultrasensitive detection methods which do not require amplification can be utilized herein.

Detection, both amplified and non-amplified, may be (combined) carried out using a variety of heterogeneous and homogeneous detection formats. Examples of heterogeneous detection formats are disclosed in Snitman et al., U.S. Pat. No. 5,273,882, Albarella et al. in EP-84114441.9, Urdea et al., U.S. Pat. No. 5,124,246, Ullman et al. U.S. Pat. No. 5,185,243 and Kourilsky et al., U.S. Pat. No. 4,581,333. All of the foregoing are hereby incorporated by reference. Examples of homogeneous detection formats are disclosed in, Caskey et al., U.S. Pat. No. 5,582,989, Gelfand et al., U.S. Pat. No. 5,210,015, which are incorporated herein by reference. Also contemplated and within the scope of the present invention is the use of multiple probes in the hybridization assay, which use improves sensitivity and amplification of the PS133 signal. See, for example, Caskey et al., U.S. Pat. No. 5,582,989, Gelfand et al., U.S. Pat. No. 5,210,015, which are incorporated herein by reference.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method provided herein are labeled with capture and detection labels, wherein probes are labeled with one type of label and primers are labeled with another type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences are cooled, the probe sequences preferentially bind the single stranded amplicon members. This finding is counterintuitive given that the probe sequences generally are selected to be shorter than the primer sequences and therefore have a lower melt temperature than the primers. Accordingly, the melt temperature of the amplicon produced by the primers should also have a higher melt temperature than the probes. Thus, as the mixture cools, the re-formation of the double stranded amplicon would be expected. As previously stated, however, this is not the case. The probes are found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugate's presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well-known amplification reactions that include thermal cycle reaction mixtures, particularly in PCR and gap LCR (GLCR). Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated, they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the target's complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as, for example, deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example, peptide nucleic acids which are disclosed in International Publication No. WO 92/20702; morpholino analogs which are described in U.S. Pat. Nos. 5,185,444, 5,034,506 and 5,142,047; and the like. Depending upon the type of label carried by the probe, the probe is employed to capture or detect the amplicon generated by the amplification reaction. The probe is not involved in amplification of the target sequence and therefore may have to be rendered "non-extendible" in that additional dNTPs cannot be added to the probe. In and of themselves, analogs usually are non-extendible and nucleic acid probes can be rendered non-extendible by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendible.

The ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, primer to probe ratios of, for example, 5:1 and 20:1, are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), DuPont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3' -Amine-ON CPG® (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. Nos. 625,566, filed Dec. 11, 1990 and U.S. Ser. No. 630,908, filed Dec. 20, 1990, which are each incorporated herein by reference, teach methods for labeling probes at their 5' and 3' termini, respectively. International Publication Nos WO 92/10505, published Jun. 25, 1992, and WO 92/11388, published Jul. 9, 1992, teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., *Tet. Letters* 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' and 5' ends.

A capture label is attached to the primers or probes and can be a specific binding member which forms a binding pair with the solid phase reagent's specific binding member. It will be understood that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories, Abbott Park, Ill.).

The primers and probes disclosed herein are useful in typical PCR assays, wherein the test sample is contacted with a pair of primers, amplification is performed, the hybridization probe is added, and detection is performed.

Another method provided by the present invention comprises contacting a test sample with a plurality of polynucleotides, wherein at least one polynucleotide is a PS133 molecule as described herein, hybridizing the test sample with the plurality of polynucleotides and detecting hybridization complexes. Hybridization complexes are identified and quantitated to compile a profile which is indicative of prostate tissue disease, such as prostate cancer. Expressed RNA sequences may further be detected by reverse transcription and amplification of the DNA product by procedures well-known in the art, including polymerase chain reaction (PCR).

Drug Screening and Gene Therapy

The present invention also encompasses the use of gene therapy methods for the introduction of anti-sense PS133 derived molecules, such as polynucleotides or oligonucleotides of the present invention, into patients with conditions associated with abnormal expression of polynucleotides related to a prostate tissue disease or condition, especially prostate cancer. These molecules, including antisense RNA and DNA fragments and ribozymes, are designed to inhibit the translation of PS133-mRNA, and may be used therapeutically in the treatment of conditions associated with altered or abnormal expression of PS133 polynucleotide.

Alternatively, the oligonucleotides described above can be delivered to cells by procedures known in the art such that the anti-sense RNA or DNA may be expressed in vivo to inhibit production of a PS133 polypeptide in the manner described above. Antisense constructs to a PS133 polynucleotide, therefore, reverse the action of PS133 transcripts and may be used for treating prostate tissue disease conditions, such as prostate cancer. These antisense constructs may also be used to treat tumor metastases.

The present invention also provides a method of screening a plurality of compounds for specific binding to PS133 polypeptide(s), or any fragment thereof, to identify at least one compound which specifically binds the PS133 polypeptide. Such a method comprises the steps of providing at least one compound; combining the PS133 polypeptide with each compound under suitable conditions for a time sufficient to allow binding; and detecting the PS133 polypeptide binding to each compound.

The polypeptide or peptide fragment employed in such a test may either be free in solution, affixed to a solid support, borne on a cell surface or located intracellularly. One method of screening utilizes eukaryotic or prokaryotic host cells which are stably transfected with recombinant nucleic acids which can express the polypeptide or peptide fragment. A drug, compound, or any other agent may be screened against such transfected cells in competitive binding assays. For example, the formation of complexes between a polypeptide and the agent being tested can be measured in either viable or fixed cells.

The present invention thus provides methods of screening for drugs, compounds, or any other agent which can be used to treat diseases associated with PS133. These methods comprise contacting the agent with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is used as a measure of the ability of the particular agent to bind to the polypeptide or to interfere with the polypeptide/cell complex.

The present invention also encompasses the use of competitive screening assays in which neutralizing antibodies capable of binding polypeptide specifically compete with a test agent for binding to the polypeptide or fragment thereof. In this manner, the antibodies can be used to detect the presence of any polypeptide in the test sample which shares one or more antigenic determinants with a PS133 polypeptide as provided herein.

Another technique for screening provides high throughput screening for compounds having suitable binding affinity to at least one polypeptide of PS133 disclosed herein. Briefly, large numbers of different small peptide test compounds are synthesized on a solid phase, such as plastic pins or some other surface. The peptide test compounds are reacted with polypeptide and washed. Polypeptide thus bound to the solid phase is detected by methods well-known in the art. Purified polypeptide can also be coated directly onto plates for use in the screening techniques described herein. In addition, non-neutralizing antibodies can be used to capture the polypeptide and immobilize it on the solid support. See, for example, EP 84/03564, published on Sep. 13, 1984, which is incorporated herein by reference.

The goal of rational drug design is to produce structural analogs of biologically active polypeptides of interest or of the small molecules including agonists, antagonists, or inhibitors with which they interact. Such structural analogs can be used to design drugs which are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J. Biochem.* (*Tokyo*) 113 (6):742–746 (1993), incorporated herein by reference.

The present invention is also directed to antagonists and inhibitors of the PS133 polypeptides of the present invention. The antagonists and inhibitors are those which inhibit or eliminate the function of a PS133 polypeptide. Thus, for example, an antagonist may bind to the PS133 polypeptide of SEQUENCE ID NO 24, or fragment thereof, and inhibit or eliminate the function thereof. The antagonist, for example, could be a peptide, antibody or oligonucleotide directed against the PS133 polypeptide of SEQUENCE ID NO 24, or fragment thereof. An example of an inhibitor is a small molecule inhibitor which inactivates the PS133 polypeptide of SEQUENCE ID NO 24 by binding to and occupying a catalytic site, thereby making the catalytic site inaccessible to a substrate and preventing the biological activity of the PS133 polypeptide. Examples of small molecule inhibitors include, but are not limited to, small peptides or peptide-like molecules or non-peptide protease inhibitors. These antagonists and inhibitors may thus be used to treat prostatic disease, such as benign prostatic hypertrophy or prostatic cancer, by preventing a PS133 polypeptide from functioning to catalyze the hydrolysis of its substrate.

It is also conceivable that a clinical condition exists wherein the proteolytic activity of PS133 polypeptide is deficient, leading to an undesired medical situation. In this case, agonists of the PS133 polypeptide are expected to be clinically useful. An agonist is a compound which might bind to an auxiliary site distal from the catalytic site of the prostate protease and serve to activate the enzyme to a higher state of function than in the situation without the agonist compound. In this way, an agonist compound may be used to treat disease resulting from insufficient biological action of the PS133 polypeptide.

Compounds, agents or drugs which serve as antagonists, inhibitors or agonists of PS133 polypeptides may be employed in a composition with a pharmaceutically acceptable carrier, including but not limited to, saline, buffered saline, dextrose, water, glycerol, ethanol and combinations thereof. Administration of protease inhibitors is preferably by oral dose, but may also be intraperitoneal, subcutaneous, intravenous, intratracheal, sublingual, intranasal, rectal, transdermal. A direct application of the antagonists, agonists, or inhibitors, to the diseased prostate gland via injection into or near the prostate may also be employed.

A small molecule drug or compound may function by blocking or otherwise antagonizing the action of a PS133 polypeptide, or may function as an agonist of an interaction between a PS133 polypeptide and a receptor. A therapeutically effective dose of such a drug or compound can be administered to a patient suffering from prostate disease, such as prostate cancer, in the context of a therapeutic regimen that is sufficient to cure, partially arrest, or detectably slow the progression of the disease and its complications. The dosage of the drug or compound may be approximately 0.1–1000 mg per adult human, and more preferably, approximately 1–500 mg per adult human. The route of administration of a small molecule drug or compound against a PS133 polypeptide may be any route which effectively transports the active compound to the appropriate or desired site of action, such as oral or parenteral, e.g. rectal, transdermal, depot, subcutaneous, intravenous, intramuscular or intranasal.

In order to be in a form that can be administered to a patient, one or more of the above-described drugs, agents or compounds (for use in the treatment of PS133-related disease) may be combined with one or more non-toxic pharmaceutically acceptable carriers, diluents or adjuvants; other auxiliary agents if necessary; and, if desired, other active ingredients. Forms suitable for oral use include, but are not limited to, tablets, troches, lozenges, aqueous or oily suspensions, dispersible powders or granules, emulsions, hard or soft capsules, or syrups or elixirs, and may be prepared according to any method known to the art for the manufacture of pharmaceutical compositions. Other compositions for oral administration include spray compositions which may be prepared by known methods and which comprise one or more active compounds. The spray compositions can also contain a suitable propellant.

Pharmaceutical compositions for parenteral administration by injection of a PS133-related drug, agent, or compound, include sterile aqueous or non-aqueous solutions and suspensions or emulsions, in a nontoxic parenterally-acceptable diluent or solvent. These compositions may also include adjuvants such as wetting, preserving, emulsifying and dispersing agents. They may be sterilized by one of several known methods or manufactured in the form of sterile solid compositions which can be dissolved in sterile water or some other sterile injectable medium immediately before use.

Pharmaceutical compositions may also be administered in the form of suppositories for rectal administration. These compositions can be prepared by mixing an appropriate drug, agent or compound with a suitable non-irritating excipient which is solid at ordinary temperatures but liquid at rectal temperatures, and will therefore melt in the rectum to release the therapeutically active ingredient.

Formulations containing PS133 drugs, agents or compounds may be formulated so as to provide quick, sustained, or delayed release of the active ingredient after administration to the patient by employing procedures well known in the art.

Active compounds to PS133 may be suitable for administration to an animal. Such animals include domestic animals, for example livestock, laboratory animals, and household pets, and non-domestic animals such as wildlife. More preferably, the animal is a vertebrate. Most preferably, a drug to PS133 is administered to a mammal. It is especially preferred that the animal is a domestic mammal or a human. The most preferred mammal is a human. For such purposes, a PS133 drug, agent or compound may be administered as a food or feed additive.

The present invention also relates to an assay for identifying the above-mentioned small molecule inhibitors which are specific to a PS133 protease and prevent it from functioning. Either natural protein substrates or synthetic peptides can be used to assess proteolytic activity of the protease molecule, and the ability of inhibitors to prevent this activity provides the basis for a screen to identify a compound that has therapeutic activity in prostatic disorders.

It also is possible to isolate a target-specific antibody selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then can be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which is derivable from the nucleic acid sequence provided herein will provide guidance to those employing computer modeling techniques in place of, or in addition to, x-ray crystallography.

Antibodies specific to a PS133 polypeptide (e.g., anti-PS133 antibodies) further may be used to inhibit the biological action of the polypeptide by binding to the polypeptide. In this manner, the antibodies may be used in therapy, for example, to treat prostate tissue diseases including prostate cancer and its metastases.

Further, such antibodies can detect the presence or absence of a PS133 polypeptide in a test sample and, therefore, are useful as diagnostic markers for the diagnosis of a prostate tissue disease or condition, especially prostate cancer. Such antibodies may also function as a diagnostic marker for prostate tissue disease conditions, such as prostate cancer. The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function. The antagonist, for example, could be an antibody against the polypeptide which eliminates the activity of a PS133 polypeptide by binding a PS133 polypeptide, or in some cases the antagonist may be an oligonucleotide. Examples of small molecule inhibitors include, but are not limited to, small peptides or peptide-like molecules.

The antagonists and inhibitors may be employed as a composition with a pharmaceutically acceptable carrier including, but not limited to, saline, buffered saline, dextrose, water, glycerol, ethanol and combinations thereof. Administration of PS133 polypeptide inhibitors is preferably systemic. The present invention also provides an antibody which inhibits the action of such a polypeptide.

The antibody may be a monoclonal antibody that demonstrates binding specificity for PS133, and functions as a therapeutic agent by blocking or otherwise antagonizing the action of PS133 in diseased prostate cells, such as prostate tumor cells, or may function as an agonist of an interaction between PS133 and a receptor of prostate tumor cells. Such an antibody may be administered in vivo to a patient already suffering from prostate disease, such as prostate cancer, in a therapeutically effective or efficacious dose to cure, partially arrest, or detectably slow the progression of the disease and its complications. The amounts effective for this use will depend upon the severity of the prostate disease, the general state of the patient, and the route of administration and combination with other active agents to prostate disease, such as prostate cancer.

Pharmaceutical compositions containing the monoclonal antibody also can be administered either systemically, by intravenous infusion, or locally, by injection. The composition may include pharmaceutical carriers or diluents. The diluent is selected so as not to affect the biological activity of the composition. In addition, the pharmaceutical composition or formulation may also include other carriers, adjuvants, or nontoxic, nontherapeutic, nonimmunogenic stabilizers and the like.

For the destruction of disease cells, such as prostate tumor cells, it can be advantageous to conjugate the PS133-specific monoclonal antibody to another molecule prior to in vivo administration. For example, the monoclonal antibody can be joined to a cytotoxin, a chemotherapeutic agent, a radioisotope, or other modulator of cellular activity, whereby binding of the monoclonal antibody conjugate to prostate tumor cells will result in tumor cell death. For example, a number of protein toxins are well known in the art including ricin, diphtheria, gelonin, Pseudomonas toxin, and arbrin. Chemotherapeutic agents include, but are not limited to, for example, methotrexate, daunorubicin, and doxorubicin. Radioisotopes include, but are not limited to, yttrium-90, phosphorus-32, lead-212, iodine-131, and palladium-109.

Antisense technology can be used to reduce gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of the PS133 polypeptide. For triple helix, see, for example, Lee et al., *Nuc. Acids Res.* 6:3073 (1979); Cooney et al., *Science* 241:456 (1988); and Dervan et al., *Science* 251:1360 (1991) The antisense RNA oligonucleotide hybridizes to the mRNA in vivo and blocks translation of a mRNA molecule into the PS133 polypeptide. For antisense, see, for example, Okano, *J. Neurochem.* 56:560 (1991); and "Oligodeoxynucleotides as Antisense Inhibitors of Gene Expression", CRC Press, Boca Raton, Fla. (1988). Antisense oligonucleotides act with greater efficacy when modified to contain artificial intemucleotide linkages which render the molecule resistant to nucleolytic cleavage. Such artificial internucleotide linkages include, but are not limited to, methylphosphonate, phosphorothiolate and phosphoroamydate internucleotide linkages.

Administration of an antisense PS133 oligonucleotide to an individual may be orally or by subcutaneous, intramuscular, intraperitoneal, or intravenous injection. A typical injectable composition comprises a pharmaceutically acceptable solvent or diluent, and other suitable, physiologic compounds. For example, the composition may contain an antisense PS133 oligonucleotide and about 10 mg/ml of human serum albumin in a phosphate buffer containing NaCl. Other pharmaceutically acceptable excipients include, non-aqueous or aqueous solutions and non-toxic compositions including salts, preservatives, buffers and the like. The pH and exact concentration of the various components are adjusted according to routine skills in the art.

An antisense PS133 oligonucleotide may also be administered by injection as an oily suspension. Suitable lipophilic solvents or vehicles include fatty oils, synthetic fatty acid esters, or any one of a number of sterols. A preferred sterol is cholesterol. Aqueous injection suspensions may contain substances which increase the viscosity of the suspension and also stabilizers.

An alternative formulation for antisense oligonucleotide administration involves liposomes. Antisense oligonucleotides can be encapsulated within liposomes using standard techniques. A variety of different liposome compositions and methods for synthesis are known to those of skill in the art. In general, the dosage of administered liposome-encapsulated antisense PS133 oligonucleotide will vary depending upon such factors as the patient's age, weight, height, sex, general medical condition and previous history. Dose ranges for particular formulations can be determined by using a suitable animal model.

Recombinant Technology

The present invention provides host cells and expression vectors comprising PS133 polynucleotides of the present invention and methods for the production of the polypeptide (s) they encode. Such methods comprise culturing the host cells under conditions suitable for the expression of the PS133 polynucleotide and recovering the PS133 polypeptide from the cell culture.

The present invention also provides vectors which include PS133 polynucleotides of the present invention, host cells which are genetically engineered with vectors of the present invention and the production of polypeptides of the present invention by recombinant techniques.

Host cells are genetically engineered (transfected, transduced or transformed) with the vectors of this invention which may be cloning vectors or expression vectors. The vector may be in the form of a plasmid, a viral particle, a phage, etc. The engineered host cells can be cultured in conventional nutrient media modified as appropriate for activating promoters, selecting transfected cells, or amplifying PS133 gene(s). The culture conditions, such as temperature, pH and the like, are those previously used with the host cell selected for expression, and will be apparent to the ordinarily skilled artisan.

The polynucleotides of the present invention may be employed for producing a polypeptide by recombinant techniques. Thus, the polynucleotide sequence may be included in any one of a variety of expression vehicles, in particular, vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus and pseudorabies. However, any other plasmid or vector may be used so long as it is replicable and viable in the host.

The appropriate DNA sequence may be inserted into the vector by a variety of procedures. In general, the DNA sequence is inserted into appropriate restriction endonuclease sites by procedures known in the art. Such procedures and others are deemed to be within the scope of those skilled in the art. The DNA sequence in the expression vector is operatively linked to an appropriate expression control sequence(s) (promoter) to direct mRNA synthesis. Representative examples of such promoters include, but are not limited to, the LTR or the SV40 promoter, the *E. coli* lac or trp, the phage lambda P sub L promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain a gene to provide a phenotypic trait for selection of transfected host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transfect an appropriate host to permit the host to express the protein. As representative examples of appropriate hosts, there may be mentioned: bacterial cells, such as *E. coli, Salmonella typhimurium*; Streptomyces sp.; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings provided herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available. The following vectors are provided by way of example. Bacterial: pINCY (Incyte Pharmaceuticals Inc., Palo Alto, Calif.), pSPORT1 (Life Technologies, Gaithersburg, Md.), pQE70, pQE60, pQE-9 (Qiagen) pBs, phagescript, psiX174, pBluescript SK, pBsKS, pNH8a, pNH16a, pNH18a, pNH46a (Stratagene); pTrc99A, pKK223-3, pKK233-3, pDR540, pRIT5 (Pharmacia); Eukaryotic: pWLneo, pSV2cat, pOG44, pXT1, pSG (Stratagene) pSVK3, pBPV, pMSG, pSVL (Pharmacia). However, any other plasmid or vector may be used as long as it is replicable and viable in the host.

Plasmid pINCY is generally identical to the plasmid pSPORT1 (available from Life Technologies, Gaithersburg, Md.) with the exception that it has two modifications in the polylinker (multiple cloning site). These modifications are (1) it lacks a HindIII restriction site and (2) its EcoRI restriction site lies at a different location. pINCY is created from pSPORT1 by cleaving pSPORT1 with both HindIII and EcoRI and replacing the excised fragment of the polylinker with synthetic DNA fragments (SEQUENCE ID NO 9 and SEQUENCE ID NO 10). This replacement may be made in any manner known to those of ordinary skill in the art. For example, the two nucleotide sequences, SEQUENCE ID NO 9 and SEQUENCE ID NO 10, may be generated synthetically with 5' terminal phosphates, mixed together, and then ligated under standard conditions for performing staggered end ligations into the pSPORT1 plasmid cut with HindIII and EcoRI. Suitable host cells (such as *E. coli* DH5 cells) then are transfected with the ligated DNA and recombinant clones are selected for ampicillin resistance. Plasmid DNA then is prepared from individual clones and subjected to restriction enzyme analysis or DNA sequencing in order to confirm the presence of insert sequences in the proper orientation. Other cloning strategies known to the ordinary artisan also may be employed.

Promoter regions can be selected from any desired gene using CAT (chloramphenicol transferase) vectors or other vectors with selectable markers. Two appropriate vectors are pKK232-8 and pCM7. Particular named bacterial promoters include lacd, lacZ, T3, SP6, T7, gpt, lambda P sub R, P sub L and trp. Eukaryotic promoters include cytomegalovirus (CMV) immediate early, herpes simplex virus (HSV) thymidine kinase, early and late SV40, LTRs from retroviruses and mouse metallothionein-I. Selection of the appropriate vector and promoter is well within the level of ordinary skill in the art.

In a further embodiment, the present invention provides host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (L. Davis et al., "Basic Methods in Molecular Biology," 2nd edition, Appleton and Lang, Paramount Publishing, East Norwalk, Conn. (1994)).

The constructs in host cells can be used in a conventional manner to produce the gene product encoded by the recombinant sequence. Alternatively, the polypeptides of the invention can be synthetically produced by conventional peptide synthesizers.

Recombinant proteins can be expressed in mammalian cells, yeast, bacteria, or other cells, under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, (Cold Spring Harbor, N.Y., 1989), which is hereby incorporated by reference.

Transcription of a DNA encoding the polypeptide(s) of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin and adenovirus enhancers.

Generally, recombinant expression vectors will include origins of replication and selectable markers permitting transfection of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), alpha factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transfection include *E. coli, Bacillus subtilis, Salmonella typhimurium* and various species within the genera Pseudomonas, Streptomyces and Staphylococcus, although, others may also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Following transfection of a suitable host and growth of the host to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents. Such methods are well-known to one of ordinary skill in the art.

Various mammalian cell culture systems can also be employed to express recombinant protein. Examples of mammalian expression systems include the COS-7 lines of monkey kidney fibroblasts described by Gluzman, Cell 23:175 (1981), and other cell lines capable of expressing a compatible vector, such as the C127, HEK-293, 3T3, CHO, HeLa and BHK cell lines. Mammalian expression vectors will comprise an origin of replication, a suitable promoter and enhancer and also any necessary ribosome binding sites, polyadenylation sites, splice donor and acceptor sites, transcriptional termination sequences and 5' flanking nontranscribed sequences. DNA sequences derived from the SV40 viral genome, for example, SV40 origin, early promoter, enhancer, splice, and polyadenylation sites may be used to provide the required nontranscribed genetic elements. Representative, useful vectors include pRc/CMV and pcDNA3 (available from Invitrogen, San Diego, Calif.).

PS133 polypeptides are recovered and purified from recombinant cell cultures by known methods including affinity chromatography, ammonium sulfate or ethanol precipitation, acid extraction, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price et al., *J. Biol. Chem.* 244:917 (1969)). Protein refolding steps can be used, as necessary, in completing configuration of the polypeptide. Finally, high performance liquid chromatography (HPLC) can be employed for final purification steps.

Thus, polypeptides of the present invention may be naturally purified products expressed from a high expressing cell line, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue.

The starting plasmids can be constructed from available plasmids in accord with published, known procedures. In addition, equivalent plasmids to those described are known in the art and will be apparent to one of ordinary skill in the art.

The following is the general procedure for the isolation and analysis of cDNA clones. In a particular embodiment disclosed herein, mRNA was isolated from prostate tissue and used to generate the cDNA library. Prostate tissue was obtained from patients by surgical resection and was classified as tumor or non-tumor tissue by a pathologist.

The cDNA inserts from random isolates of the prostate tissue libraries were sequenced in part, analyzed in detail as set forth in the Examples and are disclosed in the Sequence Listing as SEQUENCE ID NOS 1–6. The consensus sequence of these inserts is presented as SEQUENCE ID NO 7. These polynucleotides may contain an entire open reading frame with or without associated regulatory sequences for a particular gene, or they may encode only a portion of the gene of interest. This is attributed to the fact that many genes are several hundred and sometimes several thousand, bases in length and, with current technology, cannot be cloned in their entirety because of vector limitations, incomplete reverse transcription of the first strand, or incomplete replication of the second strand. Contiguous, secondary clones containing additional nucleotide sequences may be obtained using a variety of methods known to those of skill in the art.

Methods for DNA sequencing are well known in the art. Conventional enzymatic methods employ DNA polymerase, Klenow fragment, Sequenase (US Biochemical Corp, Cleveland, Ohio) or Taq polymerase to extend DNA chains from an oligonucleotide primer annealed to the DNA template of interest. Methods have been developed for the use of both single-stranded and double-stranded templates. The chain termination reaction products may be electrophoresed on urea/polyacrylamide gels and detected either by autoradiography (for radionucleotide labeled precursors) or by fluorescence (for fluorescent-labeled precursors). Recent improvements in mechanized reaction preparation, sequencing and analysis using the fluorescent detection method have permitted expansion in the number of sequences that can be determined per day using machines such as the Applied Biosystems 377 DNA Sequencers (Applied Biosystems, Foster City, Calif.).

The reading frame of the nucleotide sequence can be ascertained by several types of analyses. First, reading frames contained within the coding sequence can be analyzed for the presence of start codon ATG and stop codons TGA, TAA or TAG. Typically, one reading frame will continue throughout the major portion of a cDNA sequence while other reading frames tend to contain numerous stop codons. In such cases, reading frame determination is straightforward. In other more difficult cases, further analysis is required.

Algorithms have been created to analyze the occurrence of individual nucleotide bases at each putative codon triplet. See, for example J. W. Fickett, *Nuc Acids Res* 10:5303 (1982). Coding DNA for particular organisms (bacteria, plants and animals) tends to contain certain nucleotides within certain triplet periodicities, such as a significant preference for pyrimidines in the third codon position. These preferences have been incorporated into widely available software which can be used to determine coding potential (and frame) of a given stretch of DNA. The algorithm-derived information combined with start/stop codon information can be used to determine proper frame with a high degree of certainty. This, in turn, readily permits cloning of the sequence in the correct reading frame into appropriate expression vectors.

The nucleic acid sequences disclosed herein may be joined to a variety of other polynucleotide sequences and vectors of interest by means of well-established recombinant DNA techniques. See J. Sambrook et al., supra. Vectors of interest include cloning vectors, such as plasmids, cosmids, phage derivatives, phagemids, as well as sequencing, replication and expression vectors, and the like. In general, such vectors contain an origin of replication functional in at least one organism, convenient restriction endonuclease digestion sites and selectable markers appropriate for particular host cells. The vectors can be transferred by a variety of means known to those of skill in the art into suitable host cells which then produce the desired DNA, RNA or polypeptides.

Occasionally, sequencing or random reverse transcription errors will mask the presence of the appropriate open reading frame or regulatory element. In such cases, it is possible to determine the correct reading frame by attempting to express the polypeptide and determining the amino acid sequence by standard peptide mapping and sequencing techniques. See, F. M. Ausubel et al., Current Protocols in Molecular Biology, John Wiley & Sons, New York, N.Y. (1989). Additionally, the actual reading frame of a given nucleotide sequence may be determined by transfection of host cells with vectors containing all three potential reading frames. Only those cells with the nucleotide sequence in the correct reading frame will produce a peptide of the predicted length.

The nucleotide sequences provided herein have been prepared by current, state-of-the-art, automated methods and, as such, may contain unidentified nucleotides. These will not present a problem to those skilled in the art who wish to practice the invention. Several methods employing standard recombinant techniques, described in J. Sambrook (supra) or periodic updates thereof, may be used to complete the missing sequence information. The same techniques used for obtaining a full length sequence, as described herein, may be used to obtain nucleotide sequences.

Expression of a particular cDNA may be accomplished by subcloning the cDNA into an appropriate expression vector and transfecting this vector into an appropriate expression host. The cloning vector used for the generation of the prostate tissue cDNA library can be used for transcribing mRNA of a particular cDNA and contains a promoter for beta-galactosidase, an amino-terminal met and the subsequent seven amino acid residues of beta-galactosidase. Immediately following these eight residues is an engineered bacteriophage promoter useful for artificial priming and transcription, as well as a number of unique restriction sites, including EcoRi, for cloning. The vector can be transfected into an appropriate host strain of E. coli.

Induction of the isolated bacterial strain with isopropylthiogalactoside (IPTG) using standard methods will produce a fusion protein which contains the first seven residues of beta-galactosidase, about 15 residues of linker and the peptide encoded within the cDNA. Since cDNA clone inserts are generated by an essentially random process, there is one chance in three that the included cDNA will lie in the correct frame for proper translation. If the cDNA is not in the proper reading frame, the correct frame can be obtained by deletion or insertion of an appropriate number of bases by well known methods including in vitro mutagenesis, digestion with exonuclease III or mung bean nuclease, or oligonucleotide linker inclusion.

The cDNA can be shuttled into other vectors known to be useful for expression of protein in specific hosts. Oligonucleotide primers containing cloning sites and segments of DNA sufficient to hybridize to stretches at both ends of the target cDNA, can be synthesized chemically by standard methods. These primers can then be used to amplify the desired gene segments by PCR. The resulting new gene segments can be digested with appropriate restriction enzymes under standard conditions and isolated by gel electrophoresis. Alternately, similar gene segments can be produced by digestion of the cDNA with appropriate restriction enzymes and filling in the missing gene segments with chemically synthesized oligonucleotides. Segments of the coding sequence from more than one gene can be ligated together and cloned in appropriate vectors to optimize expression of recombinant sequence.

Suitable expression hosts for such chimeric molecules include, but are not limited to, mammalian cells such as Chinese Hamster Ovary (CHO) and human embryonic kidney (HEK) 293 cells, insect cells such as Sf9 cells, yeast cells such as Saccharomyces cerevisiae and bacteria such as E. coli. For each of these cell systems, a useful expression vector may also include an origin of replication to allow propagation in bacteria and a selectable marker such as the beta-lactamase antibiotic resistance gene to allow selection in bacteria. In addition, the vectors may include a second selectable marker, such as the neomycin phosphotransferase gene, to allow selection in transfected eukaryotic host cells. Vectors for use in eukaryotic expression hosts may require the addition of 3' poly A tail if the sequence of interest lacks poly A.

Additionally, the vector may contain promoters or enhancers which increase gene expression. Such promoters are host specific and include, but are not limited to, MMTV, SV40, or metallothionine promoters for CHO cells; trp, lac, tac or T7 promoters for bacterial hosts; or alpha factor, alcohol oxidase or PGH promoters for yeast. Adenoviral vectors with or without transcription enhancers, such as the rous sarcoma virus (RSV) enhancer, may be used to drive protein expression in mammalian cell lines. Once homogeneous cultures of recombinant cells are obtained, large quantities of recombinantly produced protein can be recovered from the conditioned medium and analyzed using chromatographic methods well known in the art. An alternative method for the production of large amounts of secreted protein involves the transfection of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays

PS133 polypeptides, including fragments, derivatives, and analogs thereof, or cells expressing such polypeptides, can be utilized in a variety of assays, many of which are described herein, for the detection of antibodies to prostate tissue. They also can be used as immunogens to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide comprising a sequence of the present invention can be obtained by direct injection of the polypeptide into an animal or by administering the polypeptide to an animal such as a mouse, rabbit, goat or human. A mouse, rabbit or goat is preferred. The polypeptide is selected from the group consisting of SEQUENCE ID NO 24, SEQUENCE ID NO 25, SEQUENCE ID NO 26, SEQUENCE ID NO 27, and fragments thereof. The antibody so obtained then will bind the polypeptide itself. In this manner, even a sequence encoding only a fragment of the polypeptide can be used to generate antibodies that bind the native polypeptide. Such antibodies then can be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256:495–497 (1975), the trioma technique, the human B-cell hybridoma technique as described by Kozbor et al., *Immun. Today* 4:72 (1983) and the EBV-hybridoma technique to produce human monoclonal antibodies as described by Cole, et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the antibodies of the present invention, or fragments thereof, can be employed in various assay systems to determine the presence, if any, of PS133 antigen in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of PS133 antigen in the test sample and captured on the solid phase, if any, is determined by detecting the measurable signal generated by the signal generating compound. The amount of PS133 antigen present in the test sample is proportional to the signal generated.

In an alternative assay format, a mixture is formed by contacting: (1) a polyclonal antibody, monoclonal antibody, or fragment thereof, which specifically binds to PS133 antigen, or a combination of such antibodies bound to a solid support; (2) the test sample; and (3) an indicator reagent comprising a monoclonal antibody, polyclonal antibody, or fragment thereof, which specifically binds to a different PS133 antigen (or a combination of these antibodies) to which a signal generating compound is attached. This mixture is incubated for a time and under conditions sufficient to form antibody/antigen/antibody complexes. The presence, if any, of PS133 antigen present in the test sample and captured on the solid phase is determined by detecting the measurable signal generated by the signal generating compound. The amount of PS133 antigen present in the test sample is proportional to the signal generated.

In another assay format, one or a combination of at least two monoclonal antibodies of the invention can be employed as a competitive probe for the detection of antibodies to PS133 antigen. For example, PS133 polypeptides such as the recombinant antigens disclosed herein, either alone or in combination, are coated on a solid phase. A test sample suspected of containing antibody to PS133 antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of PS133 antigens in tissue sections, as well as in cells, by immunohistochemical analysis. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific PS133 polypeptides from cell cultures or biological tissues such as to purify recombinant and native PS133 proteins.

The monoclonal antibodies of the invention also can be used for the generation of chimeric antibodies for therapeutic use, or other similar applications.

The monoclonal antibodies or fragments thereof can be provided individually to detect PS133 antigens. Combinations of the monoclonal antibodies (and fragments thereof) provided herein also may be used together as components in a mixture or "cocktail" of at least one PS133 antibody of the invention, along with antibodies which specifically bind to other PS133 regions, each antibody having different binding specificities. Thus, this cocktail can include the monoclonal antibodies of the invention which are directed to PS133 polypeptides disclosed herein and other monoclonal antibodies specific to other antigenic determinants of PS133 antigens or other related proteins.

The polyclonal antibody or fragment thereof which can be used in the assay formats should specifically bind to a PS133 polypeptide or other PS133 polypeptides additionally used in the assay. The polyclonal antibody used preferably is of mammalian origin such as, human, goat, rabbit or sheep polyclonal antibody which binds PS133 polypeptide. Most preferably, the polyclonal antibody is of rabbit origin. The polyclonal antibodies used in the assays can be used either alone or as a cocktail of polyclonal antibodies. Since the cocktails used in the assay formats are comprised of either monoclonal antibodies or polyclonal antibodies having different binding specificity to PS133 polypeptides, they are useful for the detecting, diagnosing, staging, monitoring, prognosticating, preventing or treating, or determining the predisposition to, diseases and conditions of the prostate, such as prostate cancer.

It is contemplated and within the scope of the present invention that PS133 antigen may be detectable in assays by use of a recombinant antigen as well as by use of a synthetic peptide or purified peptide, which peptide comprises an amino acid sequence of PS133. The amino acid sequence of such a polypeptide is selected from the group consisting of SEQUENCE ID NO 24, SEQUENCE ID NO 25, SEQUENCE ID NO 26, SEQUENCE ID NO 27, and fragments thereof. It also is within the scope of the present invention that different synthetic, recombinant or purified peptides, identifying different epitopes of PS133, can be used in combination in an assay for the detecting, diagnosing, staging, monitoring, prognosticating, preventing or treating, or determining the predisposition to diseases and conditions of the prostate, such as prostate cancer. In this case, all of these peptides can be coated onto one solid phase; or each separate peptide may be coated onto separate solid phases, such as microparticles, and then combined to form a mixture of peptides which can be later used in assays. Furthermore, it is contemplated that multiple peptides which define epitopes from different antigens may be used for the detection, diagnosis, staging, monitoring, prognosis, prevention or treatment of, or determining the predisposition to, diseases and conditions of the prostate, such as prostate cancer. Peptides coated on solid phases or labeled with detectable labels are then allowed to compete with those present in a patient sample (if any) for a limited amount of antibody. A reduction in binding of the synthetic, recombinant, or purified peptides to the antibody (or antibodies) is an indication of the presence of PS133 antigen in the patient sample. The presence of PS133 antigen indicates the presence of prostate tissue disease, especially prostate cancer, in the patient. Variations of assay formats are known to those of ordinary skill in the art and many are discussed herein below.

In another assay format, the presence of anti-PS133 antibody and/or PS133 antigen can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from the expression systems disclosed herein may be utilized, as well as monoclonal antibodies produced from the proteins derived from the expression systems as disclosed herein. For example, in this assay system, PS133 antigen can be the first analyte. Such assay systems are described in greater detail in EP Publication No. 0473065.

In yet other assay formats, the polypeptides disclosed herein may be utilized to detect the presence of antibody against PS133 antigen in test samples. For example, a test sample is incubated with a solid phase to which at least one polypeptide such as a recombinant protein or synthetic peptide has been attached. The polypeptide is selected from the group consisting of SEQUENCE ID NO 24, SEQUENCE ID NO 25, SEQUENCE ID NO 26, SEQUENCE ID NO 27, and fragments thereof. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached, and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of antibody against PS133 antigen. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as $E.\ coli$ is used as a capture antigen on a solid phase, a test sample is added to the so-prepared solid phase, and following standard incubation and washing steps as deemed or required, a recombinant protein derived from a different source (i.e., non-$E.\ coli$) is utilized as a part of an indicator reagent which subsequently is detected. Likewise, combinations of a recombinant antigen on a solid phase and synthetic peptide in the indicator phase also are possible. Any assay format which utilizes an antigen specific for PS133 produced or derived from a first source as the capture antigen and an antigen specific for PS133 from a different second source is contemplated. Thus, various combinations of recombinant antigens, as well as the use of synthetic peptides, purified proteins and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including automated and semi-automated systems wherein the solid phase comprises a microparticle (magnetic or non-magnetic). Such systems include those described in, for example, published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, particularly in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (e.g. recombinantly, synthetically produced or purified) employed in the assay. The polypeptide is selected from the group consisting of SEQUENCE ID NO 24, SEQUENCE ID NO 25, SEQUENCE ID NO 26, SEQUENCE ID NO 27, and fragments thereof. Other components such as buffers, controls and the like, known to those of ordinary skill in art, may be included in such test kits. It also is contemplated to provide test kits which have means for collecting test samples comprising accessible body fluids, e.g., blood, urine, saliva and stool. Such tools useful for collection ("collection materials") include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization and preservation of test specimens obtained by surgery or needle biopsy are also useful. It is contemplated that all kits may be configured in two components which can be provided separately; one component for collection and transport of the specimen and the other component for the analysis of the specimen. The collection component, for example, can be provided to the open market user while the components for analysis can be provided to others such as laboratory personnel for determination of the presence, absence or amount of analyte. Further, kits for the collection, stabilization and preservation of test specimens may be configured for use by untrained personnel and may be available in the open market for use at home with subsequent transportation to a laboratory for analysis of the test sample.

*E. coli* bacteria (clone 2346388) has been deposited at the American Type Culture Collection (A.T.C.C.), 12301 Parklawn Drive, Rockville, Md. 20852, as of Oct. 31, 1997, under the terms of the Budapest Treaty and will be maintained for a period of thirty (30) years from the date of deposit, or for five (5) years after the last request for the deposit, or for the enforceable period of the U.S. patent, whichever is longer. The deposit and any other deposited material described herein are provided for convenience only, and are not required to practice the present invention in view of the teachings provided herein. The cDNA sequence in all of the deposited material is incorporated herein by reference. Clone 2346388 was accorded A.T.C.C. Deposit No. 98572.

The present invention will now be described by way of examples, which are meant to illustrate, but not to limit, the scope of the present invention.

EXAMPLES

Example 1

Identification of Prostate Tissue Library PS133 Gene-Specific Clones

A. Library Comparison of Expressed Sequence Tags (ESTs) or Transcript Images.

Partial sequences of cDNA clone inserts, so-called "expressed sequence tags" (ESTs), were derived from cDNA libraries made from prostate tumor tissues, prostate non-tumor tissues and numerous other tissues, both tumor and non-tumor and entered into a database (LIFESEQ™ database, available from Incyte Pharmaceuticals, Palo Alto, Calif.) as gene transcript images. See International Publication No. WO 95/20681. (A transcript image is a listing of the number of EST's for each of the represented genes in a given tissue library. ESTs sharing regions of mutual sequence overlap are classified into clusters. A cluster is assigned a clone number from a representative 5' EST. Often, a cluster of interest can be extended by comparing its consensus sequence with sequences of other EST's which did not meet the criteria for automated clustering. The alignment of all available clusters and single ESTs represent a contig from which a consensus sequence is derived.) The transcript images then were evaluated to identify EST sequences that were representative primarily of the prostate tissue libraries. These target clones then were ranked according to their abundance (occurrence) in the target libraries and their absence from background libraries. Higher abundance clones with low background occurrence were given higher study priority. ESTs corresponding to the consensus sequence of PS133 were found in 40.9% (9 of 22) of prostate tissue libraries. ESTs corresponding to the consensus sequence SEQUENCE ID NO 7 (or fragments thereof) were found in only 2.3% (7 of 301) of the other, non-prostate, libraries of the data base. Therefore, the consensus sequence or fragment thereof was found more than 17 times more often in prostate than non-prostate tissues. Overlapping clones 828846 (SEQUENCE ID NO 1), 2346388

(SEQUENCE ID NO 2), 2531505 (SEQUENCE ID NO 3), 1725220 (SEQUENCE ID NO 4), 1856238 (SEQUENCE ID NO 5), and g1367041 (SEQUENCE ID NO 6) were identified for further study. These represented the minimum number of clones that were needed to form the contig and from which the consensus sequence provided herein (SEQUENCE ID NO 7) was derived.

B. Generation of a Consensus Sequence.

The nucleotide sequences of clones 828846 (SEQUENCE ID NO 1), 2346388 (SEQUENCE ID NO 2), 2531505 (SEQUENCE ID NO 3), 1725220 (SEQUENCE ID NO 4), 1856238 (SEQUENCE ID NO 5), g1367041 (SEQUENCE ID NO 6) were entered in the Sequencher™ Program (available from Gene Codes Corporation, Ann Arbor, Mich., in order to generate a nucleotide alignment (contig map) and then generate their consensus sequence (SEQUENCE ID NO 7). FIGS. 1A–1B show the nucleotide sequence alignment of these clones and their resultant nucleotide consensus sequence (SEQUENCE ID NO 7). FIG. 2 presents the contig map depicting the clones SEQUENCE ID NOS 1–6 forming overlapping regions of the PS133 gene and the resultant consensus nucleotide sequence (SEQUENCE ID NO 7) of these clones in a graphic display. Following this, a three-frame translation was performed on the consensus sequence (SEQUENCE ID NO 7). The first forward frame was found to have an open reading frame encoding a 250 residue amino acid sequence, which is presented as SEQUENCE ID NO 24. The 250 residue polypeptide sequence depicted in SEQUENCE ID NO 24 was compared with published sequences using software and techniques known to those skilled in the art. The polypeptide sequence of a murine serine protease termed "neuropsin" was found to be partially homologous to the PS133 polypeptide of SEQUENCE ID NO 24. The neuropsin enzyme is described by Z. Chen et al. *J. Neurosci.* 15:5088–5097 (1995).

The consensus polypeptide of SEQUENCE ID NO 24 was also compared against non-redundant protein data (non-redundant protein data is a database that has removed multiple references to proteins containing the same sequence) from the GenBank and EMBL databases using a FASTA software program. The comparison indicated significant homology with regions of human serine proteases. (Significant homology was determined as a sequence of amino acid residues within the PS133 polypeptide which shared identical or conserved amino acid residues to one of three catalytically functional motifs within a serine proteinase, such that one skilled in the art could identify the sequence as belonging to one of the three serine protease motifs.) The regions were identified as the catalytically functional motifs of serine protease (see Example 1C).

C. Alignment of PS133 Peptide with Known Serine Proteases

A detailed alignment of the PS133 polypeptide consensus sequence, SEQUENCE ID NO 24, with 47 known human serine proteases or serine protease-like proteins (SEQUENCE ID NOS 28–74) was performed. The PS133 consensus polypeptide was aligned against the primary sequence of the human serine proteases or serine protease-like domains from the GenBank database (D. A. Benson et al., *Nuc. Acids Res.*, Vol 25, pp 1–6, 1997, Oxford University Press) using the PILEUP computer program available from Genetics Computer Group, Inc (University Research Park, Madison, Wis., USA). This alignment is shown in FIGS. 3A–D. The functional motifs which are present in all catalytically functional serine proteases are also present in the PS133 polypeptide. The functional motifs are marked with an "*" in FIGS. 3A–D. Based on the homology of the PS133 polypeptide with the functional motifs of other proteins in the databases, the program identified the PS133 polypeptide as a member of the human serine protease family.

Example 2

Sequencing of PS133 EST-Specific Clones

The DNA sequence of clone 2346388 which comprises one of the 5'-most ESTs of the PS133 gene contig was determined using dideoxy termination sequencing with dye terminators following known methods and is depicted as SEQUENCE ID NO 8. (F. Sanger et al., *PNAS U.S.A.* 74:5463 (1977)).

Because the pSPORT1 vector (Life Technologies, Gaithersburg, Md.) contains universal priming sites just adjacent to the 3' and 5' ligation junctions of the inserts, approximately 300 bases of the insert were sequenced in both directions using universal primers, SEQUENCE ID NO 11 and SEQUENCE ID NO 12 (New England Biolabs, Beverly, Mass. and Applied Biosystems Inc, Foster City, Calif., respectively). The sequencing reactions were run on a polyacrylamide denaturing gel, and the sequences were determined by an Applied Biosystems 377 Sequencer (available from Applied Biosystems, Foster City, Calif.) or other sequencing apparatus. Additional sequencing primers, PS133.F1-5 and PS133.R1-6 (SEQUENCE ID NOS 13–17 and SEQUENCE ID NOS 18–23, respectively) were designed from the consensus sequence (SEQUENCE ID NO 7). These primers were used to determine the remaining DNA sequence of the cloned insert from each DNA strand, as previously described.

Example 3

Nucleic Acid Preparation

A. RNA Extraction from Tissue.

Total RNA is isolated from solid prostate tissues or cells and from non-prostate tissues. Various methods are utilized, including but not limited to the lithium chloride/urea technique, known and described in the art (Kato et al., *J. Virol.* 61:2182–2191, [1987]), Ultraspec™ (Biotecx Laboratories, Inc., Houston Tex.), and TRIzol™ (Life Technologies, Inc., Gaithersburg, Md.).

For northern blot analysis, the tissue is placed in a sterile conical tube on ice and 10–15 volumes of 3M LiCl, 6M urea, 5 mM EDTA, 0.1M β-mercaptoethanol, 50 mM Tris-HCl (pH 7.5) are added. The tissue is homogenized with a Polytron® homogenizer (Brinkman Instruments, Inc., Westbury, N.Y.) for 30–50 sec on ice. The solution is transferred to a 15 ml plastic centrifuge tube and placed overnight at −20° C. The tube is centrifuged for 90 min at 9,000×g at 0–4° C., and the supernatant is immediately decanted. Then, 10 ml of 3M LiCl are added, the tube is vortexed for 5 sec and centrifuged for 45 min at 11,000×g at 0–4° C. Decanting, resuspension in LiCl, and centrifugation are repeated. The final pellet is air dried and resuspended in 2 ml of 1 mM EDTA, 0.5% SDS, 10 mM Tris (pH 7.5). Then, 20 µl of Proteinase K (20 mg/ml) are added, and the solution is incubated for 30 min at 37° C. with occasional mixing. One-tenth volume (0.22–0.25 ml) of 3M NaCl is added, and the solution is vortexed before transfer into another tube which contains 2 ml of phenol/chloroform/isoamyl alcohol (PCI). The tube is vortexed for 1–3 sec and centrifuged for 20 min at 3,000×g at 10° C. The PCI extraction is repeated twice more, followed by two similar extractions with chloroform/isoamyl alcohol. The final aqueous solution is transferred to a pre-chilled 15 ml corex glass tube containing 6 ml of 100% absolute ethanol, the tube is covered with parafilm and placed at −20° C. overnight. The tube is centrifuged for 30 min at 10,000×g at 0–4° C., and the ethanol supernatant is decanted immediately. The RNA pellet is washed four times with 10 ml of 75% ice-cold ethanol, followed each time by centrifugation at 10,000×g for 10 min. The final pellet is air dried for 15 min at room temperature. The RNA is suspended in 0.5 ml of 10 mM Tris (pH 7.6), 1 mM EDTA, and its concentration is determined spectrophotometrically. RNA samples are aliquoted and stored at −70° C. as ethanol precipitates.

The quality of the RNA is determined by agarose gel electrophoresis (see Example 5) and staining with 0.5 µg/ml ethidium bromide for one hour. RNA samples that do not contain intact 28S/18S rRNAs are excluded from the study.

Alternatively, for RT-PCR analysis, 1 ml of Ultraspec RNA reagent is added to 120 mg of pulverized tissue in a 2.0 ml polypropylene microfuge tube, homogenized with a Polytron® homogenizer (Brinkman Instruments, Inc., Westbury, N.Y.) for 50 sec and left on ice for 5 min. Then, 0.2 ml of chloroform is added to each sample, followed by vortexing for 15 sec. The sample is left in ice for another 5 min, followed by centrifugation at 12,000×g for 15 min at 4° C. The upper layer is collected and transferred to another RNase-free 2.0 ml microfuge tube. An equal volume of isopropanol is added to each sample, and the solution is placed on ice for 10 min. The sample is centrifuged at 12,000×g for 10 min at 4° C., and the supernatant is discarded. The remaining pellet is washed twice with cold 75% ethanol, resuspended by vortexing, and the resuspended material is then re-pelleted by centrifugation at 7500×g for 5 min at 4° C. Finally, the RNA pellet is dried in a speedvac for at least 5 min and reconstituted in RNase-free water.

B. RNA Extraction from Blood Mononuclear Cells.

Mononuclear cells are isolated from blood samples from patients by centrifugation using Ficoll-Hypaque as follows. A 10 ml volume of whole blood is mixed with an equal volume of RPMI Medium (Life Technologies, Gaithersburg, Md.). This mixture is then underlayed with 10 ml of Ficoll-Hypaque (Pharmacia, Piscataway, N.J.) and centrifuged for 30 minutes at 200×g. The buffy coat containing the mononuclear cells is removed, diluted to 50 ml with Dulbecco's PBS (Life Technologies, Gaithersburg, Md.) and the mixture centrifuged for 10 minutes at 200×g. After two washes, the resulting pellet is resuspended in Dulbecco's PBS to a final volume of 1 ml.

RNA is prepared from the isolated mononuclear cells as described by N. Kato et al., *J. Virology* 61: 2182–2191 (1987). Briefly, the pelleted mononuclear cells are brought to a final of 1 ml volume and then are resuspended in 250 µL of PBS and mixed with 2.5 ml of 3M LiCl, 6M urea, 5 mM EDTA, 0.1M 2-mercaptoethanol, 50 mM Tris-HCl (pH 7.5). The resulting mixture is homogenized and incubated at −20° C. overnight. The homogenate is spun at 8,000 RPM in a Beckman J2-21M rotor for 90 minutes at 0–4° C. The pellet is resuspended in 10 ml 3M LiCl by vortexing and then spun at 10,000 RPM in a Beckman J2-21M rotor centrifuge for 45 minutes at 0–4° C. The resuspending and pelleting steps then are repeated. The pellet is resuspended in 2 ml of 1 mM EDTA, 0.5% SDS, 10 mM Tris (pH 7.5) and 400 µg Proteinase K with vortexing and then it is incubated at 37° C. for 30 minutes with shaking. One tenth volume of 3M NaCl then is added and the vortexed mixture. Proteins are removed by two cycles of extraction with phenol/chloroform/isoamyl alcohol followed by one extraction with chloroform/isoamyl alcohol. RNA is precipitated by the addition of 6 ml of ethanol followed by overnight incubation at −20° C. After the precipitated RNA is collected by centrifugation, the pellet is washed 4 times in 75% ethanol. The pelleted RNA is then dissolved in 1 mM EDTA, 10 mM Tris-HCl (pH 7.5).

Non-prostate tissues are used as negative controls. The mRNA can be further purified from total RNA by using commercially available kits such as oligo dT cellulose spin columns (RediCol™ from Pharrnacia, Uppsala, Sweden) for the isolation of poly-adenylated RNA. Total or mRNA can be dissolved in lysis buffer (5M guanidine thiocyanate, 0.1M EDTA, pH 7.0) for analysis in the ribonuclease protection assay.

C. RNA Extraction from polysomes.

Tissue is minced in saline at 4° C. and mixed with 2.5 volumes of 0.8M sucrose in a $TK_{150}M$ (150 mM KCl, 5 mM $MgCl_2$, 50 mM Tris-HCl, pH 7.4) solution containing 6 mM 2-mercaptoethanol. The tissue is homogenized in a Teflon-glass Potter homogenizer with five strokes at 100–200 rpm followed by six strokes in a Dounce homogenizer, as described by B. Mechler, *Methods in Enzymology* 152:241–248 (1987). The homogenate then is centrifuged at 12,000×g for 15 min at 4° C. to sediment the nuclei. The polysomes are isolated by mixing 2 ml of the supernatant with 6 ml of 2.5M sucrose in $TK_{150}M$ and layering this mixture over 4 ml of 2.5M sucrose in $TK_{150}M$ in a 38 ml polyallomer tube. Two additional sucrose $TK_{150}M$ solutions are successively layered onto the extract fraction; a first layer of 13 ml 2.05M sucrose followed by a second layer of 6 ml of 1.3M sucrose. The polysomes are isolated by centrifuging the gradient at 90,000×g for 5 h at 4° C. The fraction then is taken from the 1.3M sucrose/2.05M sucrose interface with a siliconized pasteur pipette and diluted in an equal volume of TE (10 mM Tris-HCl, pH 7.4, 1 mM EDTA). An equal volume of 90° C. SDS buffer (1% SDS, 200 mM NaCl, 20 mM Tris-HCl, pH 7.4) is added and the solution is incubated in a boiling water bath for 2 min. Proteins next are digested with a Proteinase-K digestion (50 mg/ml) for 15 min at 37° C. The mRNA is purified with 3 equal volumes of phenol-chloroform extractions followed by precipitation with 0.1 volume of 2M sodium acetate (pH 5.2) and 2 volumes of 100% ethanol at −20° C. overnight. The precipitated RNA is recovered by centrifugation at 12,000×g for 10 min at 4° C. The RNA is dried and resuspended in TE (pH 7.4) or distilled water. The resuspended RNA then can be used in a slot blot or dot blot hybridization assay to check for the presence of PS133 mRNA (see Example 6).

The quality of nucleic acid and proteins is dependent on the method of preparation used. Each sample may require a different preparation technique to maximize isolation efficiency of the target molecule. These preparation techniques are within the skill of the ordinary artisan.

Example 4

Ribonuclease Protection Assay

A. Synthesis of Labeled Complementary RNA (cRNA) Hybridization Probe and Unlabeled Sense Strand.

Labeled antisense and unlabeled sense riboprobes are transcribed from the PS133 gene cDNA sequence which contains a 5' RNA polymerase promoter such as SP6 or T7. The sequence may be from a vector containing the appropriate PS133 cDNA insert, or from a PCR-generated product of the insert using PCR primers which incorporate a 5' RNA polymerase promoter sequence. For example, the described plasmid, clone 2346388 or other comparable clone, containing the PS133 gene cDNA sequence, flanked by opposed SP6 and T7 polymerase promoters, is purified using Qiagen Plasmid Purification Kit (Qiagen, Chatsworth, Calif.). Then 10 μg of the plasmid are linearized by cutting with 10 U DdeI restriction enzyme for 1 h at 37° C. The linearized plasmid is purified using QIAprep kits (Qiagen, Chatsworth, Calif.) and used for the synthesis of antisense transcript from the appropriate SP6 or T7 promoter using the Riboprobe® in vitro Transcription System (Promega Corporation, Madison, Wis.), as described by the supplier's instructions, incorporating either 6.3 μM (alpha$^{32}$P) UTP (Amersham Life Sciences, Inc. Arlington Heights, Ill.) or 100–500 μM biotinylated UTP as a label. To generate the sense strand, 10 μg of the purified plasmid are cut with restriction enzymes 10U XbaI and 10 U NotI, and transcribed as above from the appropriate SP6 or T7 promoter. Both sense and antisense strands are isolated by spin column chromatography. Unlabeled sense strand is quantitated by UV absorption at 260 nm.

B. Hybridization of Labeled Probe to Target.

Frozen tissue is pulverized to powder under liquid nitrogen and 100–500 mg are dissolved in 1 ml of lysis buffer, available as a component of the Direct Protect™ Lysate RNase Protection kit (Ambion, Inc., Austin, Tex.). Further dissolution can be achieved using a tissue homogenizer. In addition, a dilution series of a known amount of sense strand in mouse liver lysate is made for use as a positive control. Finally, 45 μl of solubilized tissue or diluted sense strand is mixed directly with either 1) 1×10$^5$ cpm of radioactively labeled probe or 2) 250 pg of non-isotopically labeled probe in 5 μl of lysis buffer. Hybridization is allowed to proceed overnight at 37° C. See, T. Kaabache et al., *Anal. Biochem.* 232:225–230 (1995).

C. RNase Digestion.

RNA that is not hybridized to probe is removed from the reaction as per the Direct Protect™ protocol using a solution of RNase A and RNase T1 for 30 min at 37° C., followed by removal of RNase by Proteinase-K digestion in the presence of sodium sarcosyl. Hybridized fragments protected from digestion are then precipitated by the addition of an equal volume of isopropanol and placed at −70° C. for 3 h. The precipitates are collected by centrifugation at 12,000×g for 20 min.

D. Fragment Analysis.

The precipitates are dissolved in denaturing gel loading dye (80% formamide, 10 mM EDTA (pH 8.0), 1 mg/ml xylene cyanol, 1 mg/ml bromophenol blue), heat denatured, and electrophoresed in 6% polyacrylamide TBE, 8M urea denaturing gels. The gels are imaged and analyzed using the STORM™ storage phosphor autoradiography system (Molecular Dynamics, Sunnyvale, Calif.). Quantitation of protected fragment bands, expressed in femtograms (fg), is achieved by comparing the peak areas obtained from the test samples to those from the known dilutions of the positive control sense strand (see Section B, supra). The results are expressed in molecules of PS133 RNA/cell and as a image rating score. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents. High level expression of mRNA corresponding to a sequence selected from the group consisting of SEQUENCE ID NOS 1–8, and fragments or complements thereof, indicate the presence of PS133 mRNA(s), suggesting a diagnosis of a prostate tissue disease or condition, such as prostate cancer.

Example 5

Northern Blotting

The northern blot technique is used to identify a specific size RNA fragment from a complex population of RNA using gel electrophoresis and nucleic acid hybridization. Northern blotting is well-known technique in the art. Briefly, 5–10 μg of total RNA (see Example 3) are incubated in 15 μl of a solution containing 40 mM morphilinopropanesulfonic acid (MOPS) (pH 7.0), 10 mM sodium acetate, 1 mM EDTA, 2.2M formaldehyde, 50% v/v formamide for 15 min at 65° C. The 30 denatured RNA is mixed with 2 $^1$μl of loading buffer (50% glycerol, 1 mM EDTA, 0.4% bromophenol blue, 0.4% xylene cyanol) and loaded into a denaturing 1.0% agarose gel containing 40 mM MOPS (pH 7.0), 10 mM sodium acetate, 1 mM EDTA and 2.2M formaldehyde. The gel is electrophoresed at 60 V for 1.5 h and rinsed in RNAse free water. RNA is transferred from the gel onto nylon membranes (Brightstar-Plus, Ambion, Inc., Austin, Tex.) for 1.5 hours using the downward alkaline capillary transfer method (Chomczynski, *Anal. Biochem.* 201:134–139, 1992). The filter is rinsed with 1×SSC, and RNA is crosslinked to the filter using a Stratalinker (Stratagene, Inc., La Jolla, Calif.) on the autocrosslinking mode and dried for 15 min. The membrane is then placed into a hybridization tube containing 20 ml of preheated prehybridization solution (5×SSC, 50% formamide, 5×Denhardt's solution, 100 μg/ml denatured salmon sperm DNA) and incubated in a 42° C. hybridization oven for at least 3 hr. While the blot is prehybridizing, a $^{32}$P-labeled random-primed probe is generated using the PS133 insert fragment (obtained by digesting clone 2346388 or another comparable clone, with XbaI and NotI) using Random Primer DNA Labeling System (Life Technologies, Inc., Gaithersburg, Md.) according to the manufacturer's instructions. Half of the probe is boiled for 10 min, quick chilled on ice and added to the hybridization tube. Hybridization is carried out at 42° C. for at least 12 hr. The hybridization solution is discarded and the filter is washed in 30 ml of 3×SSC, 0.1% SDS at 42° C. for 15 min, followed by 30 ml of 3×SSC, 0.1% SDS at 42° C. for 15 min. The filter is wrapped in saran wrap, exposed to Kodak XAR-Omat film for 8–96 hr, and the film is developed for analysis. High level of expression of mRNA corresponding to a sequence selected from the group consisting of SEQUENCE ID NOS 1–8, and fragments or complements thereof, is an indication of the presence of PS133 mRNA, suggesting a diagnosis of a prostate tissue disease or condition, such as prostate cancer.

Example 6

Dot Blot/Slot Blot

Dot and slot blot assays are quick methods to evaluate the presence of a specific nucleic acid sequence in a complex mix of nucleic acid. To perform such assays, up to 50 μg of RNA is mixed in 50 μl of 50% formamide, 7% formaldehyde, 1×SSC, incubated 15 min at 68° C., and then cooled on ice. Then, 100 μl of 20×SSC is added to the RNA mixture and loaded under vacuum onto a manifold apparatus that has a prepared nitrocellulose or nylon membrane. The membrane is soaked in water, 20×SSC for 1 hour, placed on two sheets of 20×SSC prewet Whatman #3 filter paper, and loaded into a slot blot or dot blot vacuum manifold apparatus. The slot blot is analyzed with probes prepared and labeled as described in Example 4, supra. Detection of mRNA corresponding to a sequence selected from the group consisting of SEQUENCE ID NOS 1–8, and fragments or complements thereof, is an indication of the presence of PS133, suggesting a diagnosis of a prostate tissue disease or condition, such as prostate cancer.

Other methods and buffers which can be utilized in the methods described in Examples 5 and 6, but not specifically detailed herein, are known in the art and are described in J. Sambrook et al., supra which is incorporated herein by reference.

Example 7

In Situ Hybridization

This method is useful to directly detect specific target nucleic acid sequences in cells using detectable nucleic acid hybridization probes.

Tissues are prepared with cross-linking fixative agents such as paraformaldehyde or glutaraldehyde for maximum cellular RNA retention. See, L. Angerer et al., *Methods in Cell Biol.* 35:37–71 (1991). Briefly, the tissue is placed in greater than 5 volumes of 1% glutaraldehyde in 50 mM sodium phosphate, pH 7.5 at 4° C. for 30 min. The solution is changed with fresh glutaraldehyde solution (1% glutaraldehyde in 50 mM sodium phosphate, pH 7.5) for a further 30 min fixing. The fixing solution should have an osmolality of approximately 0.375% NaCl. The tissue is washed once in isotonic NaCl to remove the phosphate.

The fixed tissues then are embedded in paraffin as follows. The tissue is dehydrated though a series of ethanol concentrations for 15 min each: 50% (twice), 70% (twice), 85%, 90% and then 100% (twice). Next, the tissue is soaked in two changes of xylene for 20 min each at room temperature. The tissue is then soaked in two changes of a 1:1 mixture of xylene and paraffin for 20 min each at 60° C.; and then in three final changes of paraffin for 15 min each.

Next, the tissue is cut in 5 µm sections using a standard microtome and placed on a slide previously treated with a tissue adhesive such as 3-aminopropyltriethoxysilane.

Paraffin is removed from the tissue by two 10 min xylene soaks and rehydrated in a series of ethanol concentrations: 99% twice, 95%, 85%, 70%, 50%, 30%, and then distilled water twice. The sections are pre-treated with 0.2M HCl for 10 min and permeabilized with 2 µg/ml Proteinase-K at 37° C. for 15 min.

Labeled riboprobes transcribed from the PS133 gene plasmid (see Example 4) are hybridized to the prepared tissue sections and incubated overnight at 56° C. in 3×standard saline extract and 50% formamide. Excess probe is removed by washing in 2×standard saline citrate and 50% formamide followed by digestion with 100 µg/ml RNase A at 37° C. for 30 min. Fluorescence probe is visualized by illumination with ultraviolet (UV) light under a microscope. Fluorescence in the cytoplasm is indicative of PS133 mRNA. Alternatively, the sections can be visualized by autoradiography.

Example 8

Reverse Transcription PCR

A. One Step RT-PCR Assay.

Target-specific primers are designed to detect the above-described target sequences by reverse transcription PCR using methods known in the art. One step RT-PCR is a sequential procedure that performs both RT and PCR in a single reaction mixture. The procedure is performed in a 200 µl reaction mixture containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 µM each of dNTP, 0.25 µM each primer, 5U rTth polymerase, 3.25 mM Mn(OAc)$_2$ and 5 µl of target RNA (see Example 3). Since RNA and the rTth polymerase enzyme are unstable in the presence of Mn(OAc)$_2$, the Mn(OAc)$_2$ should be added just before target addition. Optimal conditions for cDNA synthesis and thermal cycling readily can be determined by those skilled in the art. The reaction is incubated in a Perkin-Elmer Thermal Cycler 480. Optimal conditions for cDNA synthesis and thermal cycling can readily be determined by those skilled in the art. Conditions which may be found useful include cDNA synthesis at 60°–31 70° C. for 15–45 min and 30–45 amplification cycles at 94° C., 1 min; 55°–70° C., 1 min; 72° C., 2 min. One step RT-PCR also may be performed by using a dual enzyme procedure with Taq polymerase and a reverse transcriptase enzyme, such as MMLV or AMV RT enzymes.

B. Traditional RT-PCR.

Alternatively, a traditional two-step RT-PCR reaction may be performed, as described by K. Q. Hu et al., *Virology* 181:721–726 (1991), as follows. The extracted mRNA is transcribed in a 25 µl reaction mixture containing 10 mM Tris-HCl, pH 8.3, 5 mM MgCl$_2$, 500 µM dNTP, 20 U RNasin, 1 µM antisense primer and 25 U AMV (avian myeloblastosis virus) or MMLV (Moloney murine leukemia virus) reverse transcriptase. Reverse transcription is performed at 37–45° C. for 30–60 min, followed by further incubation at 95° C. for 5 min to inactivate the RT. PCR is performed using 10 µl of the cDNA reaction in a final PCR reaction volume of 50 µl containing 10 mM Tris-HCl (pH 8.3), 50 mM KCl, 2 mM MgCl$_2$, 200 µM dNTP, 0.5 µM of each primer and 2.5 U of Taq polymerase. Optimal conditions for cDNA synthesis and thermal cycling can be readily determined by those skilled in the art. The reaction is incubated in a Perkin-Elmer Thermal Cycler 480 or other comparable instrument. Conditions which may be found useful include 30–45 cycles of amplification (94° C., 1 min; 55–70° C., 1 min; 72° C., 2 min), final extension (72° C., 10 min) and soak at 4° C.

C. PCR Fragment Analysis.

The correct products then can be verified by size determination using gel electrophoresis with fluorescent intercalators, such as SYBR® Green I (Molecular Probes, Eugene, Oreg.) and imaged using a STORM imaging system, or also verified by Southern, dot or slot blot analysis using a labeled probe against the internal sequences of the PCR product. The probes also may be polynucleotides analogs, such as morpholinos or peptide nucleic acids analogs (PNAs). Detection of a product comprising a sequence selected from the group consisting of SEQUENCE ID NOS 1–8, and fragments or complements thereof, is indicative of the presence of PS133 mRNA(s), suggesting a diagnosis of a prostate tissue disease or condition, such as prostate cancer.

Example 9

OH-PCR

A. Probe selection and Labeling.

Target-specific primers and probes are designed to detect the above-described target sequences by oligonucleotide hybridization PCR. International Publication Nos WO 92/10505, published Jun. 25, 1992, and WO 92/11388, published Jul. 9, 1992, teach methods for labeling oligonucleotides at their 5' and 3' ends, respectively. According to one known method for labeling an oligonucleotide, a label-phosphoramidite reagent is prepared and used to add the label to the oligonucleotide during its synthesis. For example, see N. T. Thuong et al., *Tet. Letters* 29(46) :5905–5908 (1988); or J. S. Cohen et al., published U.S. patent application Ser. No. 07/246,688 (NTIS ORDER No. PAT-APPL-7-246,688) (1989). Preferably, probes are labeled at their 3' end to prevent participation in PCR and the formation of undesired extension products. For one step OH-PCR, the probe should have a $T_M$ at least 15° C. below the $T_M$ of the primers. The primers and probes are utilized as specific binding members, with or without detectable labels, using standard phosphoramidite chemistry and/or post-synthetic labeling methods which are well-known to one skilled in the art.

B. One Step Oligo Hybridization PCR.

OH-PCR is performed on a 200 μl reaction containing 50 mM (N,N,-bis[2-Hydroxyethyl]glycine), pH 8.15, 81.7 mM KOAc, 33.33 mM KOH, 0.01 mg/ml bovine serum albumin, 0.1 mM ethylene diaminetetraacetic acid, 0.02 mg/ml NaN$_3$, 8% w/v glycerol, 150 μM each of dNTP, 0.25 μM each primer, 3.75 nM probe, 5U rTth polymerase, 3.25 mM Mn(OAc)$_2$ and 5 μl blood equivalents of target (see Example 3). Since RNA and the rTth polymerase enzyme are unstable in the presence of Mn(OAc)$_2$, the Mn(OAc)$_2$ should be added just before target addition. The reaction is incubated in a Perkin-Elmer Thermal Cycler 480. Optimal conditions for cDNA synthesis and thermal cycling can be readily determined by those skilled in the art. Conditions which may be found useful include cDNA synthesis (60° C., 30 min), 30–45 amplification cycles (94° C., 40 sec; 55–70° C., 60 sec), oligo-hybridization (97° C., 5 min; 15° C., 5 min; 15° C. soak). The correct reaction product contains at least one of the strands of the PCR product and an internally hybridized probe.

C. OH-PCR Product Analysis.

Amplified reaction products are detected on an LCx® analyzer system (available from Abbott Laboratories, Abbott Park, Ill.). Briefly, the correct reaction product is captured by an antibody labeled microparticle at a capturable site on either the PCR product strand or the hybridization probe, and the complex is detected by binding of a detectable antibody conjugate to either a detectable site on the probe or the PCR strand. Only a complex containing a PCR strand hybridized with the internal probe is detectable. The detection of this complex then is indicative of the presence of PS133 mRNA, suggesting a diagnosis of a prostate disease or condition, such as prostate cancer.

Many other detection formats exist which can be used and/or modified by those skilled in the art to detect the presence of amplified or non-amplified PS133-derived nucleic acid sequences including, but not limited to, ligase chain reaction (LCR, Abbott Laboratories, Abbott Park, Ill.); Q-beta replicase (Gene-Trak™, Naperville, Ill.), branched chain reaction (Chiron, Emeryville, calif.) and strand displacement assays (Becton Dickinson, Research Triangle Park, N.C.).

Example 10

Synthetic Peptide Production

Synthetic peptides are modeled and then prepared based upon the predicted amino acid sequence of the PS133 polypeptide consensus sequence (see example 1). Peptides modeled for PS133 include SEQUENCE ID NO 25, SEQUENCE ID NO 26, SEQUENCE ID NO 27, and fragments thereof derived from SEQUENCE ID NO 24. All peptides are synthesized on a Symphony Peptide Synthesizer (available from Rainin Instrument Co, Emeryville Calif.) or similar instrument, using FMOC chemistry, standard cycles and in-situ HBTU activation. Cleavage and deprotection conditions are as follows: a volume of 2.5 ml of cleavage reagent (77.5% v/v trifluoroacetic acid, 15% v/v ethanedithiol, 2.5% v/v water, 5% v/v thioanisole, 1–2% w/v phenol) is added to the resin, and agitated at room temperature for 2–4 hours. Then the filtrate is removed and the peptide is precipitated from the cleavage reagent with cold diethyl ether. Each peptide is filtered, purified via reverse-phase preparative HPLC using a water/acetonitrile/0.1% TFA gradient, and lyophilized. The product is confirmed by mass spectrometry (see Example 12).

Disulfide bond formation is accomplished using auto-oxidation conditions, as follows: the peptide is dissolved in a minimum amount of DMSO (approximately 10 ml) before adding buffer (0.1M Tris-HCl, pH 6.2) to a concentration of 0.3–0.8 mg/ml. The reaction is monitored by HPLC until complete formation of the disulfide bond, followed by reverse-phase preparative HPLC using a water/acetonitrile/ 0.1% TFA gradient and lyophilization. The product then is confirmed by mass spectrometry (see Example 12).

The purified peptides can be conjugated to Keyhole Limpet Hemocyanin or other immunoreactive molecule with glutaraldehyde, mixed with adjuvant, and injected into animals.

Example 11a

Expression of Protein in a Cell Line Using Plasmid 577

A. Construction of a PS133 Expression Plasmid.

Plasmid 577, described in U.S. patent application Ser. No. 08/478,073, filed Jun. 7, 1995 and incorporated herein by reference, has been constructed for the expression of secreted antigens in a permanent cell line. This plasmid contains the following DNA segments: (a) a 2.3 Kb fragment of pBR322 containing bacterial beta-lactamase and origin of DNA replication; (b) a 1.8 Kb cassette directing expression of a neomycin resistance gene under control of HSV-1 thymidine kinase promoter and poly-A addition signals; (c) a 1.9 Kb cassette directing expression of a dihydrofolate reductase gene under the control of an SV-40 promoter and poly-A addition signals; (d) a 3.5 Kb cassette directing expression of a rabbit immunoglobulin heavy chain signal sequence fused to a modified hepatitis C virus (HCV) E2 protein under the control of the Simian Virus 40 T-Ag promoter and transcription enhancer, the hepatitis B virus surface antigen (HBsAg) enhancer I followed by a fragment of Herpes Simplex Virus-1 (HSV-1) genome providing poly-A addition signals; and (e) a residual 0.7 Kb fragment of Simian Virus 40 genome late region of no function in this plasmid. All of the segments of the vector were assembled by standard methods known to those skilled in the art of molecular biology.

Plasmids for the expression of secretable PS133 proteins are constructed by replacing the hepatitis C virus E2 protein coding sequence in plasmid 577 with that of a PS133 polynucleotide sequence selected from the group consisting of SEQUENCE ID NOS 1–8, and fragments or complements thereof, as follows. Digestion of plasmid 577 with XbaI releases the hepatitis C virus E2 gene fragment. The resulting plasmid backbone allows insertion of the PS133 cDNA insert downstream of the rabbit immunoglobulin heavy chain signal sequence which directs the expressed proteins into the secretory pathway of the cell. The PS133 cDNA fragment is generated by PCR using standard procedures. Encoded in the sense PCR primer sequence is an XbaI site, immediately followed by a 12 nucleotide sequence that encodes the amino acid sequence Ser-Asn-Glu-Leu ("SNEL") to promote signal protease processing, efficient secretion and final product stability in culture fluids. Immediately following this 12 nucleotide sequence the primer contains nucleotides complementary to template sequences encoding amino acids of the PS133 gene. The antisense primer incorporates a sequence encoding the following eight amino acids just before the stop codons: Asp-Tyr-Lys-Asp-Asp-Asp-Asp-Lys (SEQUENCE ID NO 75). Within this sequence is incorporated a recognition site to aid in analysis and purification of the PS133 protein product. A recognition site (termed "FLAG") that is recognized by a commercially available monoclonal antibody designated anti-FLAG M2 (Eastman Kodak, Co., New Haven, Conn.) can be utilized, as well as other comparable sequences and their corresponding antibodies. For example, PCR is performed using Gene-Ampl reagents obtained from Perkin-Elmer-Cetus, as directed by the supplier's instructions. PCR primers are used at a final concentration of 0.5 $\mu$M. PCR is performed on the PS133 plasmid template in a 100 $\mu$l reaction for 35 cycles (94° C., 30 seconds; 55° C., 30 seconds; 72° C., 90 seconds) followed by an extension cycle of 72° C. for 10 min.

B. Transfection of Dihydrofolate Reductase Deficient Chinese Hamster Ovary Cells.

The plasmid described supra is transfected into CHO/dhfr− cells (DXB-111, Uriacio et al., *PNAS* 77:4451–4466 (1980)). These cells are available from the A.T.C.C., 12301 Parklawn Drive, Rockville, Md. 20852, under Accession No. CRL 9096. Transfection is carried out using the cationic liposome-mediated procedure described by P. L. Felgner et al., *PNAS* 84:7413–7417 (1987). Particularly, CHO/dhfr− cells are cultured in Ham's F-12 media supplemented with 10% fetal calf serum, L-glutamine (1 mM) and freshly seeded into a flask at a density of 5–8×$10^5$ cells per flask. The cells are grown to a confluency of between 60 and 80% for transfection. Twenty micrograms (20 $\mu$g) of plasmid DNA is added to 1.5 ml of Opti-MEM I medium and 100 $\mu$l of Lipofectin Reagent (Gibco-BRL; Grand Island, N.Y.) are added to a second 1.5 ml portion of Opti-MEM I media. The two solutions are mixed and incubated at room temperature for 20 min. After the culture medium is removed from the cells, the cells are rinsed 3 times with 5 ml of Opti-MEM I medium. The Opti-MEM I-Lipofection-plasmid DNA solution then is overlaid onto the cells. The cells are incubated for 3 h at 37° C., after which time the Opti-MEM I-Lipofectin-DNA solution is replaced with culture medium for an additional 24 h prior to selection.

C. Selection and Amplification.

One day after transfection, cells are passaged 1:3 and incubated with dhfr/G418 selection medium (hereafter, "F-12 minus medium G"). Selection medium is Ham's F-12 with L-glutamine and without hypoxanthine, thymidine and glycine (JRH Biosciences, Lenexa, Kans.) and 300 $\mu$g per ml G418 (Gibco-BRL; Grand Island, N.Y.). Media volume-to-surface area ratios of 5 ml per 25 $cm^2$ are maintained. After approximately two weeks, DHFR/G418 cells are expanded to allow passage and continuous maintenance in F-12 minus medium G.

Amplification of each of the transfected PS133 cDNA sequences is achieved by stepwise selection of $DHFR^+$, $G418^+$ cells with methotrexate (reviewed by R. Schimke, *Cell* 37:705–713 [1984]). Cells are incubated with F-12 minus medium G containing 150 nM methotrexate (MTX) (Sigma, St. Louis, Mo.) for approximately two weeks until resistant colonies appear. Further gene amplification is achieved by selection of 150 nM adapted cells with 5 $\mu$M MTX.

D. Antigen Production.

F-12 minus medium G supplemented with 5 $\mu$M MTX is overlaid onto just confluent monolayers for 12 to 24 h at 37° C. in 5% $CO_2$. The growth medium is removed and the cells are rinsed 3 times with Dulbecco's phosphate buffered saline (PBS) (with calcium and magnesium) (Gibco-BRL; Grand Island, N.Y.) to remove the remaining media/serum which may be present. Cells then are incubated with VAS custom medium (VAS custom formulation with L-glutamine with HEPES without phenol red, available from JRH Bioscience; Lenexa, Kans., product number 52-08678P), for 1 h at 37° C. in 5% $CO_2$. Cells then are overlaid with VAS for production at 5 ml per T flask. Medium is removed after seven days of incubation, retained, and then frozen to await purification with harvests 2, 3 and 4. The monolayers are overlaid with VAS for 3 more seven day harvests.

E. Analysis of Prostate Tissue Gene PS133 Antigen Expression.

Aliquots of VAS supernatants from the cells expressing the PS133 protein construct are analyzed, either by SDS-polyacrylamide gel electrophoresis (SDS-PAGE) using standard methods and reagents known in the art (Laemmli discontinuous gels), or by mass spectrometry.

F. Purification.

Purification of the PS133 protein containing the FLAG sequence is performed by immunoaffinity chromatography using an affinity matrix comprising anti-FLAG M2 monoclonal antibody covalently attached to agarose by hydrazide linkage (Eastman Kodak Co., New Haven, Conn.). Prior to affinity purification, protein in pooled VAS medium harvests from roller bottles is exchanged into 50 mM Tris-HCl (pH 7.5), 150 mM NaCl buffer using a Sephadex G-25 (Pharmacia Biotech Inc., Uppsala, Sweden) column. Protein in this buffer is applied to the anti-FLAG M2 antibody affinity column. Non-binding protein is eluted by washing the column with 50 mM Tris-HCl (pH 7.5), 150 mM NaCl buffer. Bound protein is eluted using an excess of FLAG peptide in 50 mM Tris-HCl (pH 7.5), 150 mM NaCl. The excess FLAG peptide can be removed from the purified PS133 protein by gel electrophoresis or HPLC.

Although plasmid 577 is utilized in this example, it is known to those skilled in the art that other comparable expression systems, such as CMV, can be utilized herein with appropriate modifications in reagent and/or techniques and are within the skill of the ordinary artisan.

The largest cloned insert containing the coding region of the PS133 gene is then sub-cloned into either (i) a eukaryotic expression vector which may contain, for example, a cytomegalovirus (CMV) promoter and/or protein fusible sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in EPO 0196056, published Oct. 1, 1986, which is incorporated herein by reference and those containing fusion sequences of CKS are described in EPO Publication No. 0331961, published Sep. 13, 1989, which publication is also incorporated herein by reference. This so-purified protein can be used in a variety of techniques, including but not limited to animal immunization studies, solid phase immunoassays, etc.

Example 11b

Expression of Protein in a Cell Line Using pcDNA3.1/Myc-His

A. Construction of a PS133 Expression Plasmid.

Plasmid pcDNA3.1/Myc-His (Cat.#V855-20, Invitrogen, Carlsbad, Calif.) has been constructed, in the past, for the expression of secreted antigens by most mammalian cell lines. Expressed protein inserts are fused to a myc-his peptide tag. The myc-his tag is a 21 residue amino acid sequence having the following sequence: Glu-Gln-Lys-Leu-Ile-Ser-Glu-Glu-Asp-Leu-Asn-Met-His-Thr-Glu-His-His-His-His-His-His (SEQUENCE ID NO 76) and comprises a myc epitope and a polyhistidine sequence which are useful for the purification of an expressed fusion protein using either anti-myc or anti-his affinity columns, or metalloprotein binding columns.

Plasmids for the expression of secretable PS133 proteins are constructed by inserting a PS133 polynucleotide sequence selected from the group consisting of SEQUENCE ID NOS 1–8, and fragments or complements thereof. Prior to construction of a PS133 expression plasmid, the PS133 cDNA sequence is first cloned into a pCR®-Blunt vector as follows.

The PS133 cDNA fragment is generated by PCR using standard procedures. For example, PCR is performed using Stratagene® reagents obtained from Stratagene, La Jolla, Calif., as directed by the supplier's instructions. PCR primers are used at a final concentration of 0.5 $\mu$M. PCR using 5 U of pfu polymerase (Stratagene) is performed on the PS133 plasmid template (see Example 2) in a 50 $\mu$l reaction for 30 cycles (94° C., 1 min; 65° C., 1.5 min; 72° C., 3 min) followed by an extension cycle at 72° C. for 8 min. The sense PCR primer sequence comprises nucleotides which are either complementary to the pINCY vector directly upstream of the PS133 gene insert or which incorporate a 5' EcoRI restriction site, an adjacent downstream protein translation consensus initiator, and a 3' nucleic acid sequence which is the same sense as the 5'-most end of the PS133 cDNA insert. The antisense primer incorporates a 5' NotI restriction sequence and a sequence complementary to the 3' end of the PS133 cDNA insert just upstream of the 3'-most, in-frame stop codon. Five microliters (5 $\mu$l) of the resulting blunt-ended PCR product are ligated into 25 ng of linearized pCR®-Blunt vector (Invitrogen, Carlsbad, Calif.) interrupting the lethal ccdB gene of the vector. The resulting ligated vector is transfected into TOP10 E. coli (Invitrogen, Carlsbad, Calif.) using a One Shot™ transformation kit (Invitrogen, Carlsbad, Calif.) following the supplier's directions. The transfected cells are grown on LB-Kan (50 $\mu$g/ml kanamycin) selection plates at 37° C. Only cells containing a plasmid with an interrupted ccdB gene will grow after transfection (Grant, S.G.N., PNAS USA 87:4645–4649 (1990)). Transfected colonies are picked and grown up in 3 ml of LB-Kan broth at 37° C. Plasmid DNA is isolated using a QIAprep® (Qiagen Inc., Santa Clarita, Calif.) procedure, as directed by the supplier's instructions. The DNA is cut with EcoRI or SnaBI, and NotI restriction enzymes to release the PS133 insert fragment. The fragment is run on 1% Seakem® LE agarose/0.5 $\mu$g/ml ethidium bromide/TE gel, visualized by UV irradiation, excised and purified using QIAquic™ (Qiagen Inc., Santa Clarita, Calif.) procedures, as directed by the supplier's instructions.

The pcDNA3.1/Myc-His plasmid DNA is linearized by digestion with EcoRI or SnaBI, and NotI in the polylinker region of the plasmid DNA. The resulting plasmid DNA backbone allows insertion of the PS133 purified cDNA fragment, supra, downstream of a CMV promoter which directs expression of the proteins in mammalian cells. The ligated plasmid is transfected into DH5 alpha™ cells (GibcoBRL, Gaithersburg, Md.) as directed by the supplier's instructions. Briefly, 10 ng of pcDNA3.1/Myc-His containing a PS133 insert is added to 50 $\mu$l of competent DH5 alpha cells, and the contents are mixed gently. The mixture is incubated on ice for 30 min, heat shocked for 20 sec at 37° C., and placed on ice for an additional 2 min. Upon addition of 0.95 ml of LB medium, the mixture is incubated for 1 h at 37° C. while shaking at 225 rpm. The transfected cells are then plated onto 100 mm LB/Amp (50 $\mu$g/ml ampicillin) plates and grown at 37° C. Colonies are picked and grown in 3 ml of LB/Amp broth. Plasmid DNA is purified using a QIAprep® kit. Presence of the insert is confirmed using techniques known to those skilled in the art including, but not limited to, restriction digestion and gel analysis. See, e.g., J. Sambrook et al., supra.

B. Transfection of Human Embryonic Kidney 293 Cells.

The PS133 expression plasmid described supra is transfected into HEK293 cells (F. L. Graham et al., J. Gen. Vir.36:59–72 (1977)). These cells are available from the A.T.C.C., 12301 Parklawn Drive, Rockville, Md. 20852, under Accession No. CRL 1573. Transfection is carried out using the cationic lipofectamine-mediated procedure described by P. Hawley-Nelson et al., Focus 15:73 (1993). Particularly, HEK293 cells are cultured in 10 ml DMEM media supplemented with 10% fetal bovine serum (FBS), L-glutamine (2 mM) and freshly seeded into 100 mm culture plates at a density of $9 \times 10^6$ cells per plate. The cells are grown at 37° C. to a confluency of between 70% and 80% for transfection. Eight micrograms (8 $\mu$g) of plasmid DNA is added to 800 $\mu$l of Opti-MEM I® medium (Gibco-BRL, Grand Island, N.Y.), and 48–96 $\mu$l of Lipofectamine™ Reagent (Gibco-BRL, Grand Island, N.Y.) is added to a second 800 $\mu$l portion of Opti-MEM I® media. The two solutions are mixed and incubated at room temperature for 15–30 min. After the culture medium is removed from the cells, the cells are washed once with 10 ml of serum-free DMEM. The Opti-MEM I®-Lipofectamine-plasmid DNA solution is diluted in 6.4 ml of serum-free DMEM and then overlaid onto the cells. The cells are incubated for 5 h at 37° C., after which time, an additional 8 ml of DMEM with 20% FBS is added. After 18–24 h, the old medium is aspirated, and the cells are overlaid with 5 ml of fresh DMEM with 10% FBS. Supernatants and cell extracts are analyzed for PS133 gene activity 72 h after transfection.

C. Analysis of Prostate Tissue Gene PS133 Antigen Expression.

The culture supernatant, supra, is transferred to cryotubes and stored on ice. HEK293 cells are harvested by washing twice with 10 ml cold Dulbecco's PBS and lysing by addition of 1.5 ml of CAT lysis buffer (Boehringer Mannheim, Indianapolis, Ind.), followed by incubation for 30 min at room temperature. Lysate is transferred to 1.7 ml polypropylene microfuge tubes and centrifuged at 1000×g for 10 min. The supernatant is transferred to new cryotubes and stored on ice. Aliquots of cell supernatants and the lysate of the cells expressing the PS133 protein construct are analyzed for the presence of PS133 recombinant protein. The aliquots can be analyzed using SDS-polyacrylamide gel electrophoresis (SDS-PAGE), using standard methods and reagents known in the art. See, e.g., J. Sambrook et al., supra. The gels can then be blotted onto a solid medium such as nitrocellulose, nytran, or the like, and the PS133 protein band can be visualized using western blotting techniques with anti-myc epitope or anti-histidine monoclonal antibodies (Invitrogen, Carlsbad, Calif.) or PS133 polyclonal serum (see Example 14). Alternatively, the expressed PS133 recombinant protein can be analyzed by mass spectrometry (see Example 12).

D. Purification.

Purification of the PS133 recombinant protein containing the myc-his sequence is performed using the Xpress® affinity chromatography system (Invitrogen, Carlsbad, Calif.) containing a nickel-charged agarose resin which specifically binds polyhistidine residues. Supernatants from 10 ×100 mm plates, prepared as described supra, are pooled and passed over the nickel-charged column. Non-binding protein is eluted by washing the column with 50 mM Tris-HCl (pH 7.5)/150 mM NaCl buffer, leaving only the myc-his fusion proteins. Bound PS133 recombinant protein then is eluted from the column using either an excess of imidazole or histidine, or a low pH buffer. Alternatively, the recombinant protein can also be purified by binding at the myc-his sequence to an affinity column consisting of either anti-myc or anti-histidine monoclonal antibodies conjugated through a hydrazide or other linkage to an agarose resin and eluting with an excess of myc peptide or histidine, respectively.

The purified recombinant protein can then be covalently cross-linked to a solid phase, such as N-hydroxysuccinimide-activated sepharose columns (Pharmacia Biotech, Piscataway, N.J.), as directed by supplier's instructions. These columns containing covalently linked PS133 recombinant protein, can then be used to purify anti-PS133 antibodies from rabbit or mouse sera (see Examples 13 and 14).

E. Coating Microtiter Plates with PS133 Expressed Proteins.

Supernatant from a 100 mm plate, as described supra, is diluted in an appropriate volume of PBS. 100 µl of the resulting mixture is placed into each well of a Reacti-Bind™ metal chelate microtiter plate (Pierce, Rockford, Ill.), incubated at room temperature while shaking, and followed by three washes with 200 µl each of PBS with 0.05% Tweene® 20. The prepared microtiter plate can then be used to screen polyclonal antisera for the presence of anti-PS133 antibodies (see Example 17).

Although pcDNA3.1/Myc-His is utilized in this example, it is known to those skilled in the art that other comparable expression systems can be utilized herein with appropriate modifications in reagent and/or techniques and are within the skill of one of ordinary skill in the art. The largest cloned insert containing the coding region of the PS133 gene is sub-cloned into either (i) a eukaryotic expression vector which may contain, for example, a cytomegalovirus (CMV) promoter and/or protein fusible sequences which aid in protein expression and detection, or (ii) a bacterial expression vector containing a superoxide-dismutase (SOD) and CMP-KDO synthetase (CKS) or other protein fusion gene for expression of the protein sequence. Methods and vectors which are useful for the production of polypeptides which contain fusion sequences of SOD are described in European patent application No. EP 0 196 056, published Oct. 1, 1986, which is incorporated herein by reference, and vectors containing fusion sequences of CKS are described in European patent application No. EP 0 331 961, published Sep. 13, 1989, which publication is also incorporated herein by reference. The purified protein can be used in a variety of techniques, including but not limited to, animal immunization studies, solid phase immunoassays, etc.

Example 12

Chemical Analysis of Prostate Tissue Proteins

A. Analysis of Tryptic Peptide Fragments Using MS.

Sera from patients with prostate disease such as prostate cancer, sera from patients with no prostate disease, extracts of prostate tissues or cells from patients with prostate disease such as prostate cancer, extracts of prostate tissues or cells from patients with no prostate disease, and extracts of tissues or cells from other non-diseased or diseased organs of patients, are run on a polyacrylamide gel using standard procedures and stained with Coomassie Blue. Sections of the gel suspected of containing the unknown polypeptide are excised and subjected to an in-gel reduction, acetamidation and tryptic digestion. P. Jeno et al., Anal. Bio. 224:451–455 (1995) and J. Rosenfeld et al., Anal. Bio. 203:173–179 (1992). The gel sections are washed with 100 mM $NH_4HCO_3$ and acetonitrile. The shrunken gel pieces are swollen in digestion buffer (50 mM $NH_4HCO_3$, 5 mM $CaCl_2$ and 12.5 µg/ml trypsin) at 4° C. for 45 min. The supernatant is aspirated and replaced with 5 to 10 µl of digestion buffer without trypsin and allowed to incubate overnight at 37° C. Peptides are extracted with 3 changes of 5% formic acid and acetonitrile and evaporated to dryness. The peptides are adsorbed to approximately 0.1 µl of POROS R2 sorbent (Perseptive Biosystems, Framingham, Mass.) trapped in the tip of a drawn gas chromatography capillary tube by dissolving them in 10 µl of 5% formic acid and passing it through the capillary. The adsorbed peptides are washed with water and eluted with 5% formic acid in 60% methanol. The eluant is passed directly into the spraying capillary of an API III mass spectrometer (Perkin-Elmer Sciex, Thornhill, Ontario, Canada) for analysis by nano-electrospray mass spectrometry. M. Wilm et al., Int. J. Mass Spectrom. Ion Process 136:167–180 (1994) and M. Wilm et al., Anal. Chem. 66:1–8 (1994). The masses of the tryptic peptides are determined from the mass spectrum obtained off the first quadrupole. Masses corresponding to predicted peptides can be further analyzed in MS/MS mode to give the amino acid sequence of the peptide.

B. Peptide Fragment Analysis Using LC/MS.

The presence of polypeptides predicted from mRNA sequences found in hyperplastic disease tissues also can be confirmed using liquid chromatography/tandem mass spectrometry (LC/MS/MS). D. Hess et al., METHODS, A Companion to Methods in Enzymology 6:227–238 (1994). The serum specimen or tumor extract from the patient is denatured with SDS and reduced with dithiothreitol (1.5 mg/ml) for 30 min at 90° C. followed by alkylation with iodoacetamide (4 mg/ml) for 15 min at 25° C. Following acrylamide electrophoresis, the polypeptides are electroblotted to a cationic membrane and stained with Coomassie Blue. Following staining, the membranes are washed and sections thought to contain the unknown polypeptides are cut out and dissected into small pieces. The membranes are placed in 500 µl microcentrifuge tubes and immersed in 10 to 20 µl of proteolytic digestion buffer (100 mM Tris-HCl, pH 8.2, containing 0.1M NaCl, 10% acetonitrile, 2 mM $CaCl_2$ and 5 µg/ml trypsin) (Sigma, St. Louis, Mo.). After 15 h at 37° C., 3 µl of saturated urea and 1 µl of 100 µg/ml trypsin are added and incubated for an additional 5 h at 37° C. The digestion mixture is acidified with 3 µl of 10% trifluoroacetic acid and centrifuged to separate supernatant from membrane. The supernatant is injected directly onto a microbore, reverse phase HPLC column and eluted with a linear gradient of acetonitrile in 0.05% trifluoroacetic acid. The eluate is fed directly into an electrospray mass spectrometer, after passing though a stream splitter if necessary to adjust the volume of material. The data is analyzed following the procedures set forth in Example 12, Section A.

Example 13

Gene Immunization Protocol

A. In Vivo Antigen Expression.

Gene immunization circumvents protein purification steps by directly expressing an antigen in vivo after inoculation of the appropriate expression vector. Also, production of antigen by this method may allow correct protein folding and glycosylation since the protein is produced in mammalian tissue. The method utilizes insertion of the gene sequence into a plasmid which contains a CMV promoter, expansion and purification of the plasmid and injection of the plasmid DNA into the muscle tissue of an animal. Preferred animals include mice and rabbits. See, for example, H. Davis et al., *Human Molecular Genetics* 2:1847–1851 (1993). After one or two booster immunizations, the animal can then be bled, ascites fluid collected, or the animal's spleen can be harvested for production of hybridomas.

B. Plasmid Preparation and Purification.

PS133 cDNA sequences are generated from the PS133 cDNA-containing vector using appropriate PCR primers containing suitable 5' restriction sites following the procedures described in Example 11. The PCR product is cut with appropriate restriction enzymes and inserted into a vector which contains the CMV promoter (for example, pRc/CMV or pcDNA3 vectors from Invitrogen, San Diego, Calif.). This plasmid then is expanded in the appropriate bacterial strain and purified from the cell lysate using a CsCl gradient or a Qiagen plasmid DNA purification column. All these techniques are familiar to one of ordinary skill in the art of molecular biology.

C. Immunization Protocol.

Anesthetized animals are immunized intramuscularly with 0.1–100 μg of the purified plasmid diluted in PBS or other DNA uptake enhancers (Cardiotoxin, 25% sucrose). See, for example, H. Davis et al., *Human Gene Therapy* 4:733–740 (1993); and P. W. Wolff et al., *Biotechniques* 11:474–485 (1991). One to two booster injections are given at monthly intervals.

D. Testing and Use of Antiserum.

Animals are bled and the resultant sera tested for antibody using peptides synthesized from the known gene sequence (see Example 16) using techniques known in the art, such as western blotting or EIA techniques. Antisera produced by this method can then be used to detect the presence of the antigen in a patient's tissue or cell extract, or in a patient's serum, by ELISA or Western blotting techniques, such as those described in Examples 15 through 18.

Example 14

Production of Antibodies Against PS133

A. Production of Polyclonal Antisera.

Antiserum against PS133 is prepared by injecting appropriate animals with peptides whose sequences are derived from that of the predicted amino acid sequence of the PS133 consensus sequence (SEQUENCE ID NO 7). The synthesis of peptides (SEQUENCE ID NO 25, SEQUENCE ID NO 26, and SEQUENCE ID NO 27) is described in Example 10. Peptides used as immunogen either can be conjugated to a carrier such as keyhole limpet hemocyanine (KLH), prepared as described hereinbelow, or unconjugated (i.e., not conjugated to a carrier such as KLH).

1. Peptide Conjugation. Peptide is conjugated to maleimide activated keyhole limpet hemocyanine (KLH, commercially available as Imject®, available from Pierce Chemical Company, Rockford, Ill.). Imjecte contains about 250 moles of reactive maleimide groups per mole of hemocyanine. The activated KLH is dissolved in phosphate buffered saline (PBS, pH 8.4) at a concentration of about 7.7 mg/ml. The peptide is conjugated through cysteines occurring in the peptide sequence, or to a cysteine previously added to the synthesized peptide in order to provide a point of attachment. The peptide is dissolved in dimethyl sulfoxide (DMSO, Sigma Chemical Company, St. Louis, Mo.) and reacted with the activated KLH at a mole ratio of about 1.5 moles of peptide per mole of reactive maleimide attached to the KLH. A procedure for the conjugation of peptide (SEQUENCE ID NO 25) is provided hereinbelow. It is known to the ordinary artisan that the amounts, times and conditions of such a procedure can be varied to optimize peptide conjugation.

The conjugation reaction described hereinbelow is based on obtaining 3 mg of KLH peptide conjugate ("conjugated peptide"), which contains about 0.77 μmoles of reactive maleimide groups. This quantity of peptide conjugate usually is adequate for one primary injection and four booster injections for production of polyclonal antisera in a rabbit. Briefly, peptide (SEQUENCE ID NO 25) is dissolved in DMSO at a concentration of 1.16 μmoles/100 μl of DMSO. One hundred microliters (100 μl) of the DMSO solution is added to 380 μl of the activated KLH solution prepared as described hereinabove, and 20 μl of PBS (pH 8.4) is added to bring the volume to 500 μl. The reaction is incubated overnight at room temperature with stirring. The extent of reaction is determined by measuring the amount of unreacted thiol in the reaction mixture. The difference between the starting concentration of thiol and the final concentration is assumed to be the concentration of peptide which has coupled to the activated KLH. The amount of remaining thiol is measured using Ellman's reagent (5,5'-dithiobis(2-nitrobenzoic acid), Pierce Chemical Company, Rockford, Ill.). Cysteine standards are made at a concentration of 0, 0.1, 0.5, 2, 5 and 20 mM by dissolving 35 mg of cysteine HCl (Pierce Chemical Company, Rockford, Ill.) in 10 ml of PBS (pH 7.2) and diluting the stock solution to the desired concentration(s). The photometric determination of the concentration of thiol is accomplished by placing 200 μl of PBS (pH 8.4) in each well of an Immulon 2® microwell plate (Dynex Technologies, Chantilly, Va.). Next, 10 μl of standard or reaction mixture is added to each well. Finally, 20 μl of Ellman's reagent at a concentration of 1 mg/ml in PBS (pH 8.4) is added to each well. The wells are incubated for 10 minutes at room temperature, and the absorbance of all wells is read at 415 nm with a microplate reader (such as the BioRad Model 3550, BioRad, Richmond, Calif.). The absorbance of the standards is used to construct a standard curve and the thiol concentration of the reaction mixture is determined from the standard curve. A decrease in the concentration of free thiol is indicative of a successful conjugation reaction. Unreacted peptide is removed by dialysis against PBS (pH 7.2) at room temperature for 6 hours. The conjugate is stored at 2–8° C. if it is to be used immediately; otherwise, it is stored at −20° C. or colder.

2. Animal Immunization. Female white New Zealand rabbits weighing 2 kg or more are used for raising polyclonal antiserum. Generally, one animal is immunized per unconjugated or conjugated peptide (prepared as described hereinabove). One week prior to the first immunization, 5 to 10 ml of blood is obtained from the animal to serve as a non-immune prebleed sample.

Unconjugated or conjugated peptide is used to prepare the primary immunogen by emulsifying 0.5 ml of the peptide at a concentration of 2 mg/ml in PBS (pH 7.2) which contains 0.5 ml of complete Freund's adjuvant (CFA) (Difco, Detroit, Mich.). The immunogen is injected into several sites of the animal via subcutaneous, intraperitoneal, and/or intramuscular routes of administration. Four weeks following the primary immunization, a booster immunization is administered. The immunogen used for the booster immunization dose is prepared by emulsifying 0.5 ml of the same unconjugated or conjugated peptide used for the primary immunogen, except that the peptide now is diluted to 1 mg/ml with 0.5 ml of incomplete Freund's adjuvant (IFA) (Difco, Detroit, Mich.). Again, the booster dose is administered into several sites and can utilize subcutaneous, intraperitoneal and intramuscular types of injections. The animal is bled (5 ml) two weeks after the booster immunization and the serum is tested for immunoreactivity to the peptide, as described below. The booster and bleed schedule is repeated at 4 week intervals until an adequate titer is obtained. The titer or concentration of antiserum is determined by microtiter EIA as described in Example 17, below. An antibody titer of 1:500 or greater is considered an adequate titer for further use and study.

B. Production of Monoclonal Antibody.

1. Immunization Protocol. Mice are immunized using immunogens prepared as described hereinabove, except that the amount of the unconjugated or conjugated peptide for monoclonal antibody production in mice is one-tenth the amount used to produce polyclonal antisera in rabbits. Thus, the primary immunogen consists of 100 $\mu$g of unconjugated or conjugated peptide in 0.1 ml of CFA emulsion; while the immunogen used for booster immunizations consists of 50 $\mu$g of unconjugated or conjugated peptide in 0.1 ml of IFA. Hybridomas for the generation of monoclonal antibodies are prepared and screened using standard techniques. The methods used for monoclonal antibody development follow procedures known in the art such as those detailed in Kohler and Milstein, *Nature* 256:494 (1975) and reviewed in J. G. R. Hurrel, ed., *Monoclonal Hybridoma Antibodies: Techniques and Applications*, CRC Press, Inc., Boca Raton, Fla. (1982). Another method of monoclonal antibody development which is based on the Kohler and Milstein method is that of L. T. Mimms et al., *Virology* 176:604–619 (1990), which is incorporated herein by reference.

The immunization regimen (per mouse) consists of a primary immunization with additional booster immunizations. The primary immunogen used for the primary immunization consists of 100 $\mu$g of unconjugated or conjugated peptide in 50 $\mu$l of PBS (pH 7.2) previously emulsified in 50 $\mu$l of CFA. Booster immunizations performed at approximately two weeks and four weeks post primary immunization consist of 50 $\mu$g of unconjugated or conjugated peptide in 50 $\mu$l of PBS (pH 7.2) emulsified with 50 $\mu$l IFA. A total of 100 $\mu$g of this immunogen is inoculated intraperitoneally and subcutaneously into each mouse. Individual mice are screened for immune response by microtiter plate enzyme immunoassay (EIA) as described in Example 17 approximately four weeks after the third immunization. Mice are inoculated either intravenously, intrasplenically or intraperitoneally with 50 $\mu$g of unconjugated or conjugated peptide in PBS (pH 7.2) approximately fifteen weeks after the third immunization.

Three days after this intravenous boost, splenocytes are fused with, for example, Sp2/0-Ag14 myeloma cells (Milstein Laboratories, England) using the polyethylene glycol (PEG) method. The fusions are cultured in Iscove's Modified Dulbecco's Medium (IMDM) containing 10% fetal calf serum (FCS), plus 1% hypoxanthine, aminopterin and thymidine (HAT). Bulk cultures are screened by microtiter plate EIA following the protocol in Example 17. Clones reactive with the peptide used an immunogen and non-reactive with other peptides (i.e., peptides of PS133 not used as the immunogen) are selected for final expansion. Clones thus selected are expanded, aliquoted and frozen in IMDM containing 10% FCS and 10% dimethyl-sulfoxide.

2. Production of Ascites Fluid Containing Monoclonal Antibodies. Frozen hybridoma cells prepared as described hereinabove are thawed and placed into expansion culture. Viable hybridoma cells are inoculated intraperitoneally into Pristane treated mice. Ascitic fluid is removed from the mice, pooled, filtered through a 0.2 $\mu$filter and subjected to an immunoglobulin class G (IgG) analysis to determine the volume of the Protein A column required for the purification.

3. Purification of Monoclonal Antibodies From Ascites Fluid. Briefly, filtered and thawed ascites fluid is mixed with an equal volume of Protein A sepharose binding buffer (1.5M glycine, 3.0M NaCl, pH 8.9) and refiltered through a 0.2$\mu$ filter. The volume of the Protein A column is determined by the quantity of IgG present in the ascites fluid. The eluate then is dialyzed against PBS (pH 7.2) overnight at 2–8° C. The dialyzed monoclonal antibody is sterile filtered and dispensed in aliquots. The immunoreactivity of the purified monoclonal antibody is confirmed by determining its ability to specifically bind to the peptide used as the immunogen by use of the EIA ricrotiter plate assay procedure of Example 17. The specificity of the purified monoclonal antibody is confirmed by determining its lack of binding to irrelevant peptides such as peptides of PS133 not used as the immunogen. The purified anti-PS133 monoclonal thus prepared and characterized is placed at either 2–8° C. for short term storage or at −80° C. for long term storage.

4. Further Characterization of Monoclonal Antibody. The isotype and subtype of the monoclonal antibody produced as described hereinabove can be determined using commercially available kits (available from Amersham. Inc., Arlington Heights, Ill.). Stability testing also can be performed on the monoclonal antibody by placing an aliquot of the monoclonal antibody in continuous storage at 2–8° C. and assaying optical density (OD) readings throughout the course of a given period of time.

C. Use of Recombinant Proteins as Immunogens.

It is within the scope of the present invention that recombinant proteins made as described herein can be utilized as immunogens in the production of polyclonal and monoclonal antibodies, with corresponding changes in reagents and techniques known to those skilled in the art.

Example 15

Purification of Serum Antibodies Which Specifically Bind to PS133 Peptides

Irmune sera, obtained as described hereinabove in Examples 13 and/or 14, is affinity purified using immobilized synthetic peptides prepared as described in Example 10, or recombinant proteins prepared as described in Example 11. An IgG fraction of the antiserum is obtained by passing the diluted, crude antiserum over a Protein A column (Affi-Gel protein A, Bio-Rad, Hercules, Calif.). Elution with a buffer (Binding Buffer, supplied by the manufacturer) removes substantially all proteins that are not immunoglobulins. Elution with 0.1M buffered glycine (pH 3) gives an immunoglobulin preparation that is substantially free of albumin and other serum proteins.

Immunoaffinity chromatography is performed to obtain a preparation with a higher fraction of specific antigen-binding antibody. The peptide used to raise the antiserum is immobilized on a chromatography resin, and the specific antibodies directed against its epitopes are adsorbed to the resin. After washing away non-binding components, the specific antibodies are eluted with 0.1M glycine buffer, pH 2.3. Antibody fractions are immediately neutralized with 1.0M Tris buffer (pH 8.0) to preserve immunoreactivity. The chromatography resin chosen depends on the reactive groups present in the peptide. If the peptide has an amino group, a resin such as Affi-Gel 10 or Affi-Gel 15 is used (Bio-Rad, Hercules, Calif.). If coupling through a carboxy group on the peptide is desired, Affi-Gel 102 can be used (Bio-Rad, Hercules, Calif.). If the peptide has a free sulfhydryl group, an organomercurial resin such as Affi-Gel 501 can be used (Bio-Rad, Hercules, Calif.).

Alternatively, spleens can be harvested and used in the production of hybridomas to produce monoclonal antibodies following routine methods known in the art as described hereinabove.

Example 16

Western Blotting of Tissue Samples

Protein extracts are prepared by homogenizing tissue samples in 0.1M Tris-HCl (pH 7.5), 15% (w/v) glycerol, 0.2 mM EDTA, 1.0 mM 1,4-dithiothreitol, 10 µg/ml leupeptin and 1.0 mM phenylmethylsulfonylfluoride (Kain et al., *Biotechniques*, 17:982 (1994)). Following homogenization, the homogenates are centrifuged at 4° C. for 5 minutes to separate supernate from debris. For protein quantitation, 3–10 µl of supernate are added to 1.5 ml of bicinchoninic acid reagent (Sigma, St. Louis, Mo.), and the resulting absorbance at 562 nm is measured.

For SDS-PAGE, samples are adjusted to desired protein concentration with Tricine Buffer (Novex, San Diego, Calif.), mixed with an equal volume of 2×Tricine sample buffer (Novex, San Diego, Calif.), and heated for 5 minutes at 100° C. in a thermal cycler. Samples are then applied to a Novex 10–20% Precast Tricine Gel for electrophoresis. Following electrophoresis, samples are transferred from the gels to nitrocellulose membranes in Novex Tris-Glycine Transfer buffer. Membranes are then probed with specific anti-peptide antibodies using the reagents and procedures provided in the Western Lights or Western Lights Plus (Tropix, Bedford, Mass.) chemiluminesence detection kits. Chemiluminescent bands are visualized by exposing the developed membranes to Hyperfilm ECL (Amersham, Arlington Heights, Ill.).

Competition experiments are carried out in an analogous manner as above, with the following exception; the primary antibodies (anti-peptide polyclonal antisera) are pre-incubated for 30 minutes at room temperature with varying concentrations of peptide immunogen prior to exposure to the nitrocellulose filter. Development of the Western is performed as above.

After visualization of the bands on film, the bands can also be visualized directly on the membranes by the addition and development of a chromogenic substrate such as 5-bromo-4-chloro-3-indolyl phosphate (BCIP). This chromogenic solution contains 0.016% BCIP in a solution containing 100 mM NaCl, 5 mM MgCl$_2$ and 100 mM Tris-HCl (pH 9.5). The filter is incubated in the solution at room temperature until the bands develop to the desired intensity. Molecular mass determination is made based upon the mobility of pre-stained molecular weight standards (Novex, San Diego, Calif.) or biotinylated molecular weight standards (Tropix, Bedford, Mass.).

Example 17

EIA Microtiter Plate Assay

The immunoreactivity of antiserum preferably obtained from rabbits or mice as described in Example 13 or Example 14 is determined by means of a microtiter plate EIA, as follows. Synthetic peptides prepared as described in Example 10 or recombinant proteins prepared as described in Example 11 are dissolved in 50 mM carbonate buffer (pH 9.6) to a final concentration of 2 µg/ml. Next, 100 µl of the peptide or protein solution is placed in each well of an Immulon 2® microtiter plate (Dynex Technologies, Chantilly, Va.). The plate is incubated overnight at room temperature and then washed four times with deionized water. The wells are blocked by adding 125 µl of a suitable protein blocking agent, such as Superblock® (Pierce Chemical Company, Rockford, Ill.), in phosphate buffered saline (PBS, pH 7.4) to each well and then immediately discarding the solution. This blocking procedure is performed three times. Antiserum obtained from immunized rabbits or mice prepared as previously described is diluted in a protein blocking agent (e.g., a 3% Superblock® solution) in PBS containing 0.05% Tween–20® (monolaurate polyoxyethylene ether) (Sigma Chemical Company, St. Louis, Mo.) and 0.05% sodium azide at dilutions of 1:500, 1:2500, 1:12,500, 1:62,500 and 1:312,500 and placed in each well of the coated microtiter plate. The wells then are incubated for three hours at room temperature. Each well is washed four times with deionized water. One hundred µl of alkaline phosphatase-conjugated goat anti-rabbit IgG or goat anti-mouse IgG antiserum (Southern Biotech, Birmingham, Ala.), diluted 1:2000 in 3% Superblock® solution in phosphate buffered saline containing 0.05% Tween 20® and 0.05% sodium azide, is added to each well. The wells are incubated for two hours at room temperature. Next, each well is washed four times with 5 deionized water. One hundred microliters (100 µl) of paranitrophenyl phosphate substrate (Kirkegaard and Perry Laboratories, Gaithersburg, Md.) then is added to each well. The wells are incubated for thirty minutes at room temperature. The absorbance at 405 nm is read of each well. Positive reactions are identified by an increase in absorbance at 405 nm in the test well above that absorbance given by a non-immune serum (negative control). A positive reaction is indicative of the presence of detectable anti-PS133 antibodies.

In addition to titers, apparent affinities [K$_d$(app)] may also be determined for some of the anti-peptide antisera. EIA microtiter plate assay results can be used to derive the apparent dissociation constants (K$_d$) based on an analog of the Michaelis-Menten equation (V. Van Heyningen, *Methods in Enzymology*, Vol. 121, p. 472 (1986) and further described in X. Qiu et al., *Journal of Immunology*, Vol. 156, p. 3350 (1996)):

$$[Ag\text{-}Ab] = [Ag\text{-}Ab]_{max} \times \frac{[Ab]}{[Ab] = K_d}$$

Where [Ag–Ab] is the antigen-antibody complex concentration, [Ag–Ab]$_{max}$ is the maximum complex concentration, [Ab] is the antibody concentration, and K$_d$ is the dissociation constant. During the curve fitting, the [Ag–Ab] is replaced with the background subtracted value of the OD$_{405nm}$ at the given concentration of Ab. Both K$_d$ and [OD$_{405nm}$]$_{max}$, which corresponds to the [Ag–Ab]$_{max}$, are treated as fitted parameters. The software program Origin can be used for the curve fitting.

Example 18

Coating of Solid Phase Particles

A. Coating of Microparticles with Antibodies Which Specifically Bind to PS133 Antigen.

Affinity purified antibodies which specifically bind to PS133 protein (see Example 15) are coated onto microparticles of polystyrene, carboxylated polystyrene, polymethylacrylate or similar particles having a radius in the range of about 0.1 to 20 μm. Microparticles may be either passively or actively coated. One coating method comprises coating EDAC (1-(3-dimethylaminopropyl)-3-ethylcarbodiimide hydrochloride (Aldrich Chemical Co., Milwaukee, Wis.) activated carboxylated latex microparticles with antibodies which specifically bind to PS133 protein, as follows. Briefly, a final 0.375% solid suspension of resin washed carboxylated latex microparticles (available from Bangs Laboratories, Carmel, Ind. or Serodyn, Indianapolis, Ind.) are mixed in a solution containing 50 mM MES buffer, pH 4.0 and 150 μm/gl of affinity purified anti-PS133 antibody (see Example 14) for 15 min in an appropriate container. EDAC coupling agent is added to a final concentration of 5.5 μg/ml to the mixture and mixed for 2.5 h at room temperature.

The microparticles then are washed with 8 volumes of a Tween 20®/sodium phosphate wash buffer (pH 7.2) by tangential flow filtration using a 0.2 μm Microgon Filtration module. Washed microparticles are stored in an appropriate buffer which usually contains a dilute surfactant and irrelevant protein as a blocking agent, until needed.

B. Coating of ¼ Inch Beads.

Antibodies which specifically bind to PS133-antigen also may be coated on the surface of ¼ inch polystyrene beads by routine methods known in the art (Snitman et al., U.S. Pat. No. 5,273,882, incorporated herein by reference) and used in competitive binding or EIA sandwich assays.

Polystyrene beads first are cleaned by ultrasonicating them for about 15 seconds in 10 mM NaHCO$_3$ buffer at pH 8.0. The beads then are washed in deionized water until all fines are removed. Beads then are immersed in an antibody solution in 10 mM carbonate buffer, pH 8 to 9.5. The antibody solution can be as dilute as 1 μg/ml in the case of high affinity monoclonal antibodies or as concentrated as about 500 μg/ml for polyclonal antibodies which have not been affinity purified. Beads are coated for at least 12 hours at room temperature, and then they are washed with deionized water. Beads may be air dried or stored wet (in PBS, pH 7.4). They also may be overcoated with protein stabilizers (such as sucrose) or protein blocking agents used as non-specific binding blockers (such as rrelevant proteins, Carnation skim milk, Superblock®, or the like).

Example 19

Microparticle Enzyme Immunoassay (MEIA)

PS133 antigens are detected in patient test samples by performing a standard ntigen competition EIA or antibody sandwich EIA and utilizing a solid phase such s microparticles (MEIA). The assay can be performed on an automated analyzer uch as the IMx® Analyzer (Abbott Laboratories, Abbott Park, Ill.).

A. Antibody Sandwich EIA.

Briefly, samples suspected of containing PS133 antigen are incubated in the presence of anti-PS133 antibody-coated microparticles (prepared as described in Example 17) in order to form antigen/antibody complexes. The microparticles then are washed and an indicator reagent comprising an antibody conjugated to a signal generating compound (i.e., enzymes such as alkaline phosphatase or horseradish peroxide) is added to the antigen/antibody complexes or the microparticles and incubated. The microparticles are washed and the bound antibody/antigen/antibody complexes are detected by adding a substrate (e.g., 4-methyl umbelliferyl phosphate (MUP), or OPD/peroxide, respectively), that reacts with the signal generating compound to generate a measurable signal. An elevated signal in the test sample, compared to the signal generated by a negative control, detects the presence of PS133 antigen. The presence of PS133 antigen in the test sample is indicative of a diagnosis of a prostate disease or condition, such as prostate cancer.

B. Competitive Binding Assay.

The competitive binding assay uses a peptide or protein that generates a measurable signal when the labeled peptide is contacted with an anti-peptide antibody coated microparticle. This assay can be performed on the IMx® Analyzer (available from Abbott Laboratories, Abbott Park, Ill.). The labeled peptide is added to the PS133 antibody-coated microparticles (prepared as described in Example 17) in the presence of a test sample suspected of containing PS133 antigen, and incubated for a time and under conditions sufficient to form labeled PS133 peptide (or labeled protein)/bound antibody complexes and/or patient PS133 antigen/bound antibody complexes. The PS133 antigen in the test sample competes with the labeled PS133 peptide (or PS133 protein) for binding sites on the microparticle. PS133 antigen in the test sample results in a lowered binding of labeled peptide and antibody coated microparticles in the assay since antigen in the test sample and the PS133 peptide or PS133 protein compete for antibody binding sites. A lowered signal (compared to a control) indicates the presence of PS133 antigen in the test sample. The presence of PS133 antigen suggests the diagnosis of a prostate disease or condition, such as prostate cancer.

Example 20

Identifying Inhibitors of PS133 Proteolytic Activity

Inhibitors of the biological (catalytic) activity of PS133 polypeptides are discovered using peptide-based substrates which are conjugated with a chromogenic or fluorogenic tag. Such a peptide substrate has the following structure:

X-(Y)$_n$-Z, wherein:

X represents an appropriate amino protecting group, such as acetyl or benzyloxycarbonyl;

Y is any naturally or non-naturally occurring amino acid that forms a substrate capable of being recognized and cleaved by a PS133 polypeptide in the absence of an inhibitor;

n represents an integer which is any number, usually less than 20; and

Z represents any detectable tag such as a chromogenic or fluorogenic tag (e.g., para-nitroanilide or N-methyl coumarin), which, upon cleavage of the Y group from the above-described peptide substrate, undergoes a change in a signal characteristic (e.g., intensity, color, wavelength, or the like) which can thus be monitored as an indicator of the presence or absence of inhibitory activity.

An assay is established in which PS133 polypeptide-catalyzed cleavage of the peptide substrate is monitored in the presence or absence of a potential inhibitory compound or compound mixture. If the potential inhibitor does not inhibit the PS133 polypeptide proteolytic activity and the substrate (Y-group) is cleaved, the detectable tag Z undergoes a corresponding change in configuration. This configuration change allows a change in fluorescence to be detected by a fluorimeter in the case of a fluorogenic tag, or a change in color to be detected by a spectrophotometer in the case of a chromogenic tag. When the inhibitor successfully inhibits PS133 protease from cleaving the substrate, the Y group is not cleaved and Z does not have a change in configuration. Therefore, no fluorescence or color change is detectable, indicating that the compound has inhibited the action of the PS133 polypeptide. The assay described herein is also used to discover agonists/antagonists of proteolytic action of PS133. Because the PS133 polypeptide possesses an Asp residue at the base of the specificity pocket at position 165 (see FIG. 3), preferred amino acids at peptide substrate position Y1 are Arg and Lys, in analogy with structural features of Asp 189 of the related enzyme human trypsin and its corresponding peptide substrate Y1 residue preference (as discussed in C. Gaboriaud et al., *J. Mol. Bio.*, 259:995–1010 (1997), Academic Press, Ltd.).

The PS133 polynucleotides and the proteins encoded thereby which are provided and discussed hereinabove are useful as markers of prostate tissue disease, especially prostate cancer. Tests based upon the appearance of this marker in a test sample such as blood, plasma or serum can provide low cost, non-invasive, diagnostic information to aid the physician to make a diagnosis of cancer, to help select a therapy protocol, or to monitor the success of a chosen therapy. This marker may appear in readily accessible body fluids such as blood, urine or stool as antigens derived from the diseased tissue which are detectable by immunological methods. This marker may be elevated in a disease state, altered in a disease state, or be a normal protein of the prostate which appears in an inappropriate body compartment.

We claim:

1. A purified polynucleotide that comprises a polynucleotide thereof indicative of prostate disease selected from the group consisting of SEQUENCE ID NO 1, SEQUENCE ID NO 2, SEQUENCE ID NO 3, SEQUENCE ID NO 7, SEQUENCE ID NO 8, and complements thereof.

2. The purified polynucleotide of claim 1, wherein said polynucleotide is produced by recombinant techniques.

3. The purified polynucleotide of claim 1, wherein said polynucleotide is produced by synthetic techniques.

4. The purified polynucleotide of claim 1, wherein said polynucleotide comprises a sequence encoding at least one epitope.

5. The purified polynucleotide of claim 1, wherein said polynucleotide has the sequence presented as SEQUENCE ID NO 1, or complement thereof.

6. The purified polynucleotide of claim 1, wherein said polynucleotide has the sequence presented as SEQUENCE ID NO 2, or complement thereof.

7. The purified polynucleotide of claim 1, wherein said polynucleotide has the sequence presented as SEQUENCE ID NO 3, or complement thereof.

8. The purified polynucleotide of claim 1, wherein said polynucleotide has the sequence presented as SEQUENCE ID NO 7, or complement thereof.

9. The purified polynucleotide of claim 1, wherein said polynucleotide has the sequence presented as SEQUENCE ID NO 8, or complement thereof.

* * * * *

SEQUENCE LISTING (1) GENERAL INFORMATION:

(iii) NUMBER OF SEQUENCES: 76

(2) INFORMATION FOR SEQ ID NO:1:

(i) SEQUENCE CHARACTERISTICS:
      (A) LENGTH: 81 base pairs
      (B) TYPE: nucleic acid
      (C) STRANDEDNESS: single
      (D) TOPOLOGY: linear (xi) SEQUENCE DESCRIPTION: SEQ ID NO:1:

CTGCTGTAGC TGCCGCCACT GCCGTNTCCG NCGNCANTGG GNCCCCAGAG CCCCAGCCCC    60

AGAGCCTAGG AACCTGGGGC C    81

(2) INFORMATION FOR SEQ ID NO:2:

(i) SEQUENCE CHARACTERISTICS:
      (A) LENGTH: 222 base pairs
      (B) TYPE: nucleic acid
      (C) STRANDEDNESS: single
      (D) TOPOLOGY: linear (xi) SEQUENCE DESCRIPTION: SEQ ID NO:2:

GCTGCCGCCA CTGCCGTCTC CGCCGCCACT GGGCCCCCNG AGCCCCAGCN CCAGAGCCTA    60

GGAACCTGGG GCCCGCTCCT CCCCCCTCCA GGCCATGAGG ATTCTGCAGT TAATCCTGCT    120

TGCTCTGGCA ACAGGGCTTG TAGGGGGAGA GACCAGGATC ATCAAGGGGT TCGAGTGCNA    180

GCCTCACTCC CAGCCCTGGC AGGCAGCCCT GTTCGAGAAA AC    222

(2) INFORMATION FOR SEQ ID NO:3:

(i) SEQUENCE CHARACTERISTICS:
      (A) LENGTH: 239 base pairs
      (B) TYPE: nucleic acid
      (C) STRANDEDNESS: single
      (D) TOPOLOGY: linear (xi) SEQUENCE DESCRIPTION: SEQ ID NO:3:

CCCAGCCCTG GCAGGCAGCC CTGTTCAAGA AGACGCGGCT ACTCTGTGGG GCGACGCTCA    60

TCGCCCCCAG ATGGCTCCTG ACAGCAGCCC ACTGCCTCAA GCCCCGCTAC ATAGTTCACC    120

TGGGGCAGCA CAACCTCCAG AAGGAGGAGG GCTGTGAGCA GACCCGGACA GCCACTGAGT    180

CCTTCCCCCA CCCCGGCTTC AACAACAGCC TCCCCAACAA AGACCACCGC AATGACATC    239

(2) INFORMATION FOR SEQ ID NO:4:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (xi) SEQUENCE DESCRIPTION: SEQ ID NO:4:

```
GACCACCGCA ATGACATCAT GCTGGTGAAG ATGGCATCGC CAGTCTCCAT CACCTGGGCT    60

GTGCGACCCC TCACCCTCTC CTCACGCTGT GTCACTGCTG GCACCAGCTG CCTCATTTCC   120

GGCTGGGGCA GCACGTCCAG CCCCCAGTTA CGCCTGCCTC ACACCTTGCG ATGCGCCAAC   180

ATCACCATCA TTGAGCACCA GAAGTGTGAG AACGCCTACC CCGGCAACAT CACAGACACC   240

ATGGTGTGTG                                                          250
```

(2) INFORMATION FOR SEQ ID NO:5:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (xi) SEQUENCE DESCRIPTION: SEQ ID NO:5:

```
AACGCCTACC CCGGCAACAT CACAGACACC ATGGTGTGTG CCAGCGTGCA GGAAGGGGGC    60

AAGGACTCCT GCCAGGGTGA CTCCGGGGGC CCTCTGGTCT GTAACCAGTC TCTTCAAGGC   120

ATTATCTCCT GGGGCCAGGA TCCGTGTGCG ATCACCCGAA AGCCTGGTGT CTACACGAAA   180

GTCTGCAAAT ATGTGGACTG GATCCAGGAG ACGATGAAGA ACAATTAGAC TGGACCCACC   240

CACCACAGCC CATCACCCTC CA                                            262
```

(2) INFORMATION FOR SEQ ID NO:6:

(i) SEQUENCE CHARACTERISTICS:
        (A) LENGTH: 406 base pairs
        (B) TYPE: nucleic acid
        (C) STRANDEDNESS: single
        (D) TOPOLOGY: linear (xi) SEQUENCE DESCRIPTION: SEQ ID NO:6:

```
CATTTAGCAA ATATTTATTG AAACCTTGAT ATATGGCCAG GAGCTGTCTT TCGGGGCTGG    60

GGATACAACA GAGAACAAAC CAGGTGTTGT CATTCCCAGA GTCACAATAT TTCAAGGCAG   120

AATTTGAATC CAGGTCTCAC TNGATTTCGA ACCCCAGGTT CGATTATTAA GTGACAGCAT   180

CTCCTGTAGT CCAGGAGGCC CAAAGAATGT TCGCAGAGGG TCTTGGCTTA GGGTTTCTTA   240

TTAACAGAGT GAACAGGAAC CAAACACCAA GTGGAAATGG AGGGTGATGG GCTGTGGTGG   300

GTGGGTCCAG TCTAATTGTT CTTCATCGTC TCCTGGATCC AGTCCACATA TTTGCAGACT   360

TTCGTGTAGA CACCAGGCTT TCGGGTGATC GCACACGGAT CCTGGC                  406
```

(2) INFORMATION FOR SEQ ID NO:7:

(i) SEQUENCE CHARACTERISTICS:
        (A) LENGTH: 1166 base pairs
        (B) TYPE: nucleic acid
        (C) STRANDEDNESS: single
        (D) TOPOLOGY: linear (xi) SEQUENCE DESCRIPTION: SEQ ID NO:7:

```
CTGCTGTAGC TGCCGCCACT GCCGTCTCCG CCGCCACTGG GCCCCAGAG  CCCCAGCCCC      60

AGAGCCTAGG AACCTGGGGC CGCTCCTCC  CCCCTCCAGG CCATGAGGAT TCTGCAGTTA     120

ATCCTGCTTG CTCTGGCAAC AGGGCTTGTA GGGGAGAGA  CCAGGATCAT CAAGGGGTTC     180

GAGTGCNAGC CTCACTCCCA GCCCTGGCAG GCAGCCCTGT TCRAGAAARAC GCGGCTACTC    240

TGTGGGCGA  CGCTCATCGC CCCCAGATGG CTCCTGACAG CAGCCCACTG CCTCAAGCCC     300

CGCTACATAG TTCACCTGGG GCAGCACAAC CTCCAGAAGG AGGAGGGCTG TGAGCAGACC     360

CGGACAGCCA CTGAGTCCTT CCCCCACCCC GGCTTCAACA ACAGCCTCCC CAACAAAGAC     420

CACCGCAATG ACATCATGCT GGTGAAGATG GCATCGCCAG TCTCCATCAC CTGGGCTGTG     480

CGACCCCTCA CCCTCTCCTC ACGCTGTGTC ACTGCTGGCA CCAGCTGCCT CATTTCCGGC     540

TGGGGCAGCA CGTCCAGCCC CCAGTTACGC CTGCCTCACA CCTTGCGATG CGCCAACATC     600

ACCATCATTG AGCACCAGAA GTGTGAGAAC GCCTACCCCG GCAACATCAC AGACACCATG     660

GTGTGTGCCA GCGTGCAGGA AGGGGGCAAG GACTCCTGCC AGGGTGACTC CGGGGGCCCT     720

CTGGTCTGTA ACCAGTCTCT TCAAGGCATT ATCTCCTGGG GCCAGGATCC GTGTGCGATC     780

ACCCGAAAGC CTGGTGTCTA CACGAAAGTC TGCAAATATG TGGACTGGAT CCAGGAGACG     840

ATGAAGAACA ATTAGACTGG ACCCACCCAC CACAGCCCAT CACCCTCCAT TTCCACTTGG     900

TGTTTGGTTC CTGTTCACTC TGTTAATAAG AAACCCTAAG CCAAGACCCT CTGCAACAT     960

TCTTTGGGCC TCCTGGACTA CAGGAGATGC TGTCACTTAA TAATCGAACC TGGGGTTCGA   1020

AATCNAGTGA GACCTGGATT CAAATTCTGC CTTGAAATAT TGTGACTCTG GGAATGACAA   1080

CACCTGGTTT GTTCTCTGTT GTATCCCCAG CCCCGAAAGA CAGCTCCTGG CCATATATCA   1140

AGGTTTCAAT AAATATTTGC TAAATG                                       1166
```

(2) INFORMATION FOR SEQ ID NO:8:

(i) SEQUENCE CHARACTERISTICS:
        (A) LENGTH: 1192 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
GAATTCGAAT TCGCTGCCGC CACTGCCGTC TCCGCCGCCA CTGGGCCCCC AGAGCCCCAG     60

CCCCAGAGCC TAGGAACCTG GGCCCGCTC  CTCCCCCCTC CAGGCCATGA GGATTCTGCA    120

GTTAATCCTG CTTGCTCTGG CAACAGGGCT TGTAGGGGGA GAGACCAGGA TCATCAAGGG    180

GTTCGAGTGC AAGCCTCACT CCCAGCCCTG GCAGGCAGCC CTGTTCGAGA AGACGCGGCT    240

ACTCTGTGGG GCGACGCTCA TCGCCCCCAG ATGGCTCCTG ACAGCAGCCC ACTGCCTCAA    300

GCCCCGCTAC ATAGTTCACC TGGGGCAGCA CAACCTCCAG AAGGAGGAGG CTGTGAGCA    360

GACCCGGACA GCCACTGAGT CCTTCCCCCA CCCCGGCTTC AACAACAGCC TCCCCAACAA    420

AGACCACCGC AATGACATCA TGCTGGTGAA GATGGCATCG CCAGTCTCCA TCACCTGGGC    480

TGTGCGACCC CTCACCCTCT CCTCACGCTG TGTCACTGCT GGCACCAGCT GCCTCATTTC    540

CGGCTGGGGC AGCACGTCCA GCCCCCAGTT ACGCCTGCCT CACACCTTGC GATGCGCCAA    600

CATCACCATC ATTGAGCACC AGAAGTGTGA GAACGCCTAC CCCGGCAACA TCACAGACAC    660

CATGGTGTGT GCCAGCGTGC AGGAAGGGGG CAAGGACTCC TGCCAGGGTG ACTCCGGGGG    720
```

```
CCCTCTGGTC TGTAACCAGT CTCTTCAAGG CATTATCTCC TGGGGCCAGG ATCCGTGTGC      780

GATCACCCGA AAGCCTGGTG TCTACACGAA AGTCTGCAAA TATGTGGACT GGATCCAGGA      840

GACGATGAAG AACAATTAGA CTGGACCCAC CCACCACAGC CCATCACCCT CCATTTCCAC      900

TTGGTGTTTG GTTCCTGTTC ACTCTGTTAA TAAGAAACCC TAAGCCAAGA CCCTCTACGA      960

ACATTCTTTG GGCCTCCTGG ACTACAGGAG ATGCTGTCAC TTAATAATCA ACCTGGGGTT     1020

CGAAATCAGT GAGACCTGGA TTCAAATTCT GCCTTGAAAT ATTGTGACTC TGGGAATGAC     1080

AACACCTGGT TTGTTCTCTG TTGTATCCCC AGCCCCAAAG ACAGCTCCTG GCCATATATC     1140

AAGGTTTCAA TAAATATTTG CTAAATGAAA AAAAAAAAA AAGGGCGGCC GC              1192

(2) INFORMATION FOR SEQ ID NO:9:

(i) SEQUENCE CHARACTERISTICS:
         (A) LENGTH: 68 base pairs
         (B) TYPE: nucleic acid
         (C) STRANDEDNESS: single
         (D) TOPOLOGY: linear (xi) SEQUENCE DESCRIPTION: SEQ ID NO:9:

AGCTCGGAAT TCCGAGCTTG GATCCTCTAG AGCGGCCGCC GACTAGTGAG CTCGTCGACC       60

CGGGAATT                                                                68

(2) INFORMATION FOR SEQ ID NO:10:

(i) SEQUENCE CHARACTERISTICS:
         (A) LENGTH: 68 base pairs
         (B) TYPE: nucleic acid
         (C) STRANDEDNESS: single
         (D) TOPOLOGY: linear (xi) SEQUENCE DESCRIPTION: SEQ ID NO:10:

AATTAATTCC CGGGTCGACG AGCTCACTAG TCGGCGGCCG CTCTAGAGGA TCCAAGCTCG       60

GAATTCCG                                                                68

(2) INFORMATION FOR SEQ ID NO:11:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:11:

AGCGGATAAC AATTTCACAC AGGA                                              24

(2) INFORMATION FOR SEQ ID NO:12:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:12:

TGTAAAACGA CGGCCAGT                                                     18

(2) INFORMATION FOR SEQ ID NO:13:

(i) SEQUENCE CHARACTERISTICS:
         (A) LENGTH: 18 base pairs
         (B) TYPE: nucleic acid
```

(C) STRANDEDNESS: single
        (D) TOPOLOGY: linear (xi) SEQUENCE DESCRIPTION: SEQ ID NO:13:

TCAAGCCCCG CTACATAG                                                    18

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:14:

CACCAGAAGT GTGAGAACG                                                   19

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:15:

ACCCTCCATT TCCACTTG                                                    18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:16:

ATCAAGGGGT TCGAGTGC                                                    18

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:17:

CCTGGTGTCT ACACGAAAGT C                                                21

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

CCCAGGAGAT AATGCCTT                                                    18

(2) INFORMATION FOR SEQ ID NO:19:

(i) SEQUENCE CHARACTERISTICS:
        (A) LENGTH: 18 base pairs
        (B) TYPE: nucleic acid (C) STRANDEDNESS: single
        (D) TOPOLOGY: linear (xi) SEQUENCE DESCRIPTION: SEQ ID NO:19:

CCAGCATGAT GTCATTGC                                                     18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:20:

CTGTTGCCAG AGCAAGCA                                                     18

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:21:

AGTGACAGCA TCTCCTGTAG TC                                                22

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:22:

GGTAGGCGTT CTCACACTTC                                                   20

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

CAGGTGTTGT CATTCCCAGA G                                                 21

(2) INFORMATION FOR SEQ ID NO:24:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

Met Arg Ile Leu Gln Leu Ile Leu Leu Ala Leu Ala Thr Gly Leu Val
 1               5                  10                  15

Gly Gly Glu Thr Arg Ile Ile Lys Gly Phe Glu Cys Pro His Ser Gln
            20                  25                  30

```
Pro Trp Gln Ala Ala Leu Phe Lys Thr Arg Leu Leu Cys Gly Ala Thr
        35                  40                  45

Leu Ile Ala Pro Arg Trp Leu Leu Thr Ala Ala His Cys Leu Lys Pro
    50                  55                  60

Arg Tyr Ile Val His Leu Gly Gln His Asn Leu Gln Lys Glu Glu Gly
65                  70                  75                  80

Cys Glu Gln Thr Arg Thr Ala Thr Glu Ser Phe Pro His Pro Gly Phe
                85                  90                  95

Asn Asn Ser Leu Pro Asn Lys Asp His Arg Asn Asp Ile Met Leu Val
            100                 105                 110

Lys Met Ala Ser Pro Val Ser Ile Thr Trp Ala Val Arg Pro Leu Thr
            115                 120                 125

Leu Ser Ser Arg Cys Val Thr Ala Gly Thr Ser Cys Leu Ile Ser Gly
        130                 135                 140

Trp Gly Ser Thr Ser Ser Pro Gln Leu Arg Leu Pro His Thr Leu Arg
145                 150                 155                 160

Cys Ala Asn Ile Thr Ile Ile Glu His Gln Lys Cys Glu Asn Ala Tyr
                165                 170                 175

Pro Gly Asn Ile Thr Asp Thr Met Val Cys Ala Ser Val Gln Glu Gly
            180                 185                 190

Gly Lys Asp Ser Cys Gln Gly Asp Ser Gly Gly Pro Leu Val Cys Asn
            195                 200                 205

Gln Ser Leu Gln Gly Ile Ile Ser Trp Gly Gln Asp Pro Cys Ala Ile
        210                 215                 220

Thr Arg Lys Pro Gly Val Tyr Thr Lys Val Cys Lys Tyr Val Asp Trp
225                 230                 235                 240

Ile Gln Glu Thr Met Lys Asn Asn
                245

(2) INFORMATION FOR SEQ ID NO:25:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

Asn Leu Gln Lys Glu Glu Gly Cys Glu Gln Thr Arg Thr Ala Thr Glu
1               5                   10                  15

Ser Phe Pro His Pro Gly Phe Asn Asn Ser Leu Pro Asn Lys Asp His
            20                  25                  30

Arg Asn Asp
    35

(2) INFORMATION FOR SEQ ID NO:26:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

Glu His Gln Lys Cys Glu Asn Ala Tyr Pro Gly Asn Ile Thr Asp Thr
1               5                   10                  15
```

Met Val Cys Ala Ser Val Gln Glu Gly Lys Asp Ser Cys Gln Gly
            20                  25                  30

Asp Ser Gly Gly
            35

(2) INFORMATION FOR SEQ ID NO:27:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

Ser Trp Gly Gln Asp Pro Cys Ala Ile Thr Arg Lys Pro Gly Val Tyr
 1               5                  10                  15

Thr Lys Val Cys Lys Tyr Val Asp Trp Ile Gln Glu Thr Met Lys Asn
            20                  25                  30

Asn (2) INFORMATION FOR SEQ ID NO:28:

(i) SEQUENCE CHARACTERISTICS:
        (A) LENGTH: 251 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

Ile Ile Gly Gly Ser Asp Ala Asp Ile Lys Asn Phe Pro Trp Gln Val
 1               5                  10                  15

Phe Phe Asp Asn Pro Trp Ala Gly Ala Leu Ile Asn Glu Tyr Trp
            20                  25                  30

Val Leu Thr Ala Ala His Val Val Glu Gly Asn Arg Glu Pro Thr Met
            35                  40                  45

Tyr Val Gly Ser Thr Ser Val Gln Thr Ser Arg Leu Ala Lys Ser Lys
            50                  55                  60

Met Leu Thr Pro Glu His Val Phe Ile His Pro Gly Trp Lys Leu Leu
 65                  70                  75                  80

Glu Val Pro Glu Gly Arg Thr Asn Phe Asp Asn Asp Ile Ala Leu Val
                85                  90                  95

Arg Leu Lys Asp Pro Val Lys Met Gly Pro Thr Val Ser Pro Ile Cys
                100                 105                 110

Leu Pro Gly Thr Ser Ser Asp Tyr Asn Leu Met Asp Gly Asp Leu Gly
                115                 120                 125

Leu Ile Ser Gly Trp Gly Arg Thr Glu Lys Arg Asp Arg Ala Val Arg
            130                 135                 140

Leu Lys Ala Ala Arg Leu Pro Val Ala Pro Leu Arg Lys Cys Lys Glu
145                 150                 155                 160

Val Lys Val Glu Lys Pro Thr Ala Asp Ala Glu Ala Tyr Val Phe Thr
                165                 170                 175

Pro Asn Met Ile Cys Ala Gly Gly Glu Lys Gly Met Asp Ser Cys Lys
                180                 185                 190

Gly Asp Ser Gly Gly Ala Phe Ala Val Gln Asp Pro Asn Asp Lys Thr
            195                 200                 205

```
Lys Phe Tyr Ala Ala Gly Leu Val Ser Trp Gly Pro Gln Cys Gly Thr
    210                 215                 220

Tyr Gly Leu Tyr Thr Arg Val Lys Asn Tyr Val Asp Trp Ile Met Lys
225                 230                 235                 240

Thr Met Gln Glu Asn Ser Thr Pro Arg Glu Asp
                245                 250
```

(2) INFORMATION FOR SEQ ID NO:29:

(i) SEQUENCE CHARACTERISTICS:
        (A) LENGTH: 242 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

```
Ile Ile Gly Gly Gln Lys Ala Lys Met Gly Asn Phe Pro Trp Gln Val
1                   5                   10                  15

Phe Thr Asn Ile His Gly Arg Gly Gly Ala Leu Leu Gly Asp Arg
                20                  25                  30

Trp Ile Leu Thr Ala Ala His Thr Leu Tyr Pro Lys Glu His Glu Ala
                35                  40                  45

Gln Ser Asn Ala Ser Leu Asp Val Phe Leu Gly His Thr Asn Val Glu
    50                  55                  60

Glu Leu Met Lys Leu Gly Asn His Pro Ile Arg Arg Val Ser Val His
65                  70                  75                  80

Pro Asp Tyr Arg Gln Asp Glu Ser Tyr Asn Phe Glu Gly Asp Ile Ala
                85                  90                  95

Leu Leu Glu Leu Glu Asn Ser Val Thr Leu Gly Pro Asn Leu Leu Pro
                100                 105                 110

Ile Cys Leu Pro Asp Asn Asp Thr Phe Tyr Asp Leu Gly Leu Met Gly
                115                 120                 125

Tyr Val Ser Gly Phe Gly Val Met Glu Glu Lys Ile Ala His Asp Leu
    130                 135                 140

Arg Phe Val Arg Leu Pro Val Ala Asn Pro Gln Ala Cys Glu Asn Trp
145                 150                 155                 160

Leu Arg Gly Lys Asn Arg Met Asp Val Phe Ser Gln Asn Met Phe Cys
                165                 170                 175

Ala Gly His Pro Ser Leu Lys Gln Asp Ala Cys Gln Gly Asp Ser Gly
                180                 185                 190

Gly Val Phe Ala Val Arg Asp Pro Asn Thr Asp Arg Trp Val Ala Thr
                195                 200                 205

Gly Ile Val Ser Trp Gly Ile Gly Cys Ser Arg Gly Tyr Gly Phe Tyr
    210                 215                 220

Thr Lys Val Leu Asn Tyr Val Asp Trp Ile Lys Lys Glu Met Glu Glu
225                 230                 235                 240

Glu Asp
```

(2) INFORMATION FOR SEQ ID NO:30:

(i) SEQUENCE CHARACTERISTICS:
        (A) LENGTH: 229 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:30:

```
Ile Val Gly Gly His Glu Ala Gln Pro His Ser Arg Pro Tyr Met Ala
 1               5                  10                  15

Ser Leu Gln Met Arg Gly Asn Pro Gly Ser His Phe Cys Gly Gly Thr
            20                  25                  30

Leu Ile His Pro Ser Phe Val Leu Thr Ala Pro His Cys Leu Arg Asp
        35                  40                  45

Ile Pro Gln Arg Leu Val Asn Val Leu Gly Ala His Asn Val Arg
    50                  55                  60

Thr Gln Glu Pro Thr Gln Gln His Phe Ser Val Ala Gln Val Phe Leu
65                  70                  75                  80

Asn Asn Tyr Asp Ala Glu Asn Lys Leu Asn Asp Ile Leu Leu Ile Gln
                85                  90                  95

Leu Ser Ser Pro Ala Asn Leu Ser Ala Ser Val Thr Ser Val Gln Leu
               100                 105                 110

Pro Gln Gln Asp Gln Pro Val Pro His Gly Thr Gln Cys Leu Ala Met
            115                 120                 125

Gly Trp Gly Arg Val Gly Ala His Asp Pro Pro Ala Gln Val Leu Gln
        130                 135                 140

Glu Leu Asn Val Thr Val Val Thr Phe Phe Cys Arg Pro His Asn Ile
145                 150                 155                 160

Cys Thr Phe Val Pro Arg Arg Lys Ala Gly Ile Cys Phe Gly Asp Ser
                165                 170                 175

Gly Gly Pro Leu Ile Cys Asp Gly Ile Ile Gln Gly Ile Asp Ser Phe
            180                 185                 190

Val Ile Trp Gly Cys Ala Thr Arg Leu Phe Pro Asp Phe Phe Thr Arg
        195                 200                 205

Val Ala Leu Tyr Val Asp Trp Ile Arg Ser Thr Leu Arg Arg Val Glu
    210                 215                 220

Ala Lys Gly Arg Pro
225
```

(2) INFORMATION FOR SEQ ID NO:31:

(i) SEQUENCE CHARACTERISTICS:
        (A) LENGTH: 238 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

```
Ile Val Gly Gly Arg Arg Ala Arg Pro His Ala Trp Pro Phe Met Val
 1               5                  10                  15

Ser Leu Gln Leu Arg Gly Gly His Phe Cys Gly Ala Thr Leu Ile Ala
            20                  25                  30

Pro Asn Phe Val Met Ser Ala Ala His Cys Val Ala Asn Val Asn Val
        35                  40                  45

Arg Ala Val Arg Val Val Leu Gly Ala His Asn Leu Ser Arg Arg Glu
    50                  55                  60

Pro Thr Arg Gln Val Phe Ala Val Gln Arg Ile Phe Glu Asn Gly Tyr
65                  70                  75                  80

Asp Pro Val Asn Leu Leu Asn Asp Ile Val Ile Leu Gln Leu Asn Gly
                85                  90                  95
```

```
Ser Ala Thr Ile Asn Ala Asn Val Gln Val Ala Gln Leu Pro Ala Gln
                100                 105                 110

Gly Arg Arg Leu Gly Asn Gly Val Gln Cys Leu Ala Met Gly Trp Gly
            115                 120                 125

Leu Leu Gly Arg Asn Arg Gly Ile Ala Ser Val Leu Gln Glu Leu Asn
        130                 135                 140

Val Thr Val Val Thr Ser Leu Cys Arg Arg Ser Asn Val Cys Thr Leu
145                 150                 155                 160

Val Arg Gly Arg Gln Ala Gly Val Cys Phe Gly Asp Ser Gly Ser Pro
                165                 170                 175

Leu Val Cys Asn Gly Leu Ile His Gly Ile Ala Ser Phe Val Arg Gly
            180                 185                 190

Gly Cys Ala Ser Gly Leu Tyr Pro Asp Ala Phe Ala Pro Val Ala Gln
        195                 200                 205

Phe Val Asn Trp Ile Asp Ser Ile Ile Gln Arg Ser Glu Asp Asn Pro
    210                 215                 220

Cys Pro His Pro Arg Asp Pro Asp Pro Ala Ser Arg Thr His
225                 230                 235

(2) INFORMATION FOR SEQ ID NO:32:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Gly Ala Leu Ile His
                20                  25                  30

Ala Arg Phe Val Met Thr Ala Ala Ser Cys Phe Gln Ser Gln Asn Pro
            35                  40                  45

Gly Val Ser Thr Val Val Leu Gly Ala Tyr Asp Leu Arg Arg Arg Glu
        50                  55                  60

Arg Gln Ser Arg Gln Thr Phe Ser Ile Ser Ser Met Ser Glu Asn Gly
65                  70                  75                  80

Tyr Asp Pro Gln Gln Asn Leu Asn Asp Leu Met Leu Leu Gln Leu Asp
                85                  90                  95

Arg Glu Ala Asn Leu Thr Ser Ser Val Thr Ile Leu Pro Leu Pro Leu
                100                 105                 110

Gln Asn Ala Thr Val Glu Ala Gly Thr Arg Cys Gln Val Ala Gly Trp
            115                 120                 125

Gly Ser Gln Arg Ser Gly Gly Arg Leu Ser Arg Phe Pro Arg Phe Val
        130                 135                 140

Asn Val Thr Val Thr Pro Glu Asp Gln Cys Arg Pro Asn Asn Val Cys
145                 150                 155                 160

Thr Gly Val Leu Thr Arg Arg Gly Gly Ile Cys Asn Gly Asp Gly Gly
                165                 170                 175

Thr Pro Leu Val Cys Glu Gly Leu Ala His Gly Val Ala Ser Phe Ser
            180                 185                 190

Leu Gly Pro Cys Gly Arg Gly Pro Asp Phe Phe Thr Arg Val Ala Leu
        195                 200                 205
```

Phe Arg Asp Trp Ile Asp Gly Val Leu Asn Asn Pro Gly Pro Gly Pro
210                 215                 220

Ala
225

(2) INFORMATION FOR SEQ ID NO:33:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:33:

Ile Ile Asp Gly Ala Pro Cys Ala Arg Gly Ser His Pro Trp Gln Val
1               5                   10                  15

Ala Leu Leu Ser Gly Asn Gln Leu His Cys Gly Gly Val Leu Val Asn
                20                  25                  30

Glu Arg Trp Val Leu Thr Ala Ala His Cys Lys Met Asn Glu Tyr Thr
            35                  40                  45

Val His Leu Gly Ser Asp Thr Leu Gly Asp Arg Arg Ala Gln Arg Ile
50                  55                  60

Lys Ala Ser Lys Ser Phe Arg His Pro Gly Tyr Ser Thr Gln Thr His
65                  70                  75                  80

Val Asn Asp Leu Met Leu Val Lys Leu Asn Ser Gln Ala Arg Leu Ser
                85                  90                  95

Ser Met Val Lys Lys Val Arg Leu Pro Ser Arg Cys Glu Pro Pro Gly
                100                 105                 110

Thr Thr Cys Thr Val Ser Gly Trp Gly Thr Thr Thr Ser Pro Asp Val
            115                 120                 125

Thr Phe Pro Ser Asp Leu Met Cys Val Asp Val Lys Leu Ile Ser Pro
130                 135                 140

Gln Asp Cys Thr Lys Val Tyr Lys Asp Leu Leu Glu Asn Ser Met Leu
145                 150                 155                 160

Cys Ala Gly Ile Pro Asp Ser Lys Lys Asn Ala Cys Asn Gly Asp Ser
                165                 170                 175

Gly Gly Pro Leu Val Cys Arg Gly Thr Leu Gln Gly Leu Val Ser Trp
            180                 185                 190

Gly Thr Phe Pro Cys Gly Gln Pro Asn Asp Pro Gly Val Tyr Thr Gln
        195                 200                 205

Val Cys Lys Phe Thr Lys Trp Ile Asn Asp Thr Met Lys Lys His Arg
210                 215                 220

(2) INFORMATION FOR SEQ ID NO:34:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:34:

Ile Val Gly Gly Tyr Ile Cys Glu Glu Asn Ser Val Pro Tyr Gln Val
1               5                   10                  15

Ser Leu Asn Ser Gly Tyr His Phe Cys Gly Gly Ser Leu Ile Ser Glu
                20                  25                  30

```
Gln Trp Val Val Ser Ala Gly His Cys Tyr Lys Ser Arg Ile Gln Val
            35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Lys Tyr Asn Ser Arg Thr
65                  70                  75                  80

Leu Asp Asn Asp Ile Leu Leu Ile Lys Leu Ser Ser Pro Ala Val Ile
                85                  90                  95

Asn Ser Arg Val Ser Ala Ile Ser Leu Pro Thr Ala Pro Pro Ala Ala
            100                 105                 110

Gly Thr Glu Ser Leu Ile Ser Gly Trp Gly Asn Thr Leu Ser Ser Gly
            115                 120                 125

Ala Asp Tyr Pro Asp Glu Leu Gln Cys Leu Asp Ala Pro Val Leu Ser
    130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
            180                 185                 190

Trp Gly Tyr Gly Cys Ala Gln Lys Asn Arg Pro Gly Val Tyr Thr Lys
            195                 200                 205

Val Tyr Asn Tyr Val Asp Trp Ile Lys Asp Thr Ile Ala Ala Asn Ser
    210                 215                 220
```

(2) INFORMATION FOR SEQ ID NO:35:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

```
Ile Val Gly Gly Tyr Thr Cys Glu Glu Asn Ser Leu Pro Tyr Gln Val
1               5                   10                  15

Ser Leu Asn Ser Gly Ser His Phe Cys Gly Gly Ser Leu Ile Ser Glu
            20                  25                  30

Gln Trp Val Val Ser Ala Ala His Cys Tyr Lys Thr Arg Ile Gln Val
            35                  40                  45

Arg Leu Gly Glu His Asn Ile Lys Val Leu Glu Gly Asn Glu Gln Phe
    50                  55                  60

Ile Asn Ala Ala Lys Ile Ile Arg His Pro Lys Tyr Asn Arg Asp Thr
65                  70                  75                  80

Leu Asp Asn Asp Ile Met Leu Ile Lys Leu Ser Ser Pro Ala Val Ile
                85                  90                  95

Asn Ala Arg Val Ser Thr Ile Ser Leu Pro Thr Ala Pro Pro Ala Ala
            100                 105                 110

Gly Thr Glu Cys Leu Ile Ser Gly Trp Gly Asn Thr Leu Ser Phe Gly
            115                 120                 125

Ala Asp Tyr Pro Asp Glu Leu Lys Cys Leu Asp Ala Pro Val Leu Thr
    130                 135                 140

Gln Ala Glu Cys Lys Ala Ser Tyr Pro Gly Lys Ile Thr Asn Ser Met
145                 150                 155                 160
```

Phe Cys Val Gly Phe Leu Glu Gly Gly Lys Asp Ser Cys Gln Arg Asp
              165                 170                 175

Ser Gly Gly Pro Val Val Cys Asn Gly Gln Leu Gln Gly Val Val Ser
              180                 185                 190

Trp Gly His Gly Cys Ala Trp Lys Asn Arg Pro Gly Val Tyr Thr Lys
              195                 200                 205

Val Tyr Asn Tyr Val Asp Trp Ile Lys Asp Thr Ile Ala Ala Asn Ser
    210                 215                 220

(2) INFORMATION FOR SEQ ID NO:36:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

Ile Val Gly Gly Tyr Asn Cys Glu Glu Asn Ser Val Pro Tyr Gln Val
 1               5                  10                  15

Ser Leu Asn Ser Gly Tyr His Phe Cys Gly Gly Ser Leu Ile Asn Glu
              20                  25                  30

Gln Trp Val Val Ser Ala Gly His Cys Tyr Lys Ser Arg Ile Gln Val
              35                  40                  45

Arg Leu Gly Glu His Asn Ile Glu Val Leu Glu Gly Asn Glu Gln Phe
       50                  55                  60

Ile Asn Ala Ala Lys Ile Ile Arg His Pro Gln Tyr Asp Arg Lys Thr
65                   70                  75                  80

Leu Asn Asn Asp Ile Met Leu Ile Lys Leu Ser Ser Arg Ala Val Ile
              85                  90                  95

Asn Ala Arg Val Ser Thr Ile Ser Leu Pro Thr Ala Pro Pro Ala Thr
             100                 105                 110

Gly Thr Lys Cys Leu Ile Ser Gly Trp Gly Asn Thr Ala Ser Ser Gly
             115                 120                 125

Ala Asp Tyr Pro Asp Glu Leu Gln Cys Leu Asp Ala Pro Val Leu Ser
             130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
              165                 170                 175

Ser Gly Gly Pro Val Val Cys Asn Gly Gln Leu Gln Gly Val Val Ser
              180                 185                 190

Trp Gly Asp Gly Cys Ala Gln Lys Asn Lys Pro Gly Val Tyr Thr Lys
              195                 200                 205

Val Tyr Asn Tyr Val Lys Trp Ile Lys Asn Thr Ile Ala Ala Asn Ser
    210                 215                 220

(2) INFORMATION FOR SEQ ID NO:37:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:37:

```
Ile Val Gly Gly Trp Glu Cys Glu Lys His Ser Gln Pro Trp Gln Val
  1               5                  10                  15

Ala Val Tyr Ser His Gly Trp Ala His Cys Gly Gly Val Leu Val His
             20                  25                  30

Pro Gln Trp Val Leu Thr Ala Ala His Cys Leu Lys Lys Asn Ser Gln
             35                  40                  45

Val Trp Leu Gly Arg His Asn Leu Phe Glu Pro Glu Asp Thr Gly Gln
 50                  55                  60

Arg Val Pro Val Ser His Ser Phe Pro His Pro Leu Tyr Asn Met Ser
 65                  70                  75                  80

Leu Leu Lys His Gln Ser Leu Arg Pro Asp Glu Asp Ser Ser His Asp
             85                  90                  95

Leu Met Leu Leu Arg Leu Ser Glu Pro Ala Lys Ile Thr Asp Val Val
            100                 105                 110

Lys Val Leu Gly Leu Pro Thr Gln Glu Pro Ala Leu Gly Thr Thr Cys
            115                 120                 125

Tyr Ala Ser Gly Trp Gly Ser Ile Glu Pro Glu Glu Phe Leu Arg Pro
130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
            165                 170                 175

Leu Trp Thr Gly Gly Lys Asp Thr Cys Gly Gly Asp Ser Gly Gly Pro
            180                 185                 190

Leu Val Cys Asn Gly Val Leu Gln Gly Ile Thr Ser Trp Gly Pro Glu
            195                 200                 205

Pro Cys Ala Leu Pro Glu Lys Pro Ala Val Tyr Thr Lys Val Val His
            210                 215                 220

Tyr Arg Lys Trp Ile Lys Asp Thr Ile Ala Ala Asn Pro
225                 230                 235
```

(2) INFORMATION FOR SEQ ID NO:38:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:38:

```
Ile Val Gly Gly Trp Glu Cys Glu Lys His Ser Gln Pro Trp Gln Val
  1               5                  10                  15

Leu Val Ala Ser Arg Gly Arg Ala Val Cys Gly Gly Val Leu Val His
             20                  25                  30

Pro Gln Trp Val Leu Thr Ala Ala His Cys Ile Arg Asn Lys Ser Val
             35                  40                  45

Ile Leu Leu Gly Arg His Ser Leu Phe His Pro Glu Asp Thr Gly Gln
 50                  55                  60

Val Phe Gln Val Ser His Ser Phe Pro His Pro Leu Tyr Asp Met Ser
 65                  70                  75                  80

Leu Leu Lys Asn Arg Phe Leu Arg Pro Gly Asp Asp Ser Ser His Asp
             85                  90                  95
```

```
Leu Met Leu Leu Arg Leu Ser Glu Pro Ala Glu Leu Thr Asp Ala Val
            100                 105                 110
Lys Val Met Asp Leu Pro Thr Gln Glu Pro Ala Leu Gly Thr Thr Cys
            115                 120                 125
Tyr Ala Ser Gly Trp Gly Ser Ile Glu Pro Glu Glu Phe Leu Thr Pro
            130                 135                 140
Lys Lys Leu Gln Cys Val Asp Leu His Val Ile Ser Asn Asp Val Cys
145                 150                 155                 160
Ala Gln Val His Pro Gln Lys Val Thr Lys Phe Met Leu Cys Ala Gly
                165                 170                 175
Arg Trp Thr Gly Gly Lys Ser Thr Cys Ser Gly Asp Ser Gly Gly Pro
            180                 185                 190
Leu Val Cys Asn Gly Val Leu Gln Gly Ile Thr Ser Trp Gly Ser Glu
            195                 200                 205
Pro Cys Ala Leu Pro Glu Arg Pro Ser Leu Tyr Thr Lys Val Val His
            210                 215                 220
Tyr Arg Lys Trp Ile Lys Asp Thr Ile Val Ala Asn Pro
225                 230                 235

(2) INFORMATION FOR SEQ ID NO:39:

(i) SEQUENCE CHARACTERISTICS:
        (A) LENGTH: 238 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:39:

Ile Val Gly Gly Trp Glu Cys Glu Gln His Ser Gln Pro Trp Gln Ala
1               5                   10                  15
Ala Leu Tyr His Phe Ser Thr Phe Gln Cys Gly Gly Ile Leu Val His
                20                  25                  30
Arg Gln Trp Val Leu Thr Ala Ala His Cys Ile Ser Asp Asn Tyr Gln
            35                  40                  45
Leu Trp Leu Gly Arg His Asn Leu Phe Asp Asp Glu Asn Thr Ala Gln
50                  55                  60
Phe Val His Val Ser Glu Ser Phe Pro His Pro Gly Phe Asn Met Ser
65                  70                  75                  80
Leu Leu Glu Asn His Thr Arg Gln Ala Asp Glu Asp Tyr Ser His Asp
                85                  90                  95
Leu Met Leu Leu Arg Leu Thr Gly Pro Ala Asp Thr Ile Thr Asp Ala
            100                 105                 110
Val Lys Val Val Glu Leu Pro Thr Gln Glu Pro Glu Val Gly Ser Thr
            115                 120                 125
Cys Leu Ala Ser Gly Trp Gly Ser Ile Glu Pro Glu Asn Phe Ser Phe
            130                 135                 140
Pro Asp Asp Leu Gln Cys Val Asp Leu Lys Ile Leu Pro Asn Asp Glu
145                 150                 155                 160
Cys Glu Lys Ala His Val Gln Lys Val Thr Asp Phe Met Leu Cys Val
                165                 170                 175
Gly His Leu Glu Gly Gly Lys Asp Thr Cys Val Gly Asp Ser Gly Gly
            180                 185                 190
Pro Leu Met Cys Asp Gly Val Leu Gln Gly Val Thr Ser Trp Gly Tyr
            195                 200                 205
```

```
Val Pro Cys Gly Thr Pro Asn Lys Pro Ser Val Ala Val Arg Val Leu
    210                 215                 220

Ser Tyr Val Lys Trp Ile Glu Asp Thr Ile Ala Glu Asn Ser
225                 230                 235
```

(2) INFORMATION FOR SEQ ID NO:40:

(i) SEQUENCE CHARACTERISTICS:
        (A) LENGTH: 227 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:40:

```
Ile Ile Gly Gly His Glu Ala Lys Pro His Ser Arg Pro Tyr Met Ala
1                   5                   10                  15

Tyr Leu Met Ile Trp Asp Gln Lys Ser Leu Lys Arg Cys Gly Gly Phe
                20                  25                  30

Leu Ile Gln Asp Asp Phe Val Leu Thr Ala Ala His Cys Trp Gly Ser
                35                  40                  45

Ser Ile Asn Val Thr Leu Gly Ala His Asn Ile Lys Glu Gln Glu Pro
50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
                100                 105                 110

Lys Ala Gln Val Lys Pro Gly Gln Thr Cys Ser Val Ala Gly Trp Gly
                115                 120                 125

Gln Thr Ala Pro Leu Gly Lys His Ser His Thr Leu Gln Glu Val Lys
                130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
                180                 185                 190

Ala Gln Gly Ile Val Ser Tyr Gly Arg Asn Asn Gly Met Pro Pro Arg
                195                 200                 205

Ala Cys Thr Lys Val Ser Ser Phe Val His Trp Ile Lys Lys Thr Met
    210                 215                 220

Lys Arg Tyr
225
```

(2) INFORMATION FOR SEQ ID NO:41:

(i) SEQUENCE CHARACTERISTICS:
        (A) LENGTH: 226 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:41:

```
Ile Ile Gly Gly His Glu Ala Lys Pro His Ser Arg Pro Tyr Met Ala
1                   5                   10                  15
```

-continued

```
Phe Val Gln Phe Leu Gln Glu Lys Ser Arg Lys Arg Cys Gly Gly Ile
             20                  25                  30

Leu Val Arg Lys Asp Phe Val Leu Thr Ala Ala His Cys Gln Gly Ser
             35                  40                  45

Ser Ile Asn Val Thr Leu Gly Ala His Asn Ile Lys Glu Gln Glu Arg
 50                  55                  60

Thr Gln Gln Phe Ile Pro Val Lys Arg Pro Ile Pro His Pro Ala Tyr
 65                  70                  75                  80

Asn Pro Lys Asn Phe Ser Asn Asp Ile Met Leu Leu Gln Leu Glu Arg
             85                  90                  95

Lys Ala Lys Trp Thr Thr Ala Val Arg Pro Leu Arg Leu Pro Ser Ser
            100                 105                 110

Lys Ala Gln Val Lys Pro Gly Gln Leu Cys Ser Val Ala Gly Trp Gly
            115                 120                 125

Tyr Val Ser Met Ser Thr Leu Ala Thr Thr Leu Gln Glu Val Leu Leu
            130                 135                 140

Thr Val Gln Lys Asp Cys Gln Cys Glu Arg Leu Phe His Gly Asn Tyr
145                 150                 155                 160

Ser Arg Ala Thr Glu Ile Cys Val Gly Asp Pro Lys Lys Thr Gln Thr
                165                 170                 175

Gly Phe Lys Gly Asp Ser Gly Gly Pro Leu Val Cys Lys Asp Val Ala
            180                 185                 190

Gln Gly Ile Leu Ser Tyr Gly Asn Lys Lys Gly Thr Pro Pro Gly Val
            195                 200                 205

Tyr Ile Lys Val Ser His Phe Leu Pro Trp Ile Lys Arg Thr Met Lys
210                 215                 220

Arg Leu
225
```

(2) INFORMATION FOR SEQ ID NO:42:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:42:

```
Ile Ile Gly Gly Arg Glu Ser Arg Pro His Ser Arg Pro Tyr Met Ala
 1                   5                  10                  15

Tyr Leu Gln Ile Gln Ser Pro Ala Gly Gln Ser Arg Cys Gly Gly Phe
             20                  25                  30

Leu Val Arg Glu Asp Phe Val Leu Thr Ala Ala His Cys Trp Gly Ser
             35                  40                  45

Asn Ile Asn Val Thr Leu Gly Ala His Asn Ile Gln Arg Arg Glu Asn
 50                  55                  60

Thr Gln Gln His Ile Thr Ala Arg Arg Ala Ile Arg His Pro Gln Tyr
 65                  70                  75                  80

Asn Gln Arg Thr Ile Gln Asn Asp Ile Met Leu Leu Gln Leu Ser Arg
             85                  90                  95

Arg Val Arg Arg Asn Arg Asn Val Asn Pro Val Ala Leu Pro Arg Ala
            100                 105                 110

Gln Glu Gly Leu Arg Pro Gly Thr Leu Cys Thr Val Ala Gly Trp Gly
            115                 120                 125
```

```
Arg Val Ser Met Arg Arg Gly Thr Asp Thr Leu Arg Glu Val Gln Leu
    130                 135                 140
Arg Val Gln Arg Asp Arg Gln Cys Leu Arg Ile Phe Gly Ser Tyr Asp
145                 150                 155                 160
Pro Arg Arg Gln Ile Cys Val Gly Asp Arg Arg Glu Arg Lys Ala Ala
                    165                 170                 175
Phe Lys Gly Asp Ser Gly Gly Pro Leu Leu Cys Asn Asn Val Ala His
                180                 185                 190
Gly Ile Val Ser Tyr Gly Lys Ser Ser Gly Val Pro Pro Glu Val Phe
                195                 200                 205
Thr Arg Val Ser Ser Phe Leu Pro Trp Ile Arg Thr Thr Met Arg Ser
    210                 215                 220
Phe Lys Leu Leu Asp Gln Met Glu Thr Pro Leu
225                 230                 235
```

(2) INFORMATION FOR SEQ ID NO:43:

(i) SEQUENCE CHARACTERISTICS:
        (A) LENGTH: 226 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:43:

```
Ile Ile Gly Gly Thr Glu Cys Lys Pro His Ser Arg Pro Tyr Met Ala
1                   5                   10                  15
Tyr Leu Glu Ile Val Thr Ser Asn Gly Pro Ser Lys Phe Cys Gly Gly
                20                  25                  30
Phe Leu Ile Arg Arg Asn Phe Val Leu Thr Ala Ala His Cys Ala Gly
                35                  40                  45
Arg Ser Ile Thr Val Thr Leu Gly Ala His Asn Ile Thr Glu Glu Glu
    50                  55                  60
Asp Thr Trp Gln Lys Leu Glu Val Ile Lys Gln Phe Arg His Pro Lys
65                  70                  75                  80
Tyr Asn Thr Ser Thr Leu His His Asp Ile Met Leu Leu Lys Leu Lys
                85                  90                  95
Glu Lys Ala Ser Leu Thr Leu Ala Val Gly Thr Leu Pro Phe Pro Ser
                100                 105                 110
Gln Phe Asn Phe Val Pro Pro Gly Arg Met Cys Arg Val Ala Gly Trp
                115                 120                 125
Gly Arg Thr Gly Val Leu Lys Pro Gly Ser Asp Thr Leu Gln Glu Val
    130                 135                 140
Lys Leu Arg Leu Met Asp Pro Gln Ala Cys Ser His Phe Arg Asp Phe
145                 150                 155                 160
Asp His Asn Leu Gln Leu Cys Val Gly Asn Pro Arg Lys Thr Lys Ser
                165                 170                 175
Ala Phe Lys Gly Asp Ser Gly Gly Pro Leu Leu Cys Ala Gly Val Ala
                180                 185                 190
Gln Gly Ile Val Ser Tyr Gly Arg Ser Asp Ala Lys Pro Pro Ala Val
                195                 200                 205
Phe Thr Arg Ile Ser His Tyr Arg Pro Trp Ile Asn Gln Ile Leu Gln
    210                 215                 220
Ala Asn
225
```

(2) INFORMATION FOR SEQ ID NO:44:

(i) SEQUENCE CHARACTERISTICS:
        (A) LENGTH: 228 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:44:

```
Met Leu Gly Gly Arg Glu Ala Glu Ala His Ala Arg Pro Tyr Met Ala
  1               5                  10                  15

Ser Val Gln Leu Asn Gly Ala His Leu Cys Ala Gly Val Leu Val Ala
             20                  25                  30

Glu Arg Trp Val Leu Ser Ala Ala His Cys Leu Glu Asp Ala Ala Asp
         35                  40                  45

Gly Lys Val Gln Val Leu Leu Gly Ala His Ser Leu Ser Gln Pro Glu
 50                  55                  60

Pro Ser Lys Arg Leu Tyr Asp Val Leu Arg Ala Val Pro His Pro Asp
 65                  70                  75                  80

Ser Gln Pro Asp Thr Ile Asp His Asp Leu Leu Leu Gln Leu Ser
             85                  90                  95

Glu Lys Ala Thr Leu Gly Pro Ala Val Arg Pro Leu Pro Trp Gln Arg
            100                 105                 110

Val Asp Arg Asp Val Ala Pro Gly Thr Leu Cys Asp Val Ala Gly Trp
            115                 120                 125

Gly Ile Val Asn His Ala Gly Arg Arg Pro Asp Ser Leu Gln His Val
130                 135                 140

Leu Leu Pro Val Leu Asp Arg Ala Thr Cys Asn Arg Arg Thr His His
145                 150                 155                 160

Asp Gly Ala Ile Thr Glu Arg Leu Met Cys Ala Glu Ser Asn Arg Arg
                165                 170                 175

Asp Ser Cys Lys Gly Asp Ser Gly Gly Pro Leu Val Cys Gly Gly Val
            180                 185                 190

Leu Glu Gly Val Val Thr Ser Gly Ser Arg Val Cys Gly Asn Arg Lys
            195                 200                 205

Lys Pro Gly Ile Tyr Thr Arg Val Ala Ser Tyr Ala Ala Trp Ile Asp
            210                 215                 220

Ser Val Leu Ala
225
```

(2) INFORMATION FOR SEQ ID NO:45:

(i) SEQUENCE CHARACTERISTICS:
        (A) LENGTH: 232 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:45:

```
Ile Ile Gly Gly Arg Glu Val Ile Pro His Ser Arg Pro Tyr Met Ala
  1               5                  10                  15

Ser Leu Gln Arg Asn Gly Ser His Leu Cys Gly Gly Val Leu Val His
             20                  25                  30

Pro Lys Trp Val Leu Thr Ala Ala His Cys Leu Ala Gln Arg Met Ala
         35                  40                  45
```

```
Gln Leu Arg Leu Val Leu Gly Leu His Thr Leu Asp Ser Pro Gly Leu
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
            115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
            180                 185                 190

Val Leu Ala Gly Val Leu Ser Phe Ser Ser Arg Val Cys Thr Asp Ile
            195                 200                 205

Phe Lys Pro Pro Val Ala Thr Ala Val Ala Pro Tyr Val Ser Trp Ile
    210                 215                 220

Arg Lys Val Thr Gly Arg Ser Ala
225                 230

(2) INFORMATION FOR SEQ ID NO:46:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:46:

Ile Ile Gly Gly Asn Glu Val Thr Pro His Ser Arg Pro Tyr Met Val
1               5                   10                  15

Leu Leu Ser Leu Asp Arg Lys Thr Ile Cys Ala Gly Ala Leu Ile Ala
                20                  25                  30

Lys Asp Trp Val Leu Thr Ala Ala His Cys Asn Leu Asn Lys Arg Ser
            35                  40                  45

Gln Val Ile Leu Gly Ala His Ser Ile Thr Arg Glu Glu Pro Thr Lys
    50                  55                  60

Gln Ile Met Leu Val Lys Lys Glu Phe Pro Tyr Pro Cys Tyr Asp Pro
65                  70                  75                  80

Ala Thr Arg Glu Gly Asp Leu Lys Leu Leu Gln Leu Thr Glu Lys Ala
                85                  90                  95

Lys Ile Asn Lys Tyr Val Thr Ile Leu His Leu Pro Lys Lys Gly Asp
            100                 105                 110

Asp Val Lys Pro Gly Thr Met Cys Gln Val Ala Gly Trp Gly Arg Thr
            115                 120                 125

His Asn Ser Ala Ser Trp Ser Asp Thr Leu Arg Glu Val Asn Ile Thr
    130                 135                 140

Ile Ile Asp Arg Lys Val Cys Asn Asp Arg Asn His Tyr Asn Phe Asn
145                 150                 155                 160
```

```
Pro Val Ile Gly Met Asn Met Val Cys Ala Gly Ser Leu Arg Gly Gly
                165                 170                 175

Arg Asp Ser Cys Asn Gly Asp Ser Gly Ser Pro Leu Leu Cys Glu Gly
            180                 185                 190

Val Phe Arg Gly Val Thr Ser Phe Gly Leu Glu Asn Lys Cys Gly Asp
        195                 200                 205

Pro Arg Gly Pro Gly Val Tyr Ile Leu Leu Ser Lys Lys His Leu Asn
    210                 215                 220

Trp Ile Ile Met Thr Ile Lys Gly Ala Val
225                 230

(2) INFORMATION FOR SEQ ID NO:47:

(i) SEQUENCE CHARACTERISTICS:
        (A) LENGTH: 251 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:47:

Ile Phe Asn Gly Arg Pro Ala Gln Lys Gly Thr Thr Pro Trp Ile Ala
1               5                   10                  15

Met Leu Ser His Leu Asn Gly Gln Pro Phe Cys Gly Gly Ser Leu Leu
            20                  25                  30

Gly Ser Ser Trp Ile Val Thr Ala Ala His Cys Leu His Gln Ser Leu
        35                  40                  45

Asp Pro Lys Asp Pro Thr Leu Arg Asp Ser Asp Leu Leu Ser Pro Ser
    50                  55                  60

Asp Phe Lys Ile Ile Leu Gly Lys His Trp Arg Leu Arg Ser Asp Glu
65                  70                  75                  80

Asn Glu Gln His Leu Gly Val Lys His Thr Thr Leu His Pro Lys Tyr
                85                  90                  95

Asp Pro Asn Thr Phe Glu Asn Asp Val Ala Leu Val Glu Leu Leu Glu
            100                 105                 110

Ser Pro Val Leu Asn Ala Phe Val Met Pro Ile Cys Leu Pro Glu Gly
        115                 120                 125

Pro Gln Gln Glu Gly Ala Met Val Ile Val Ser Gly Trp Gly Lys Gln
    130                 135                 140

Phe Leu Gln Arg Phe Pro Glu Thr Leu Met Glu Ile Glu Ile Pro Ile
145                 150                 155                 160

Val Asp His Ser Thr Cys Gln Lys Ala Tyr Ala Pro Leu Lys Lys Lys
                165                 170                 175

Val Thr Arg Asp Met Ile Cys Ala Gly Glu Lys Glu Gly Gly Lys Asp
            180                 185                 190

Ala Cys Ser Gly Asp Ser Gly Gly Pro Met Val Thr Leu Asn Arg Glu
        195                 200                 205

Arg Gly Gln Trp Tyr Leu Val Gly Thr Val Ser Trp Gly Asp Asp Cys
    210                 215                 220

Gly Lys Lys Asp Arg Tyr Gly Val Tyr Ser Tyr Ile His His Asn Lys
225                 230                 235                 240

Asp Trp Ile Gln Arg Val Thr Gly Val Arg Asn
                245                 250
```

(2) INFORMATION FOR SEQ ID NO:48:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:48:

```
Val Val Gly Gly Glu Asp Ala Lys Pro Gly Gln Phe Pro Trp Gln Val
 1               5                  10                  15
Val Leu Asn Gly Lys Val Asp Ala Phe Cys Gly Gly Ser Ile Val Asn
                20                  25                  30
Glu Lys Trp Ile Val Thr Ala Ala His Cys Val Glu Thr Gly Val Lys
            35                  40                  45
Ile Thr Val Val Ala Gly Glu His Asn Ile Glu Glu Thr Glu His Thr
        50                  55                  60
Glu Gln Lys Arg Asn Val Ile Arg Ile Ile Pro His His Asn Tyr Asn
65                  70                  75                  80
Ala Ala Ile Asn Lys Tyr Asn His Asp Ile Ala Leu Leu Glu Leu Asp
                85                  90                  95
Glu Pro Leu Val Leu Asn Ser Tyr Val Thr Pro Ile Cys Ile Ala Asp
            100                 105                 110
Lys Glu Tyr Thr Asn Ile Phe Leu Lys Phe Gly Ser Gly Tyr Val Ser
        115                 120                 125
Gly Trp Gly Arg Val Phe His Lys Gly Arg Ser Ala Leu Val Leu Gln
    130                 135                 140
Tyr Leu Arg Val Pro Leu Val Asp Arg Ala Thr Cys Leu Arg Ser Thr
145                 150                 155                 160
Lys Phe Thr Ile Tyr Asn Asn Met Phe Cys Ala Gly Phe His Glu Gly
                165                 170                 175
Gly Arg Asp Ser Cys Gln Gly Asp Ser Gly Gly Pro His Val Thr Glu
            180                 185                 190
Val Glu Gly Thr Ser Phe Leu Thr Gly Ile Ile Ser Trp Gly Glu Glu
        195                 200                 205
Cys Ala Met Lys Gly Lys Tyr Gly Ile Tyr Thr Lys Val Ser Arg Tyr
    210                 215                 220
Val Asn Trp Ile Lys Glu Lys Thr Lys Leu Thr
225                 230                 235
```

(2) INFORMATION FOR SEQ ID NO:49:

(i) SEQUENCE CHARACTERISTICS:
        (A) LENGTH: 247 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:49:

```
Ile Val Gly Gly Gln Glu Cys Lys Asp Gly Glu Cys Pro Trp Gln Ala
 1               5                  10                  15
Leu Leu Ile Asn Glu Glu Asn Glu Gly Phe Cys Gly Gly Thr Ile Leu
                20                  25                  30
Ser Glu Phe Tyr Ile Leu Thr Ala Ala His Cys Leu Tyr Gln Ala Lys
            35                  40                  45
```

```
Arg Phe Glu Gly Asp Arg Asn Thr Glu Gln Glu Gly Gly Glu Ala
 50                  55                  60
Val His Glu Val Glu Val Ile Lys His Asn Arg Phe Thr Lys Glu
 65                  70                  75                  80
Thr Tyr Asp Phe Asp Ile Ala Val Leu Arg Leu Lys Thr Pro Ile Thr
                 85                  90                  95
Phe Arg Met Asn Val Ala Pro Ala Cys Leu Pro Glu Arg Asp Trp Ala
            100                 105                 110
Glu Ser Thr Leu Met Thr Gln Lys Thr Gly Ile Val Ser Gly Phe Gly
            115                 120                 125
Arg Thr His Glu Lys Gly Arg Gln Ser Thr Arg Leu Lys Met Leu Glu
            130                 135                 140
Val Pro Tyr Val Asp Arg Asn Ser Cys Lys Leu Ser Ser Ser Phe Ile
145                 150                 155                 160
Ile Thr Gln Asn Met Phe Cys Ala Gly Tyr Asp Thr Lys Gln Glu Asp
                165                 170                 175
Ala Cys Gln Gly Asp Ser Gly Gly Pro His Val Thr Arg Phe Lys Asp
            180                 185                 190
Thr Tyr Phe Val Thr Gly Ile Val Ser Trp Gly Glu Gly Cys Ala Arg
            195                 200                 205
Lys Gly Lys Tyr Gly Ile Tyr Thr Lys Val Thr Ala Phe Leu Lys Trp
210                 215                 220
Ile Asp Arg Ser Met Lys Thr Arg Gly Leu Pro Lys Ala Lys Ser His
225                 230                 235                 240
Ala Pro Glu Val Ile Thr Ser
                245

(2) INFORMATION FOR SEQ ID NO:50:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:50:

Ile Val Gly Gly Lys Val Cys Pro Lys Gly Glu Cys Pro Trp Gln Val
  1               5                  10                  15
Leu Leu Leu Val Asn Gly Ala Gln Leu Cys Gly Gly Thr Leu Ile Asn
                 20                  25                  30
Thr Ile Trp Val Val Ser Ala Ala His Cys Phe Asp Lys Ile Lys Asn
             35                  40                  45
Trp Arg Asn Leu Ile Ala Val Leu Gly Glu His Asp Leu Ser Glu His
 50                  55                  60
Asp Gly Asp Glu Gln Ser Arg Arg Val Ala Gln Val Ile Ile Pro Ser
 65                  70                  75                  80
Thr Tyr Val Pro Gly Thr Thr Asn His Asp Ile Ala Leu Leu Arg Leu
                 85                  90                  95
His Gln Pro Val Val Leu Thr Asp His Val Val Pro Leu Cys Leu Pro
            100                 105                 110
Glu Arg Thr Phe Ser Glu Arg Thr Leu Ala Phe Val Arg Phe Ser Leu
            115                 120                 125
Val Ser Gly Trp Gly Gln Leu Leu Asp Arg Gly Ala Thr Ala Leu Glu
            130                 135                 140
```

```
Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
                180                 185                 190

Gly Gly Pro His Ala Thr His Tyr Arg Gly Thr Trp Tyr Leu Thr Gly
                195                 200                 205

Ile Val Ser Trp Gly Gln Gly Cys Ala Thr Val Gly His Phe Gly Val
                210                 215                 220

Tyr Thr Arg Val Ser Gln Tyr Ile Glu Trp Leu Gln Lys Leu Met Arg
225                 230                 235                 240

Ser Glu Pro Arg Pro Gly Val Leu Leu Arg Ala Pro Phe Pro
                245                 250

(2) INFORMATION FOR SEQ ID NO:51:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:51:

Leu Ile Asp Gly Lys Met Thr Arg Arg Gly Asp Ser Pro Trp Gln Val
1               5                   10                  15

Val Leu Leu Asp Ser Lys Lys Leu Ala Cys Gly Ala Val Leu Ile
                20                  25                  30

His Pro Ser Trp Val Leu Thr Ala Ala His Cys Met Asp Glu Ser Lys
                35                  40                  45

Lys Leu Leu Val Arg Leu Gly Glu Tyr Asp Leu Arg Arg Trp Glu Lys
                50                  55                  60

Trp Glu Leu Asp Leu Asp Ile Lys Glu Val Phe Val His Pro Asn Tyr
65                  70                  75                  80

Ser Lys Ser Thr Thr Asp Asn Asp Ile Ala Leu Leu His Leu Ala Gln
                85                  90                  95

Pro Ala Thr Leu Ser Gln Thr Ile Val Pro Ile Cys Leu Pro Asp Ser
                100                 105                 110

Gly Leu Ala Glu Arg Glu Leu Asn Gln Ala Gly Gln Glu Thr Leu Val
                115                 120                 125

Thr Gly Trp Gly Tyr His Ser Ser Arg Glu Lys Glu Ala Lys Arg Asn
                130                 135                 140

Arg Thr Phe Val Leu Asn Phe Ile Lys Ile Pro Val Val Pro His Asn
145                 150                 155                 160

Glu Cys Ser Glu Val Met Ser Asn Met Val Ser Glu Asn Met Leu Cys
                165                 170                 175

Ala Gly Ile Leu Gly Asp Arg Gln Asp Ala Cys Glu Gly Asp Ser Gly
                180                 185                 190

Gly Pro Met Val Ala Ser Phe His Gly Thr Trp Phe Leu Val Gly Leu
                195                 200                 205

Val Ser Trp Gly Glu Gly Cys Gly Leu Leu His Asn Tyr Gly Val Tyr
                210                 215                 220
```

-continued

```
Thr Lys Val Ser Arg Tyr Leu Asp Trp Ile His Gly His Ile Arg Asp
225                 230                 235                 240

Lys Glu Ala Pro Gln Lys Ser Trp Ala Pro
                245                 250
```

(2) INFORMATION FOR SEQ ID NO:52:

(i) SEQUENCE CHARACTERISTICS:
        (A) LENGTH: 259 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:52:

```
Ile Val Glu Gly Ser Asp Ala Glu Ile Gly Met Ser Pro Trp Gln Val
1               5                   10                  15

Met Leu Phe Arg Lys Ser Pro Gln Glu Leu Leu Cys Gly Ala Ser Leu
                20                  25                  30

Ile Ser Asp Arg Trp Val Leu Thr Ala Ala His Cys Leu Leu Tyr Pro
                35                  40                  45

Pro Trp Asp Lys Asn Phe Thr Glu Asn Asp Leu Leu Val Arg Ile Gly
                50                  55                  60

Lys His Ser Arg Thr Arg Tyr Glu Arg Asn Ile Glu Lys Ile Ser Met
65                  70                  75                  80

Leu Glu Lys Ile Tyr Ile His Pro Arg Tyr Asn Trp Arg Glu Asn Leu
                    85                  90                  95

Asp Arg Asp Ile Ala Leu Met Lys Leu Lys Lys Pro Val Ala Phe Ser
                100                 105                 110

Asp Tyr Ile His Pro Val Cys Leu Pro Asp Arg Glu Thr Ala Ala Ser
                115                 120                 125

Leu Leu Gln Ala Gly Tyr Lys Gly Arg Val Thr Gly Trp Gly Asn Leu
                130                 135                 140

Lys Glu Thr Trp Thr Ala Asn Val Gly Lys Gly Gln Pro Ser Val Leu
145                 150                 155                 160

Gln Val Val Asn Leu Pro Ile Val Glu Arg Pro Val Cys Lys Asp Ser
                    165                 170                 175

Thr Arg Ile Arg Ile Thr Asp Asn Met Phe Cys Ala Gly Tyr Lys Pro
                180                 185                 190

Asp Glu Gly Lys Arg Gly Asp Ala Cys Glu Gly Asp Ser Gly Gly Pro
                195                 200                 205

Phe Val Met Lys Ser Pro Phe Asn Asn Arg Trp Tyr Gln Met Gly Ile
                210                 215                 220

Val Ser Trp Gly Glu Gly Cys Asp Arg Asp Gly Lys Tyr Gly Phe Tyr
225                 230                 235                 240

Thr His Val Phe Arg Leu Lys Lys Trp Ile Gln Lys Val Ile Asp Gln
                    245                 250                 255

Phe Gly Glu
```

(2) INFORMATION FOR SEQ ID NO:53:

(i) SEQUENCE CHARACTERISTICS:
        (A) LENGTH: 230 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:53:

Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
            35                  40                  45

Arg Pro Ser Ser Tyr Lys Val Ile Leu Gly Ala His Gln Glu Val Asn
        50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
            115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg Asn Asn
225                 230

(2) INFORMATION FOR SEQ ID NO:54:

(i) SEQUENCE CHARACTERISTICS:
        (A) LENGTH: 221 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:54:

Ile Val Gly Gly Cys Val Ala His Pro His Ser Trp Pro Trp Gln Val
1               5                   10                  15

Ser Leu Arg Thr Arg Phe Gly Lys His Phe Cys Gly Gly Thr Leu Ile
            20                  25                  30

Ser Pro Glu Trp Val Leu Thr Ala Ala His Cys Leu Lys Lys Ser Ser
            35                  40                  45

Arg Pro Ser Ser Tyr Lys Val Ile Leu Gly Ala His Gln Glu Val Asn
        50                  55                  60

Leu Glu Ser His Val Gln Glu Ile Glu Val Ser Arg Leu Phe Leu Glu
65                  70                  75                  80

Pro Thr Gln Ala Asp Ile Ala Leu Leu Lys Leu Ser Arg Pro Ala Val
                85                  90                  95

```
Ile Thr Asp Lys Val Met Pro Ala Cys Leu Pro Ser Pro Asp Tyr Met
            100                 105                 110

Val Thr Ala Arg Thr Glu Cys Tyr Ile Thr Gly Trp Gly Glu Thr Gln
            115                 120                 125

Gly Thr Phe Gly Thr Gly Leu Leu Lys Glu Ala Gln Leu Leu Val Ile
            130                 135                 140

Glu Asn Glu Val Cys Asn His Tyr Lys Tyr Ile Cys Ala Glu His Leu
145                 150                 155                 160

Ala Arg Gly Thr Asp Ser Cys Gln Gly Asp Ser Gly Gly Pro Leu Val
            165                 170                 175

Cys Phe Glu Lys Asp Lys Tyr Ile Leu Gln Gly Val Thr Ser Trp Gly
            180                 185                 190

Leu Gly Cys Ala Arg Pro Asn Lys Pro Gly Val Tyr Ala Arg Val Ser
            195                 200                 205

Arg Phe Val Thr Trp Ile Glu Gly Met Met Arg Asn Asn
            210                 215                 220
```

(2) INFORMATION FOR SEQ ID NO:55:

(i) SEQUENCE CHARACTERISTICS:
        (A) LENGTH: 228 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:55:

```
Val Val Gly Gly His Pro Gly Asn Ser Pro Trp Thr Val Ser Leu Arg
1               5                   10                  15

Asn Arg Gln Gly Gln His Phe Cys Gly Gly Ser Leu Val Lys Glu Gln
            20                  25                  30

Trp Ile Leu Thr Ala Arg Gln Cys Phe Ser Ser Cys His Met Pro Leu
            35                  40                  45

Thr Gly Tyr Glu Val Trp Leu Gly Thr Leu Phe Gln Asn Pro Gln His
            50                  55                  60

Gly Glu Pro Ser Leu Gln Arg Val Pro Val Ala Lys Met Val Cys Gly
65                  70                  75                  80

Pro Ser Gly Ser Gln Leu Val Leu Leu Lys Leu Glu Arg Ser Val Thr
            85                  90                  95

Leu Asn Gln Arg Val Ala Leu Ile Cys Leu Pro Pro Glu Trp Tyr Val
            100                 105                 110

Val Pro Pro Gly Thr Lys Cys Glu Ile Ala Gly Trp Gly Glu Thr Lys
            115                 120                 125

Gly Thr Gly Asn Asp Thr Val Leu Asn Val Ala Phe Leu Asn Val Ile
            130                 135                 140

Ser Asn Gln Glu Cys Asn Ile Lys His Arg Gly Arg Val Arg Glu Ser
145                 150                 155                 160

Glu Met Cys Thr Glu Gly Leu Leu Ala Pro Val Gly Ala Cys Glu Gly
            165                 170                 175

Asp Tyr Gly Gly Pro Leu Ala Cys Phe Thr His Asn Cys Trp Val Leu
            180                 185                 190

Glu Gly Ile Ile Ile Pro Asn Arg Val Cys Ala Arg Ser Arg Trp Pro
            195                 200                 205
```

```
Ala Val Phe Thr Arg Val Ser Val Phe Val Asp Trp Ile His Lys Val
210                 215                 220

Met Arg Leu Gly
225
```

(2) INFORMATION FOR SEQ ID NO:56:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:56:

```
Val Val Asn Gly Ile Pro Thr Arg Thr Asn Ile Gly Trp Met Val Ser
1               5                   10                  15

Leu Arg Tyr Arg Asn Lys His Ile Cys Gly Ser Leu Ile Lys Glu
                20                  25                  30

Ser Trp Val Leu Thr Ala Arg Gln Cys Phe Pro Ser Arg Asp Leu Lys
            35                  40                  45

Asp Tyr Glu Ala Trp Leu Gly Ile His Asp Val His Gly Arg Gly Asp
        50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
                85                  90                  95

Asp Asp Phe Val Ser Thr Ile Asp Leu Pro Asn Tyr Gly Cys Thr Ile
                100                 105                 110

Pro Glu Lys Thr Ser Cys Ser Val Tyr Gly Trp Gly Tyr Thr Gly Leu
                115                 120                 125

Ile Asn Tyr Asp Gly Leu Leu Arg Val Ala His Leu Tyr Ile Met Gly
130                 135                 140

Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
                165                 170                 175

Gly Asp Tyr Gly Gly Pro Leu Val Cys Glu Gln His Lys Met Arg Met
                180                 185                 190

Val Leu Gly Val Ile Val Pro Gly Arg Gly Cys Ala Ile Pro Asn Arg
                195                 200                 205

Pro Gly Ile Phe Val Arg Val Ala Tyr Tyr Ala Lys Trp Ile His Lys
210                 215                 220

Ile Ile Leu Thr Tyr Lys Val Pro Gln Ser
225                 230
```

(2) INFORMATION FOR SEQ ID NO:57:

(i) SEQUENCE CHARACTERISTICS:
        (A) LENGTH: 242 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:57:

```
Val Val Asn Gly Glu Asp Ala Val Pro Tyr Ser Trp Pro Trp Gln Val
1               5                   10                  15
```

```
Ser Leu Gln Tyr Glu Lys Ser Gly Ser Phe Tyr His Thr Cys Gly Gly
            20                  25                  30

Ser Leu Ile Ala Pro Asp Trp Val Val Thr Ala Gly His Cys Ile Ser
        35                  40                  45

Ser Ser Arg Thr Tyr Gln Val Val Leu Gly Glu Tyr Asp Arg Ala Val
    50                  55                  60

Lys Glu Gly Pro Glu Gln Val Ile Pro Ile Asn Ser Gly Asp Leu Phe
65                  70                  75                  80

Val His Pro Leu Trp Asn Arg Ser Cys Val Ala Cys Gly Asn Asp Ile
                85                  90                  95

Ala Leu Ile Lys Leu Ser Arg Ser Ala Gln Leu Gly Asp Ala Val Gln
            100                 105                 110

Leu Ala Ser Leu Pro Pro Ala Gly Asp Ile Leu Pro Asn Glu Thr Pro
        115                 120                 125

Cys Tyr Ile Thr Gly Trp Gly Arg Leu Tyr Thr Asn Gly Pro Leu Pro
    130                 135                 140

Asp Lys Leu Gln Glu Ala Leu Leu Pro Val Val Asp Tyr Glu His Cys
145                 150                 155                 160

Ser Arg Trp Asn Trp Trp Gly Ser Ser Val Lys Lys Thr Met Val Cys
                165                 170                 175

Ala Gly Gly Asp Ile Arg Ser Gly Cys Asn Gly Asp Ser Gly Gly Pro
            180                 185                 190

Leu Asn Cys Pro Thr Glu Asp Gly Gly Trp Gln Val His Gly Val Thr
        195                 200                 205

Ser Phe Val Ser Ala Phe Gly Cys Asn Thr Arg Arg Lys Pro Thr Val
    210                 215                 220

Phe Thr Arg Val Ser Ala Phe Ile Asp Trp Ile Glu Glu Thr Ile Ala
225                 230                 235                 240

Ser His (2) INFORMATION FOR SEQ ID NO:58:

(i) SEQUENCE CHARACTERISTICS:
        (A) LENGTH: 242 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:58:

Val Val His Gly Glu Asp Ala Val Pro Tyr Ser Trp Pro Trp Gln Val
1               5                   10                  15

Ser Leu Gln Tyr Glu Lys Ser Gly Ser Phe Tyr His Thr Cys Gly Gly
            20                  25                  30

Ser Leu Ile Ala Pro Asp Trp Val Val Thr Ala Gly His Cys Ile Ser
        35                  40                  45

Arg Asp Leu Thr Tyr Gln Val Val Leu Gly Glu Tyr Asn Leu Ala Val
    50                  55                  60

Lys Glu Gly Pro Glu Gln Val Ile Pro Ile Asn Ser Glu Glu Leu Phe
65                  70                  75                  80

Val His Pro Leu Trp Asn Arg Ser Cys Val Ala Cys Gly Asn Asp Ile
                85                  90                  95

Ala Leu Ile Lys Leu Ser Arg Ser Ala Gln Leu Gly Asp Ala Val Gln
            100                 105                 110
```

```
Leu Ala Ser Leu Pro Pro Ala Gly Asp Ile Leu Pro Asn Lys Thr Pro
            115                 120                 125

Cys Tyr Ile Thr Gly Trp Gly Arg Leu Tyr Thr Asn Gly Pro Leu Pro
            130                 135                 140

Asp Lys Leu Gln Gln Ala Arg Leu Pro Val Val Asp Tyr Lys His Cys
145                 150                 155                 160

Ser Arg Trp Asn Trp Trp Gly Ser Thr Val Lys Thr Met Val Cys
            165                 170                 175

Ala Gly Gly Tyr Ile Arg Ser Gly Cys Asn Gly Asp Ser Gly Gly Pro
            180                 185                 190

Leu Asn Cys Pro Thr Glu Asp Gly Gly Trp Gln Val His Gly Val Thr
            195                 200                 205

Ser Phe Val Ser Gly Phe Gly Cys Asn Phe Ile Trp Lys Pro Thr Val
    210                 215                 220

Phe Thr Arg Val Ser Ala Phe Ile Asp Trp Ile Glu Glu Thr Ile Ala
225                 230                 235                 240

Ser His (2) INFORMATION FOR SEQ ID NO:59:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:59:

Val Val Gly Gly Glu Glu Ala Arg Pro Asn Ser Trp Pro Trp Gln Val
 1               5                  10                  15

Ser Leu Gln Tyr Ser Ser Asn Gly Lys Trp Tyr His Thr Cys Gly Gly
            20                  25                  30

Ser Leu Ile Ala Asn Ser Trp Val Leu Thr Ala Ala His Cys Ile Ser
            35                  40                  45

Ser Ser Arg Thr Tyr Arg Val Gly Leu Gly Arg His Asn Leu Tyr Val
    50                  55                  60

Ala Glu Ser Gly Ser Leu Ala Val Ser Val Ser Lys Ile Val Val His
65                  70                  75                  80

Lys Asp Trp Asn Ser Asn Gln Ile Ser Lys Gly Asn Asp Ile Ala Leu
            85                  90                  95

Leu Lys Leu Ala Asn Pro Val Ser Leu Thr Asp Lys Ile Gln Leu Ala
            100                 105                 110

Cys Leu Pro Pro Ala Gly Thr Ile Leu Pro Asn Asn Tyr Pro Cys Tyr
            115                 120                 125

Val Thr Gly Trp Gly Arg Leu Gln Thr Asn Gly Ala Val Pro Asp Val
            130                 135                 140

Leu Gln Gln Gly Arg Leu Leu Val Val Asp Tyr Ala Thr Cys Ser Ser
145                 150                 155                 160

Ser Ala Trp Trp Gly Ser Ser Val Lys Thr Ser Met Ile Cys Ala Gly
            165                 170                 175

Gly Asp Gly Val Ile Ser Ser Cys Asn Gly Asp Ser Gly Gly Pro Leu
            180                 185                 190

Asn Cys Gln Ala Ser Asp Gly Arg Trp Gln Val His Gly Ile Val Ser
            195                 200                 205
```

```
Phe Gly Ser Arg Leu Gly Cys Asn Tyr Tyr His Lys Pro Ser Val Phe
    210                 215                 220
Thr Arg Val Ser Asn Tyr Ile Asp Trp Ile Asn Ser Val Ile Ala Asn
225                 230                 235                 240
Asn
```

(2) INFORMATION FOR SEQ ID NO:60:

(i) SEQUENCE CHARACTERISTICS:
        (A) LENGTH: 241 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:60:

```
Met Leu Gly Gly Glu Glu Ala Arg Pro Asn Ser Trp Pro Trp Gln Val
1                   5                   10                  15
Ser Leu Gln Tyr Ser Ser Asn Gly Gln Trp Tyr His Thr Cys Gly Gly
                20                  25                  30
Ser Leu Ile Ala Asn Ser Trp Val Leu Thr Ala Ala His Cys Ile Ser
            35                  40                  45
Ser Ser Arg Ile Tyr Arg Val Met Leu Gly Gln His Asn Leu Tyr Val
    50                  55                  60
Ala Glu Ser Gly Ser Leu Ala Val Ser Val Ser Lys Ile Val Val His
65                  70                  75                  80
Lys Asp Trp Asn Ser Asn Gln Val Ser Lys Gly Asn Asp Ile Ala Leu
                85                  90                  95
Leu Lys Leu Ala Asn Pro Val Ser Leu Thr Asp Lys Ile Gln Leu Ala
            100                 105                 110
Cys Leu Pro Pro Ala Gly Thr Ile Leu Pro Asn Asn Tyr Pro Cys Tyr
            115                 120                 125
Val Thr Gly Trp Gly Arg Leu Gln Thr Asn Gly Ala Leu Pro Asp Asp
    130                 135                 140
Leu Lys Gln Gly Arg Leu Leu Val Val Asp Tyr Ala Thr Cys Ser Ser
145                 150                 155                 160
Ser Gly Trp Trp Gly Ser Thr Val Lys Thr Asn Met Ile Cys Ala Gly
                165                 170                 175
Gly Asp Gly Val Ile Cys Thr Cys Asn Gly Asp Ser Gly Gly Pro Leu
            180                 185                 190
Asn Cys Gln Ala Ser Asp Gly Arg Trp Glu Val His Gly Ile Gly Ser
            195                 200                 205
Leu Thr Ser Val Leu Gly Cys Asn Tyr Tyr Lys Pro Ser Ile Phe
    210                 215                 220
Thr Arg Val Ser Asn Tyr Asn Asp Trp Ile Asn Ser Val Ile Ala Asn
225                 230                 235                 240
Asn
```

(2) INFORMATION FOR SEQ ID NO:61:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:61:

```
Val Val Gly Gly Glu Asp Ala Arg Pro His Ser Trp Pro Trp Gln Ile
 1               5                  10                  15

Ser Leu Gln Tyr Leu Lys Asn Asp Thr Trp Arg His Thr Cys Gly Gly
                20                  25                  30

Thr Leu Ile Ala Ser Asn Phe Val Leu Thr Ala Ala His Cys Ile Ser
            35                  40                  45

Asn Thr Xaa Thr Tyr Arg Val Ala Val Gly Lys Asn Asn Leu Glu Val
        50                  55                  60

Glu Asp Glu Glu Gly Ser Leu Phe Val Gly Val Asp Thr Ile His Val
 65                  70                  75                  80

His Lys Arg Trp Asn Ala Leu Leu Leu Arg Asn Asp Ile Ala Leu Ile
                85                  90                  95

Lys Leu Ala Glu His Val Glu Leu Ser Asp Thr Ile Gln Val Ala Cys
                100                 105                 110

Leu Pro Glu Lys Asp Ser Leu Leu Pro Lys Asp Tyr Pro Cys Tyr Val
            115                 120                 125

Thr Gly Trp Gly Arg Leu Trp Thr Asn Gly Pro Ile Ala Asp Lys Leu
        130                 135                 140

Gln Gln Gly Leu Gln Pro Val Val Asp His Ala Thr Cys Ser Arg Ile
145                 150                 155                 160

Asp Trp Trp Gly Phe Arg Val Lys Lys Thr Met Val Cys Ala Gly Gly
                165                 170                 175

Asp Gly Val Ile Ser Ala Cys Asn Gly Asp Ser Gly Gly Pro Leu Asn
            180                 185                 190

Cys Gln Leu Glu Asn Gly Ser Trp Glu Val Phe Gly Ile Val Ser Phe
        195                 200                 205

Gly Ser Arg Arg Gly Cys Asn Thr Arg Lys Lys Pro Val Val Tyr Thr
    210                 215                 220

Arg Val Ser Ala Tyr Ile Asp Trp Ile Asn Glu Lys Met Gln Leu
225                 230                 235
```

(2) INFORMATION FOR SEQ ID NO:62:

(i) SEQUENCE CHARACTERISTICS:
        (A) LENGTH: 230 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:62:

```
Ile Val Asn Gly Glu Asp Ala Val Pro Gly Ser Trp Pro Trp Gln Val
 1               5                  10                  15

Ser Leu Gln Asp Lys Thr Gly Phe His Phe Cys Gly Gly Ser Leu Ile
                20                  25                  30

Ser Glu Asp Trp Val Val Thr Ala Ala His Cys Gly Val Arg Thr Ser
            35                  40                  45

Asp Val Val Val Ala Gly Glu Phe Asp Gln Gly Ser Asp Glu Glu Asn
        50                  55                  60

Ile Gln Val Leu Lys Ile Ala Lys Val Phe Lys Asn Pro Lys Phe Ser
 65                  70                  75                  80

Ile Leu Thr Val Asn Asn Asp Ile Thr Leu Leu Lys Leu Ala Thr Pro
                85                  90                  95
```

```
Ala Arg Phe Ser Gln Thr Val Ser Ala Val Cys Leu Pro Ser Ala Asp
            100                 105                 110

Asp Asp Phe Pro Ala Gly Thr Leu Cys Ala Thr Thr Gly Trp Gly Lys
            115                 120                 125

Thr Lys Tyr Asn Ala Asn Lys Thr Pro Asp Lys Leu Gln Gln Ala Ala
            130                 135                 140

Leu Pro Leu Leu Ser Asn Ala Glu Cys Lys Lys Ser Trp Gly Arg Arg
145                 150                 155                 160

Ile Thr Asp Val Met Ile Cys Ala Gly Ala Ser Gly Val Ser Ser Cys
                165                 170                 175

Met Gly Asp Ser Gly Gly Pro Leu Val Cys Gln Lys Asp Gly Ala Trp
            180                 185                 190

Thr Leu Val Gly Ile Val Ser Trp Gly Ser Asp Thr Cys Ser Thr Ser
            195                 200                 205

Ser Pro Gly Val Tyr Ala Arg Val Thr Lys Leu Ile Pro Trp Val Gln
            210                 215                 220

Lys Ile Leu Ala Ala Asn
225                 230
```

(2) INFORMATION FOR SEQ ID NO:63:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:63:

```
Ile Val Gly Gly Thr Asn Ser Ser Trp Gly Glu Trp Pro Trp Gln Val
1               5                   10                  15

Ser Leu Gln Val Lys Leu Thr Ala Gln Arg His Leu Cys Gly Gly Ser
            20                  25                  30

Leu Ile Gly His Gln Trp Val Leu Thr Ala Ala His Cys Phe Asp Gly
            35                  40                  45

Leu Pro Leu Gln Asp Val Trp Arg Ile Tyr Ser Gly Ile Leu Asn Leu
50                  55                  60

Ser Asp Ile Thr Lys Asp Thr Pro Phe Ser Gln Ile Lys Glu Ile Ile
65                  70                  75                  80

Ile His Gln Asn Tyr Lys Val Ser Glu Gly Asn His Asp Ile Ala Leu
                85                  90                  95

Ile Lys Leu Gln Ala Pro Leu Asn Tyr Thr Glu Phe Gln Lys Pro Ile
            100                 105                 110

Cys Leu Pro Ser Lys Gly Asp Thr Ser Thr Ile Tyr Thr Asn Cys Trp
            115                 120                 125

Val Thr Gly Trp Gly Phe Ser Lys Glu Lys Gly Glu Ile Gln Asn Ile
            130                 135                 140

Leu Gln Lys Val Asn Ile Pro Leu Val Thr Asn Glu Glu Cys Gln Lys
145                 150                 155                 160

Arg Tyr Gln Asp Tyr Lys Ile Thr Gln Arg Met Val Cys Ala Gly Tyr
                165                 170                 175

Lys Glu Gly Gly Lys Asp Ala Cys Lys Gly Asp Ser Gly Gly Pro Leu
            180                 185                 190

Val Cys Lys His Asn Gly Met Trp Arg Leu Val Gly Ile Thr Ser Trp
            195                 200                 205
```

```
Gly Glu Gly Cys Ala Arg Arg Glu Gln Pro Val Tyr Thr Lys Val
    210                 215                 220

Ala Glu Tyr Met Asp Trp Ile Leu Glu Lys Thr Gln Ser Ser Asp Gly
225                 230                 235                 240

Lys Ala Gln Met Gln Ser Pro Ala
                245
```

(2) INFORMATION FOR SEQ ID NO:64:

(i) SEQUENCE CHARACTERISTICS:
        (A) LENGTH: 238 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:64:

```
Ile Val Gly Gly Thr Ala Ser Val Arg Gly Glu Trp Pro Trp Gln Val
1               5                   10                  15

Thr Leu His Thr Thr Ser Pro Thr Gln Arg His Leu Cys Gly Gly Ser
            20                  25                  30

Ile Ile Gly Asn Gln Trp Ile Leu Thr Ala Ala His Cys Phe Tyr Gly
        35                  40                  45

Val Glu Ser Pro Lys Ile Leu Arg Val Tyr Ser Gly Ile Leu Asn Gln
50                  55                  60

Ser Glu Ile Lys Glu Asp Thr Ser Phe Phe Gly Val Gln Glu Ile Ile
65                  70                  75                  80

Ile His Asp Gln Tyr Lys Met Ala Glu Ser Gly Tyr Asp Ile Ala Leu
                85                  90                  95

Leu Lys Leu Glu Thr Thr Val Asn Tyr Thr Asp Ser Gln Arg Pro Ile
                100                 105                 110

Cys Leu Pro Ser Lys Gly Asp Arg Asn Val Ile Tyr Thr Asp Cys Trp
            115                 120                 125

Val Thr Gly Trp Gly Tyr Arg Lys Leu Arg Asp Lys Ile Gln Asn Thr
    130                 135                 140

Leu Gln Lys Ala Lys Ile Pro Leu Val Thr Asn Glu Glu Cys Gln Lys
145                 150                 155                 160

Arg Tyr Arg Gly His Lys Ile Thr His Lys Met Ile Cys Ala Gly Tyr
                165                 170                 175

Arg Glu Gly Gly Lys Asp Ala Cys Lys Gly Asp Ser Gly Gly Pro Leu
                180                 185                 190

Ser Cys Lys His Asn Glu Val Trp His Leu Val Gly Ile Thr Ser Trp
            195                 200                 205

Gly Glu Gly Cys Ala Gln Arg Glu Arg Pro Gly Val Tyr Thr Asn Val
    210                 215                 220

Val Glu Tyr Val Asp Trp Ile Leu Glu Lys Thr Gln Ala Val
225                 230                 235
```

(2) INFORMATION FOR SEQ ID NO:65:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:65:

```
Ile Val Gly Gly Ser Asn Ala Lys Glu Gly Ala Trp Pro Trp Val Val
1               5                   10                  15
Gly Leu Tyr Tyr Gly Gly Arg Leu Leu Cys Gly Ala Ser Leu Val Ser
            20                  25                  30
Ser Asp Trp Leu Val Ser Ala Ala His Cys Val Tyr Gly Arg Asn Leu
        35                  40                  45
Glu Pro Ser Lys Trp Thr Ala Ile Leu Gly Leu His Met Lys Ser Asn
50                  55                  60
Leu Thr Ser Pro Gln Thr Val Pro Arg Leu Ile Asp Glu Ile Val Ile
65                  70                  75                  80
Asn Pro His Tyr Asn Arg Arg Lys Asp Asn Asp Ile Ala Met Met
                85                  90                  95
His Leu Glu Phe Lys Val Asn Tyr Thr Asp Tyr Ile Gln Pro Ile Cys
            100                 105                 110
Leu Pro Glu Glu Asn Gln Val Phe Pro Pro Gly Arg Asn Cys Ser Ile
            115                 120                 125
Ala Gly Trp Gly Thr Val Val Tyr Gln Gly Thr Thr Ala Asn Ile Leu
            130                 135                 140
Gln Glu Ala Asp Val Pro Leu Leu Ser Asn Glu Arg Cys Gln Gln
145                 150                 155                 160
Met Pro Glu Tyr Asn Ile Thr Glu Asn Met Ile Cys Ala Gly Tyr Glu
                165                 170                 175
Glu Gly Gly Ile Asp Ser Cys Gln Gly Asp Ser Gly Gly Pro Leu Met
            180                 185                 190
Cys Gln Glu Asn Asn Arg Trp Phe Leu Ala Gly Val Thr Ser Phe Gly
            195                 200                 205
Tyr Lys Cys Ala Leu Pro Asn Arg Pro Gly Val Tyr Ala Arg Val Ser
            210                 215                 220
Arg Phe Thr Glu Trp Ile Gln Ser Phe Leu His
225                 230                 235
```

(2) INFORMATION FOR SEQ ID NO:66:

(i) SEQUENCE CHARACTERISTICS:
        (A) LENGTH: 299 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:66:

```
Ile Thr Gly Gly Ser Ser Ala Val Ala Gly Gln Trp Pro Trp Gln Val
1               5                   10                  15
Ser Ile Thr Tyr Glu Gly Val His Val Cys Gly Gly Ser Leu Val Ser
            20                  25                  30
Glu Gln Trp Val Leu Ser Ala Ala His Cys Phe Pro Ser Glu His His
        35                  40                  45
Lys Glu Ala Tyr Glu Val Lys Leu Gly Ala His Gln Leu Asp Ser Tyr
        50                  55                  60
Ser Glu Asp Ala Lys Val Ser Thr Leu Lys Asp Ile Ile Pro His Pro
65                  70                  75                  80
Ser Tyr Leu Gln Glu Gly Ser Gln Gly Asp Ile Ala Leu Leu Gln Leu
                85                  90                  95
```

```
Ser Arg Pro Ile Thr Phe Ser Arg Tyr Ile Arg Pro Ile Cys Leu Pro
            100                 105                 110

Ala Ala Asn Ala Ser Phe Pro Asn Gly Leu His Cys Thr Val Thr Gly
            115                 120                 125

Trp Gly His Val Ala Pro Ser Val Ser Leu Leu Thr Pro Lys Pro Leu
            130                 135                 140

Gln Gln Leu Glu Val Pro Leu Ile Ser Arg Glu Thr Cys Asn Cys Leu
145                 150                 155                 160

Tyr Asn Ile Asp Ala Lys Pro Glu Glu Pro His Phe Val Gln Glu Asp
            165                 170                 175

Met Val Cys Ala Gly Tyr Val Glu Gly Gly Lys Asp Ala Cys Gln Gly
            180                 185                 190

Asp Ser Gly Gly Pro Leu Ser Cys Pro Val Glu Gly Leu Trp Tyr Leu
            195                 200                 205

Thr Gly Ile Val Ser Trp Gly Asp Ala Cys Gly Ala Arg Asn Arg Pro
            210                 215                 220

Gly Val Tyr Thr Leu Ala Ser Ser Tyr Ala Ser Trp Ile Gln Ser Lys
225                 230                 235                 240

Val Thr Glu Leu Gln Pro Arg Val Val Pro Gln Thr Gln Glu Ser Gln
            245                 250                 255

Pro Asp Ser Asn Leu Cys Gly Ser His Leu Ala Phe Ser Ser Ala Pro
            260                 265                 270

Ala Gln Gly Leu Leu Arg Pro Ile Leu Phe Leu Pro Leu Gly Leu Ala
            275                 280                 285

Leu Gly Leu Leu Ser Pro Trp Leu Ser Glu His
            290                 295

(2) INFORMATION FOR SEQ ID NO:67:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:67:

Ile Val Gly Gly Arg Asp Thr Ser Leu Gly Arg Trp Pro Trp Gln Val
1               5                   10                  15

Ser Leu Arg Tyr Asp Gly Ala His Leu Cys Gly Gly Ser Leu Leu Ser
            20                  25                  30

Gly Asp Trp Val Leu Thr Ala Ala His Cys Phe Pro Glu Arg Asn Arg
            35                  40                  45

Val Leu Ser Arg Trp Arg Val Phe Ala Gly Ala Val Ala Gln Ala Ser
50                  55                  60

Pro His Gly Leu Gln Leu Gly Val Gln Ala Val Val Tyr His Gly Gly
65                  70                  75                  80

Tyr Leu Pro Phe Arg Asp Pro Asn Ser Glu Glu Asn Ser Asn Asp Ile
            85                  90                  95

Ala Leu Val His Leu Ser Ser Pro Leu Pro Leu Thr Glu Tyr Ile Gln
            100                 105                 110

Pro Val Cys Leu Pro Ala Ala Gly Gln Ala Leu Val Asp Gly Lys Ile
            115                 120                 125

Cys Thr Val Thr Gly Trp Gly Asn Thr Gln Tyr Tyr Gly Gln Gln Ala
            130                 135                 140
```

```
Gly Val Leu Gln Glu Ala Arg Val Pro Ile Ile Ser Asn Asp Val Cys
145                 150                 155                 160

Asn Gly Ala Asp Phe Tyr Gly Asn Gln Ile Lys Pro Lys Met Phe Cys
            165                 170                 175

Ala Gly Tyr Pro Glu Gly Gly Ile Asp Ala Cys Gln Gly Asp Ser Gly
            180                 185                 190

Gly Pro Phe Val Cys Glu Asp Ser Ile Ser Arg Thr Pro Arg Trp Arg
            195                 200                 205

Leu Cys Gly Ile Val Ser Trp Gly Thr Gly Cys Ala Leu Ala Gln Lys
            210                 215                 220

Pro Gly Val Tyr Thr Lys Val Ser Asp Phe Arg Glu Trp Ile Phe Gln
225                 230                 235                 240

Ala Ile Lys Thr His Ser Glu Ala Ser Gly Met Val Thr Gln Leu
            245                 250                 255

(2) INFORMATION FOR SEQ ID NO:68:

(i) SEQUENCE CHARACTERISTICS:
        (A) LENGTH: 250 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:68:

Ile Val Gly Gly Lys Ala Ala Gln His Gly Ala Trp Pro Trp Met Val
1                   5                   10                  15

Ser Leu Gln Ile Phe Arg Tyr Asn Ser His Arg Tyr His Thr Cys Gly
            20                  25                  30

Gly Ser Leu Leu Asn Ser Arg Trp Val Leu Thr Ala Ala His Cys Phe
            35                  40                  45

Val Gly Lys Asn Asn Val His Asp Trp Arg Leu Val Phe Gly Ala Lys
            50                  55                  60

Glu Ile Thr Tyr Gly Asn Asn Lys Pro Val Lys Ala Pro Leu Gln Glu
65                  70                  75                  80

Arg Tyr Val Glu Lys Ile Ile His Glu Lys Tyr Asn Ser Ala Thr
            85                  90                  95

Glu Gly Asn Asp Ile Ala Leu Val Glu Ile Thr Pro Pro Ile Ser Cys
            100                 105                 110

Gly Arg Phe Ile Gly Pro Gly Cys Leu Pro His Phe Lys Ala Gly Leu
            115                 120                 125

Pro Arg Gly Ser Gln Ser Cys Trp Val Ala Gly Trp Gly Tyr Ile Glu
            130                 135                 140

Glu Lys Pro Arg Pro Ser Ser Ile Leu Met Glu Ala Arg Val Asp Leu
145                 150                 155                 160

Ile Asp Leu Asp Leu Cys Asn Ser Thr Gln Trp Tyr Asn Gly Arg Val
            165                 170                 175

Gln Pro Thr Asn Val Cys Ala Gly Tyr Pro Val Gly Lys Ile Asp Thr
            180                 185                 190

Cys Gln Gly Asp Ser Gly Gly Pro Leu Met Cys Lys Asp Ser Lys Glu
            195                 200                 205

Ser Ala Tyr Val Val Gly Ile Thr Ser Trp Gly Val Gly Cys Ala
            210                 215                 220
```

```
Leu Ala Lys Arg Pro Gly Ile Tyr Thr Ala Thr Trp Pro Tyr Leu Asn
225                 230                 235                 240

Trp Ile Ala Ser Lys Ile Gly Ser Asn Ala
                245                 250
```

(2) INFORMATION FOR SEQ ID NO:69:

(i) SEQUENCE CHARACTERISTICS:
        (A) LENGTH: 245 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:69:

```
Ile Val Gly Gly Gln Glu Ala Pro Arg Ser Lys Trp Pro Trp Gln Val
1                   5                   10                  15

Ser Leu Arg Val Arg Asp Arg Tyr Trp Met His Phe Cys Gly Gly Ser
                20                  25                  30

Leu Ile His Pro Gln Trp Val Leu Thr Ala Ala His Cys Leu Gly Pro
                35                  40                  45

Asp Val Lys Asp Leu Ala Thr Leu Arg Val Gln Leu Arg Glu Gln His
            50                  55                  60

Leu Tyr Tyr Gln Asp Gln Leu Leu Pro Val Ser Arg Ile Ile Val His
65                  70                  75                  80

Pro Gln Phe Tyr Ile Ile Gln Thr Gly Ala Asp Ile Ala Leu Leu Glu
                85                  90                  95

Leu Glu Glu Pro Val Asn Ile Ser Ser Arg Val His Thr Val Met Leu
                100                 105                 110

Pro Pro Ala Ser Glu Thr Phe Pro Pro Gly Met Pro Cys Trp Val Thr
                115                 120                 125

Gly Trp Gly Asp Val Asp Asn Asp Glu Pro Leu Pro Pro Phe Pro
                130                 135                 140

Leu Lys Gln Val Lys Val Pro Ile Met Glu Asn His Ile Cys Asp Ala
145                 150                 155                 160

Lys Tyr His Leu Gly Ala Tyr Thr Gly Asp Asp Val Arg Ile Ile Arg
                165                 170                 175

Asp Asp Met Leu Cys Ala Gly Asn Ser Gln Arg Asp Ser Cys Lys Gly
                180                 185                 190

Asp Ser Gly Gly Pro Leu Val Cys Lys Val Asn Gly Thr Trp Leu Gln
                195                 200                 205

Ala Gly Val Val Ser Trp Asp Glu Gly Cys Ala Gln Pro Asn Arg Pro
                210                 215                 220

Gly Ile Tyr Thr Arg Val Thr Tyr Tyr Leu Asp Trp Ile His His Tyr
225                 230                 235                 240

Val Pro Lys Lys Pro
                245
```

(2) INFORMATION FOR SEQ ID NO:70:

(i) SEQUENCE CHARACTERISTICS:
        (A) LENGTH: 243 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:70:

```
Val Val Gly Gly Leu Val Ala Leu Arg Gly Ala His Pro Tyr Ile Ala
1               5                  10                 15

Ala Leu Tyr Trp Gly His Ser Phe Cys Ala Gly Ser Leu Ile Ala Pro
            20                  25                 30

Cys Trp Val Leu Thr Ala Ala His Cys Leu Gln Asp Arg Pro Ala Pro
        35                  40                  45

Glu Asp Leu Thr Val Val Leu Gly Gln Glu Arg Arg Asn His Ser Cys
50                  55                  60

Glu Pro Cys Gln Thr Leu Ala Val Arg Ser Tyr Arg Leu His Glu Ala
65                  70                  75                  80

Phe Ser Pro Val Ser Tyr Gln His Asp Leu Ala Leu Leu Arg Leu Gln
                85                  90                  95

Glu Asp Ala Asp Gly Ser Cys Ala Leu Leu Ser Pro Tyr Val Gln Pro
            100                 105                 110

Val Cys Leu Pro Ser Gly Ala Ala Arg Pro Ser Glu Thr Thr Leu Cys
        115                 120                 125

Gln Val Ala Gly Trp Gly His Gln Phe Glu Gly Ala Glu Glu Tyr Ala
130                 135                 140

Ser Phe Leu Gln Glu Ala Gln Val Pro Phe Leu Ser Leu Glu Arg Cys
145                 150                 155                 160

Ser Ala Pro Asp Val His Gly Ser Ser Ile Leu Pro Gly Met Leu Cys
                165                 170                 175

Ala Gly Phe Leu Glu Gly Gly Thr Asp Ala Cys Gln Gly Asp Ser Gly
            180                 185                 190

Gly Pro Leu Val Cys Glu Asp Gln Ala Ala Glu Arg Arg Leu Thr Leu
        195                 200                 205

Gln Gly Ile Ile Ser Trp Gly Ser Gly Cys Gly Asp Arg Asn Lys Pro
210                 215                 220

Gly Val Tyr Thr Asp Val Ala Tyr Tyr Leu Ala Trp Ile Arg Glu His
225                 230                 235                 240

Thr Val Ser
```

(2) INFORMATION FOR SEQ ID NO:71:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:71:

```
Ile Ile Gly Gly Ser Ser Ser Leu Pro Gly Ser His Pro Trp Leu Ala
1               5                  10                 15

Ala Ile Tyr Ile Gly Asp Ser Phe Cys Ala Gly Ser Leu Val His Thr
            20                  25                 30

Cys Trp Val Val Ser Ala Ala His Cys Phe Ser His Ser Pro Pro Arg
        35                  40                  45

Asp Ser Val Ser Val Val Leu Gly Gln His Phe Phe Asn Arg Thr Thr
50                  55                  60

Asp Val Thr Gln Thr Phe Gly Ile Glu Lys Tyr Ile Pro Tyr Thr Leu
65                  70                  75                  80

Tyr Ser Val Phe Asn Pro Ser Asp His Asp Leu Val Leu Ile Arg Leu
                85                  90                  95
```

```
Lys Lys Lys Gly Asp Arg Cys Ala Thr Arg Ser Gln Phe Val Gln Pro
             100                 105                 110

Ile Cys Leu Pro Glu Pro Gly Ser Thr Phe Pro Ala Gly His Lys Cys
         115                 120                 125

Gln Ile Ala Gly Trp Gly His Leu Asp Glu Asn Val Ser Gly Tyr Ser
     130                 135                 140

Ser Ser Leu Arg Glu Ala Leu Val Pro Leu Val Ala Asp His Lys Cys
145                 150                 155                 160

Ser Ser Pro Glu Val Tyr Gly Ala Asp Ile Ser Pro Asn Met Leu Cys
                 165                 170                 175

Ala Gly Tyr Phe Asp Cys Lys Ser Asp Ala Cys Gln Gly Asp Ser Gly
             180                 185                 190

Gly Pro Leu Ala Cys Glu Lys Asn Gly Val Ala Tyr Leu Tyr Gly Ile
         195                 200                 205

Ile Ser Trp Gly Asp Gly Cys Gly Arg Leu His Lys Pro Gly Val Tyr
     210                 215                 220

Thr Arg Val Ala Asn Tyr Val Asp Trp Ile Asn Asp Arg Ile Arg Pro
225                 230                 235                 240

Pro Arg Arg Leu Val Ala Pro Ser
                 245

(2) INFORMATION FOR SEQ ID NO:72:

(i) SEQUENCE CHARACTERISTICS:
        (A) LENGTH: 252 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:72:

Ile Lys Gly Gly Leu Phe Ala Asp Ile Ala Ser His Pro Trp Gln Ala
 1               5                  10                  15

Ala Ile Phe Ala Lys His Arg Arg Ser Pro Gly Glu Arg Phe Leu Cys
             20                  25                  30

Gly Gly Ile Leu Ile Ser Ser Cys Trp Ile Leu Ser Ala Ala His Cys
         35                  40                  45

Phe Gln Glu Arg Phe Pro Pro His Leu Thr Val Ile Leu Gly Arg
 50                  55                  60

Thr Tyr Arg Val Val Pro Gly Glu Glu Gln Lys Phe Glu Val Glu
 65                  70                  75                  80

Lys Tyr Ile Val His Lys Glu Phe Asp Asp Asp Thr Tyr Asp Asn Asp
                 85                  90                  95

Ile Ala Leu Leu Gln Leu Lys Ser Asp Ser Ser Arg Cys Ala Gln Glu
             100                 105                 110

Ser Ser Val Val Arg Thr Val Cys Leu Pro Pro Ala Asp Leu Gln Leu
         115                 120                 125

Pro Asp Trp Thr Glu Cys Glu Leu Ser Gly Tyr Gly Lys His Glu Ala
     130                 135                 140

Leu Ser Pro Phe Tyr Ser Glu Arg Leu Lys Glu Ala His Val Arg Leu
145                 150                 155                 160

Tyr Pro Ser Ser Arg Cys Thr Ser Gln His Leu Leu Asn Arg Thr Val
                 165                 170                 175

Thr Asp Asn Met Leu Cys Ala Gly Asp Thr Arg Ser Gly Gly Pro Gln
             180                 185                 190
```

-continued

```
Ala Asn Leu His Asp Ala Cys Gln Gly Asp Ser Gly Gly Pro Leu Val
        195                 200                 205

Cys Leu Asn Asp Gly Arg Met Thr Leu Val Gly Ile Ile Ser Trp Gly
210                 215                 220

Leu Gly Cys Gly Gln Lys Asp Val Pro Gly Val Tyr Thr Lys Val Thr
225                 230                 235                 240

Asn Tyr Leu Asp Trp Ile Arg Asp Asn Met Arg Pro
                245                 250
```

(2) INFORMATION FOR SEQ ID NO:73:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:73:

```
Ile Ile Gly Gly Glu Phe Thr Thr Ile Glu Asn Gln Pro Trp Phe Ala
1               5                   10                  15

Ala Ile Tyr Arg Arg His Arg Gly Gly Ser Val Thr Tyr Val Cys Gly
            20                  25                  30

Gly Ser Leu Ile Ser Pro Cys Trp Val Ile Ser Ala Thr His Cys Phe
        35                  40                  45

Ile Asp Tyr Pro Lys Lys Glu Asp Tyr Ile Val Tyr Leu Gly Arg Ser
    50                  55                  60

Arg Leu Asn Ser Asn Thr Gln Gly Glu Met Lys Phe Glu Val Glu Asn
65                  70                  75                  80

Leu Ile Leu His Lys Asp Tyr Ser Ala Asp Thr Leu Ala His His Asn
                85                  90                  95

Asp Ile Ala Leu Leu Lys Ile Arg Ser Lys Glu Gly Arg Cys Ala Gln
            100                 105                 110

Pro Ser Arg Thr Ile Gln Thr Ile Cys Leu Pro Ser Met Tyr Asn Asp
        115                 120                 125

Pro Gln Phe Gly Thr Ser Cys Glu Ile Thr Gly Phe Gly Lys Glu Asn
    130                 135                 140

Ser Thr Asp Tyr Leu Tyr Pro Glu Gln Leu Lys Met Thr Val Val Lys
145                 150                 155                 160

Leu Ile Ser His Arg Glu Cys Gln Gln Pro His Tyr Tyr Gly Ser Glu
                165                 170                 175

Val Thr Thr Lys Met Leu Cys Ala Ala Asp Pro Gln Trp Lys Thr Asp
            180                 185                 190

Ser Cys Gln Gly Asp Ser Gly Gly Pro Leu Val Cys Ser Leu Gln Gly
        195                 200                 205

Arg Met Thr Leu Thr Gly Ile Val Ser Trp Gly Arg Gly Cys Ala Leu
    210                 215                 220

Lys Asp Lys Pro Gly Val Tyr Thr Arg Val Ser His Phe Leu Pro Trp
225                 230                 235                 240

Ile Arg Ser His Thr Lys Glu Glu Asn Gly Leu Ala Leu
                245                 250
```

(2) INFORMATION FOR SEQ ID NO:74:

(i) SEQUENCE CHARACTERISTICS:
        (A) LENGTH: 244 amino acids
        (B) TYPE: amino acid (C) STRANDEDNESS: single
        (D) TOPOLOGY: linear (ii) MOLECULE TYPE: None (xi) SEQUENCE DESCRIPTION: SEQ ID NO:74:

Ile Val Gly Gly Lys Arg Ala Gln Leu Gly Asp Leu Pro Trp Gln Val
1               5                  10                  15

Ala Ile Lys Asp Ala Ser Gly Ile Thr Cys Gly Gly Ile Tyr Ile Gly
                20                  25                  30

Gly Cys Trp Ile Leu Thr Ala Ala His Cys Leu Arg Ala Ser Lys Thr
            35                  40                  45

His Arg Tyr Gln Ile Trp Thr Thr Val Val Asp Trp Ile His Pro Asp
    50                  55                  60

Leu Lys Arg Ile Val Ile Glu Tyr Val Asp Arg Ile Ile Phe His Glu
65                  70                  75                  80

Asn Tyr Asn Ala Gly Thr Tyr Gln Asn Asp Ile Ala Leu Ile Glu Met
                85                  90                  95

Lys Lys Asp Gly Asn Lys Lys Asp Cys Glu Leu Pro Arg Ser Ile Pro
                100                 105                 110

Ala Cys Val Pro Trp Ser Pro Tyr Leu Phe Gln Pro Asn Asp Thr Cys
            115                 120                 125

Ile Val Ser Gly Trp Gly Arg Glu Lys Asp Asn Glu Arg Val Phe Ser
130                 135                 140

Leu Gln Trp Gly Glu Val Lys Leu Ile Ser Asn Cys Ser Lys Phe Tyr
145                 150                 155                 160

Gly Asn Arg Phe Tyr Glu Lys Glu Met Glu Cys Ala Gly Thr Tyr Asp
                165                 170                 175

Gly Ser Ile Asp Ala Cys Lys Gly Asp Ser Gly Gly Pro Leu Val Cys
            180                 185                 190

Met Asp Ala Asn Asn Val Thr Tyr Val Trp Gly Val Val Ser Trp Gly
        195                 200                 205

Glu Asn Cys Gly Lys Pro Glu Phe Pro Gly Phe Tyr Thr Lys Val Ala
210                 215                 220

Asn Tyr Phe Asp Trp Ile Ser Tyr His Val Gly Arg Pro Phe Ile Ser
225                 230                 235                 240

Gln Tyr Asn Val (2) INFORMATION FOR SEQ ID NO:75:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:75:

Asp Tyr Lys Asp Asp Asp Asp Lys
1               5

(2) INFORMATION FOR SEQ ID NO:76:

(i) SEQUENCE CHARACTERISTICS:
        (A) LENGTH: 21 amino acids
        (B) TYPE: amino acid
        (C) STRANDEDNESS: single
        (D) TOPOLOGY: linear -continued (xi) SEQUENCE DESCRIPTION: SEQ ID NO:76:

Glu Gln Lys Leu Ile Ser Glu Glu Asp Leu Asn Met His Thr Glu His
1               5                   10                  15

His His His His His
            20